(12) United States Patent
Oldfield et al.

(10) Patent No.: US 7,687,482 B2
(45) Date of Patent: Mar. 30, 2010

(54) BISPHOSPHONATE COMPOUNDS AND METHODS

(75) Inventors: Eric Oldfield, Champaign, IL (US); Yongcheng Song, Urbana, IL (US); Yonghui Zhang, Urbana, IL (US); John M. Sanders, Collegeville, PA (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 11/687,570

(22) Filed: Mar. 16, 2007

(65) Prior Publication Data

US 2007/0275931 A1 Nov. 29, 2007

Related U.S. Application Data

(60) Provisional application No. 60/783,491, filed on Mar. 17, 2006.

(51) Int. Cl.
*A61K 31/66* (2006.01)
*C07F 9/02* (2006.01)

(52) U.S. Cl. .................. 514/102; 558/155; 558/156

(58) Field of Classification Search ............ 558/155, 558/156; 514/102
See application file for complete search history.

(56) References Cited

U.S. PATENT DOCUMENTS

| | | | | |
|---|---|---|---|---|
| 4,608,368 | A * | 8/1986 | Blum et al. | ............... 514/107 |
| 4,621,077 | A | 11/1986 | Rosini et al. | |
| 4,711,880 | A | 12/1987 | Stahl et al. | |
| 4,777,163 | A | 10/1988 | Boises et al. | |
| 4,810,486 | A | 3/1989 | Kelly et al. | |
| 4,859,472 | A | 8/1989 | Demmer et al. | |
| 4,871,720 | A | 10/1989 | Jaeggi | |
| 4,927,814 | A | 5/1990 | Gall et al. | |
| 4,939,130 | A | 7/1990 | Jaeggi et al. | |
| 5,196,409 | A | 3/1993 | Breuer et al. | |
| 5,227,506 | A | 7/1993 | Saari et al. | |
| 5,294,608 | A | 3/1994 | Lang et al. | |
| 5,312,954 | A | 5/1994 | Breuer et al. | |
| 5,338,731 | A | 8/1994 | Breuer et al. | |
| 5,462,932 | A | 10/1995 | Brenner et al. | |
| 5,583,122 | A | 12/1996 | Benedict et al. | |
| 5,719,303 | A | 2/1998 | Yoshida et al. | |
| 5,756,423 | A | 5/1998 | Cromartie et al. | |
| 5,994,329 | A | 11/1999 | Daifotis et al. | |
| 6,015,801 | A | 1/2000 | Daifotis et al. | |
| 6,057,306 | A | 5/2000 | Wilson et al. | |
| 6,096,342 | A | 8/2000 | Dansereau et al. | |
| 6,143,326 | A | 11/2000 | Mockel et al. | |
| 6,165,513 | A | 12/2000 | Dansereau et al. | |
| 6,214,812 | B1 | 4/2001 | Karpeisky et al. | |
| 6,225,294 | B1 | 5/2001 | Daifotis et al. | |
| 6,294,196 | B1 | 9/2001 | Gabel et al. | |
| 6,372,728 | B1 | 4/2002 | Ungell | |
| 6,410,520 | B2 | 6/2002 | Cazer et al. | |
| 6,541,454 | B1 | 4/2003 | Breuer et al. | |
| 6,544,967 | B2 | 4/2003 | Daifotis et al. | |
| 6,548,042 | B2 * | 4/2003 | Arstad et al. | ............... 424/1.77 |
| 6,562,974 | B2 | 5/2003 | Cazer et al. | |
| 6,638,920 | B2 | 10/2003 | Thompson | |
| 6,696,427 | B1 | 2/2004 | Jomaa | |
| 6,753,324 | B2 | 6/2004 | Jomaa | |
| 6,984,400 | B2 | 1/2006 | Golomb et al. | |
| 7,008,645 | B2 | 3/2006 | Golomb et al. | |
| 7,358,361 | B2 | 4/2008 | Sanders et al. | |
| 7,425,549 | B2 | 9/2008 | Little et al. | |
| 7,560,490 | B2 | 7/2009 | Zanetti et al. | |
| 2002/0042539 | A1 | 4/2002 | Arstad et al. | |
| 2004/0087554 | A1 * | 5/2004 | Blum et al. | ............ 514/102 |
| 2005/0113331 | A1 * | 5/2005 | Prniak et al. | ............ 514/49 |
| 2006/0079487 | A1 | 4/2006 | Sanders et al. | |
| 2008/0255070 | A1 * | 10/2008 | Oldfield et al. | ............ 514/89 |
| 2008/0318906 | A1 | 12/2008 | Sanders et al. | |

FOREIGN PATENT DOCUMENTS

DE 3719513 A1 12/1988
DE 19738005 A1 3/1999

(Continued)

OTHER PUBLICATIONS

Martin et al., 2002, CAS: 137:134485.*
Martin et al., 2001, CAS: 134:292629.*
Lee et al., 2005, CAS: 142:349042.*
Ghosh et al., 2003, CAS: 140:138740.*
Ding et al., 2006, CAS: 145: 211178.*
Sanders et al., 2003, CAS:140:22647.*
Kotsikorou et al., 2003, CAS: 139:190645.*
Alfer'ev et al. (Aug. 1994) "Reactions of Vinylidenediphosphonic Acid with Nucleophiles. 5. Addition of Heterocyclic Amines and Trimethylamine to Vinylidenediphosphonic Acid," *Russian Chem. Bull.* 44(8):1528-1530.

(Continued)

*Primary Examiner*—Rei-tsang Shiao
(74) *Attorney, Agent, or Firm*—Greenlee, Winner and Sullivan, P.C.

(57) ABSTRACT

The invention provides, inter alia, novel bisphosphonate compounds and methods of making and using. In embodiments, the invention provides compounds and methods in connection with research and therapeutic applications, e.g., for tumor cell growth inhibition, activation of gammadelta T cells, inhibition of farnesyldiphosphate (FPPS) and/or undecaprenyldiphosphate synthase enzymes, bone resorption diseases, cancer, immune disorders, immunotherapy, and infectious diseases. In regards to certain embodiments, a surprising advance has been the recognition that certain structural features can significantly enhance the activity of the compounds. For example, the presence of particular cationic species e.g., phosphonium, sulfonium, and arsonium moieties can contribute to desirable functional activity when positioned near a bisphosphonate moiety. In other embodiments of non-nitrogen containing bisphosphonates, terphenyl and benzyl bisphosphonate compounds and methods are provided. Further variations are also provided.

19 Claims, 9 Drawing Sheets

FOREIGN PATENT DOCUMENTS

| | | |
|---|---|---|
| DE | 19859668 | 12/1999 |
| JP | 55098193 | 7/1980 |
| SU | 1022970 A1 | 6/1983 |
| WO | WO9420508 A1 | 9/1994 |
| WO | WO 95/34207 | 12/1995 |
| WO | WO 97/08178 | 3/1997 |
| WO | WO9712619 A1 | 4/1997 |
| WO | WO 00/03677 | 1/2000 |
| WO | WO 02/11704 A2 | 2/2002 |
| WO | WO 02/076515 | 10/2002 |
| WO | WO 03/021031 A2 | 3/2003 |
| WO | WO 03/075741 | 9/2003 |
| WO | WO 03/097655 | 11/2003 |
| WO | WO 2004/024165 | 3/2004 |
| WO | WO 2004/050096 | 6/2004 |
| WO | WO 2004/060327 | 7/2004 |
| WO | WO 2005/023270 | 3/2005 |
| WO | WO 2005/027842 | 3/2005 |
| WO | WO 2006/039721 | 4/2006 |
| WO | WO 2007/109585 | 9/2007 |
| WO | WO 2008/128056 | 10/2008 |

OTHER PUBLICATIONS

Alfer'ev et al. (1983) "Reactions of Vinylidenediphosphonic Acid with Nucleophiles. 1. Addition of Alipathic Amines," *Bull. Acad. Sci. USSR Div. Chem. Sci.* 32:2515-2518.

Alfer'ev et al. (1984) "Addition of Nucleophilic Agents to Vinylidenediphosphonic Acid. Communication 2. Reactions of Vinylidenediphosphonic Acid with Primary Amines, Ammonia, and Hydrazine," *Bull. Acad. Sci. USSR Div. Chem. Sci.* 33:1031-1035.

Amin et al. (1992) "Bisphosphonates Used for the Treatment of Bone Disorders Inhibit Squalene Synthase and Cholesterol Biosynthesis," *J. Lipid Res.* 33:1657-1663.

Amin. et al. (Aug. 1996) "1-Hydroxy-3-(methylpentylamino)-propylidene-1, 1-bisphosphonic Acid as a Potent Inhibitor of Squalene Synthase," *Arzneimittelforschung* 46:759-762.

Bergstrom et al. (2000) " Aledronate is a Specific, Nanomolar Inhibitor of Farnesyl Diphosphate Synthase," *Arch. Biochem. Biophys.* 373:231-241.

Blattman et al. (Jul. 2004) "Cancer Immunotherapy: A Treatment for the Masses," *Science* 305:200-205.

Body et al. (2004) "Oral Ibandrinate Improves Bone Pain and Preserves Quality of Life in Patients with Skeletal Metastases Due to Breast Cancer," *Pain* 111:306-312.

Bouzahzah et al. (Jun. 2005) "Risedronate in the Treatment of Murine Chagas' Disease," *Parasitol. Res.* 96:184-187.

Brunger et al. (1998) "Crystallography and NMR System: A New Software Suite for Macromolecular Structure Determination," *Acta Cryst. D. Biol. Cryst.* 54(5):905-921.

Bundgaard, H. (1991) "Design and Application of Prodrugs," In; *A Textbook of Drug Design and Development*, Krosgaard-Larsen et al. Eds., pp. 113-191.

Bundgaard, H. (1992) "Means to Enhance Penetration. (1) Prodrugs as a Means to Improve the Delivery of Peptide Drugs," *Adv. Drug. Deliv. Rev.* 8:1-38.

Bundgaard, H. (1985) "Design of Prodrugs," *Methods Enzymol.* 112:309-396.

Burke et al. (Feb. 2004) "Heteromeric Geranyl Diphosphate Synthase from Mint: Construction of a Functional Fusion Protein and Inhibition by Bisphosphonate Substrate Analogs," *Arch. Biochem. Biophys.* 422 (1):52-60.

Buxton et al. (2004) "Bisphosphonate-ciprofloxin Bound to Skelite is a Prototype for Enhancing Experimental Local Antibiotic Delivery to Injured Bone," *Br. J. Surg.* 91:1192-1196.

Cao et al. (2006) "[2-(3-Fluoropyridinium-1-yl)-1-hydroxy-1-phosphonoethyl]phosphonate," *Acta Cryst.* E62:o1003-o1005.

Cao et al. (2006) "[1-Hydroxy-1-phosphono-2-(trimethylphosphonium-1-yl)ethyl]phosphonate Monohydrate," *Acta Cryst.* E62:o1055-01057.

Caraglia et al. (2004) "The Farnesyl Transferase Inhibitor R115777 (Zarnestra) Synergistically Enhances Growth Inhibition and Apoptosis Induced on Epidermoid Cancer Cells by Zoledronic Acid (Zometa) and Pamidronate," *Oncogene* 23:6900-6913.

Cromartie et al. (1999) "The Discovery of a Novel site of Action for Herbicidal Bisphosphonates," *Pesticide Biochem. Phys.* 63:114-126.

Davisson et al. (1986) "Phosphorylation of Isoprenoid Alcohols," *J. Org. Chem.* 51:4768-4779.

Dawson et al. (2003) "Therapeutic Benefit of Bisphosphonates in the Management of Prostate Cancer-Related Bone Disease," *Exp. Opin. Pharmacother.* 4:705-716.

De Cock et al. (2005) "Cost-Effectiveness or Oral Ibandronate Versus IV Zoledronic Acid or IV Pamidronate for Bone Mestastases in Patients Receiving Oral Hormonal Therapy for Breast Cancer in the United Kingdom," *Clin. Ther.* 27(8):1295-1310.

Dickson et al. (Aug. 2006) "Efficacy of Zoledronate Against Neutoblastoma," *Surgery* 140:227-235.

Dunford et al. (2001) "Structure-Activity Relationships for Inhibition of Farnesyl Diphosphate Synthase in Vitro and Inhibition of Bone Resorption in ViVi by Nitrogen-Containing Bisphosphonates," *J. Pharmacol. Exp. Ther.* 296:235-242.

Fisher et al. (1999) "Alendronate Mechanism of Action: Geranylgeraniol, an Intermediate in the mevalonate Pathway, Prevents Inhibition of Osteoclast Formation, Bone Resorption, and Kinase Activation in Vitro," *Proc. Nat. Acad. Sci. USA* 96:133-138.

Forsea et al. (2004) "Nitrogen-Containing Bisphosphonates Inhibit Cell Cycle Progression in Human Melanoma Cells," *Br. J. Cancer* 91:803-810.

Gabelli et al. (Jan. 2006) "Structure and Mechnism of the Farnesyl Diphosphate Synthase from *Trypanosoma cruzi*: Implications for Drug Design," *Proteins* 62:80-88.

Garzoni et al. (2004) "Antiparasitic Activity of Risedronate in a Murine Model of Acute Chagas' Disease," *Int. J. Antimicrobial Agents* 23:286-290.

Garzoni et al. (2004) "Selective in Vitro Effects of the Farnesyl Pyrophosphate Synthase Inhibitor Risedronate on *Trypanosome Cruzi,*" *Int. J. Antimicrobial Agents* 23:273-285.

Gedeck et al. (2006) "QSAR-How Good is it in Practice? Comparison of Descriptor Sets on an Unbiased Cross Section of Corporate Data Sets," *J. Chem. Inf. Model* 46(5):1924-1936.

Ghosh et al. (2004) "Effects of Bisphosphonates on the Growth of Entamoeba Histolytica and Plasmodium Species in Vitro and in Vivo," *J. Med. Chem.* 47:175-187.

Gober et al. (Jan. 2003) "Human T Cell Receptor γδ Cells Recognize Endogenous Mevalonate Metabolites in Tumor Cells," *J. Exp. Med.* 197:163-168.

Goffinet et al. (2006) "Zoledronic Acid Treatment Impairs Protein Gerabyl-Geranylation for Biological Effects in Prostatic Cells," *BMC Cancer* 6:60-.

Goldstein et al. (1990) "Regulation of the Mevalonate Pathway," *Nature* 343:425-.

Gordon, D.H. (2005) "Efficacy and Safety of Intravenous Bisphosphonates for patients with Breast Cancer Metastic to Bone: A review of Randomized, Double-Blind Phase III Trials," *Clin. Breast Cancer* 6(2):125-131.

Green, J.R. (2004) "Bisphosphonates: Preclinical Review," *The Oncologist* 9(supp 4):3-13.

Green et al. (Apr. 2001) "Chemical and Biological Prerequisites for Novel Bisphosphonate Molecules: Results of Comparative Preclinical Studies," *Sem. Oncol.* 28(2 Supp 6):4-10.

Green et al. (2005) "Skeletal Complications of Prostate Cancer: Pathophysiology and Therapeutic Potential of Bisphosphonates," *Acta Oncol.* 44:282-292.

Grove et al. (2000) "The Intracellular Target for the Antireorptive Aminobisphosphonate Drugs in *Dictyostelium discoideum* is the Enzyme Farnesyl Disphosphate Synthase," *J. Bone Miner. Res.* 15:971-981.

Guo et al. (Jun. 2007) "Bisphosphonates Target Multiple Sites in Both *Cis-* and *Trans-*Prenyltransferases: A Crystallographic Investigation,".

Heidenreich et al. (2004) "Ibandronate in Metastic Bone Pain," *Semin. Oncol.* 31(5 supp; 10):67-72.

Herczegh et al. (2002) "Osteoadsorptive Bisphosphonate Derivatives of Fluoroquinolone Antibacterials," *J. Med. Chem.* 45:2338-2341.

Hopkins et al. (Feb. 2006) "Can We Rationally Design Promiscuous Drugs," *Curr. Opin. Struct. Biol.* 16:127-136.

Hosfield et al. (Mar. 2004) "Structural Basis for Bisphosphonate-Mediated Inhibition of Isoprenoid Biosynthesis," *J. Biol. Chem.* 279:8526-8529.

Hudock et al. (2006) "1-Hydroxy-1-phosphono-2-(trimethylarsonium-1-yl_ethanephosphonate Monohydrate," *Acta Cryst.* E62:o843-o845.

Inoue et al. (2003) "New Synthesis of Gem-Bis(phosphono)ethylenes and their Applications," *Synthesis* 13:1971-1976.

Jagdev et al. (2001) "The Bisphosphonate, Zoledronic Acid, Induces Apoptosis of Breast Cancer Cells: Evidence for Synergy with Paclitaxel," *Br. J. Cancer* 84:1126-1134.

Jones et al. (1991) "Improved Methods for Building Protein Models in Electron Density Maps and the Location of Errors in These Models," *Acta Cryst A.* 47:110-119.

Kato et al. (2001) "Targeting of Tumor Cells for Human Gammadelta T Cells by Nonpeptide Antigens," *J. Immunol.* 167:5092-5098.

Kavanagh et al. (May 2006) "The Crystal Structure of Human Geranylgeranyl Pyrophosphate Synthase Reveals a Novel Hexameric Arrangement and Inhibitory Product Binding," *J. Biol. Chem.* 281:22004-22012.

Kavanagh et al. (2006) "The Molecular Mechanism of Nitrogen-Containing Bisphosphonates as Antiosteoporosis Drugs," *Proc. Nat. Acad. Sci. USA* 103(20):7829-7834.

Keller et al. (1999) "Mechanism of Aminobisphosphonate Action: Characterization of Alendronate Inhibition of the Isoprenoid Pathway," *Biochem. Biophys. Res. Commun.* 266:560-563.

Kieczykowski et al. (1995) "Preparation of (4-amino-1-hydroxybutylidene) Bisphosphonic and Sodium Salt, MK0217 (alendronate sodium). An Improved Procedure for the Preparation of 1-Hydroxy-1, 1-Bisphosphonic Acids," *J. Org. Chem.* 60:8310-8312.

Klebe et al. (1994) "Molecular Similarity Indices in a Comparative Analysis (CoMSIA) of Drug Molecules to Correlate and Predict Their Biological Activity," *J. Med. Chem.* 37(24):4130-4146.

Kotsikorou et al. (2003) "A Quantitative Structure-Activity Relationship and Pharmacophore Modeling Investigation of Aryl-X and Heterocyclic Bisphosphonates as Bone Resorption Agents," *J. Med. Chem.* 46(14):2932-2944.

Kotsikorou et al. (2005) "Bisphosphate Inhibition of the Exopolyphosphatase Activity of the *Typanosoma brucei* Soluble Vacuolar Pyrophosphatase," *J. Med. Chem.* 48:6128-6139.

Krapcho et al. (1998) "Synthesis of Regioisomeric Difluoro- and 8-CHloro-9-fluorobenz[g]isoquinoline-5, 10-diones and SNAr Displacements Studies by Diamines: bis(aminoalkyl)aminobenz[g]isoquinoline-5, 10-diones," . *Flurine Chem.* 90:139-147.

Kunzmann et al. (2000) "Stimulation of γδ T Cells by Aminobisohosphonates and Induction of Antiplasma Cell Activity in Multiple Myeloma," *Blood* 96:384-392.

Lecouvey et al. (2001) "A Mild and Efficient One-Pot Synthesis of 1-hydroxymethylene-1, 1-bisphosphonic Acids. Preparation of New Tripod Ligands," *Tetrahedron Lett.* 42:8475-8478.

Leon et al. (Dec. 2006) "Isoprenoid Biosynthesis as a Drug Target: Bisphosphonate Inhibition of *Escherichia coli* K12 Growth and Synergistic Effects of Fosmidomycin," *J. Med. Chem.* 49:7331-7341.

Liang et al. (2002) "Structure, Mechanism and Function of Prenyltransferases," *Eur. J. Biochem.* 269:3339-3354.

Luckman et al. (1998) "Nitrogen-Containing Bisphosphonates Inhibit the Mevalonate Pathway and Prevent Post-Translational Prenylation of GTP-Binding Proteins, Including Ras.," *J. Bone Miner. Res.* 13:581-589.

Mancini et al. (Sep. 2004) "Efficacy and Safety of Ibandrinate in the Treatment of Opiod-Resistant Bone Pain Associated With Metastic Bone Disease: A Pilot Study,".

Mao et al. (2006) "Solid-State NMR, Crystallographic, and Computational Investigation of Bisphonphonates and Farnesyl Diphosphate Synthase-Bisphosphonate Complexes," *J. Am. Chem. Soc.* 128(45):14485-14497.

Mao et al. (2004) "Crystallization and Preliminary X-ray Diffraction Study of the Farnesyl Diphosphate Synthase from *Trypanosoma brucei*," *Acta Cryst D. Ciol. Cryst.* 60(10:1963-1866.

Martin et al. (2001) "Bisohosphonates Inhibit the Growth of *Typanosoma Brucei, Typanosoma cruzi, Leishmania donovani, Toxoplasma gondii*, and *Plasmodium falciparum*: A Potential Route to Chemotherapy." *J. Med. Chem.* 44:909-916.

Martin et al. (2002) "Activity of Bisphosphonates Against *Trypanosoma Brucei* rhodesiense," *J. Med. Chem.* 45:2904-2914.

Matin et al. (1999) "Nitrogen-Containing Bisphosohonates as Varbocation Transition State Analogs for Isoprenoid Biosynthesis," *Biochem. Biophys. Res. Commun.* 263:754-758.

Miyaura et al. (1981) "The Palladium-Catalyzed Cross-Coupling Reaction of Phenylboronic Acid with Haloarenes in the Presence of Bases," *Synth. Commun.* 11:513-519.

Mönkkonen et al. (Feb. 2006) "A New Endogenous ATP Analog (Apppl) Inhibits the Mitochondiral Adenine Nucleotide Translocase (ANT) and is Responsible for the Apoptosis Induced by Nitrogen-Containing Bisphosphonates," *Br. J. Pharmacol.* 147:437-445.

Montalvetti et al. (2001) "Bisphosphonates are Potent Inhibitors of *Trypanosoma cruzi* Farnesyl Pyrophosphate Synthase," *J. Biol. Chem.* 276:33930-33937.

Montalvetti et al. (May 2003) "Farnesyl Pyrophosphate Synthase Is and Essential Enzyme in *Tryanosoma brucei*," *J. Biol. Chem.* 278:17075-17083.

Moreno et al. (2001) "$^{31}$P NMR of Apicomlexans and the Effects of Risedronate on Cryptosporidium Parvum Growth," *Biochem. Biophys. Res. Commun.* 284:632-637.

Namaka et al. (2004) "A Treatment Algorithm for Neuropathic Pain," *Clin. Ther.* 26(7):951-979.

Navaza, J. (1994) "AMoRe: An Automated Package for Molecular Replacement," *Acta Cryst A.* 50:157-163.

Nielsen et al. (1988) "Glycolamide Esters as Bioable Prodrugs of Carboxylic Acid Agents: Synthesis of Stability, Bioconversion ad Physicochemical Properties," *J. Pharmaceutical Sci.* 77(4):285-298.

Norgrady (1985) *Medicinal Chemistry A Biochemical Approach*, Oxford University Press, New York, pp. 388-392.

Ortmann et al. (2003) "Acyloxyalkyl Ester Prodrugs of FR900098 with Improved in Vivo Anti-Malarial Activity," *Bioorganic Med. Chem. Lett.* 13:2163-2166.

PCT International Search Report, Corresponding to International Application No. PCT/US05/36425, Mailed May 2, 2006.

Reinholz et al. (2002) "Distinct Mechanisms of Bisphosphonate Action Between Osteoblasts and Breast Cancer Cells: Identity of a Patent New Bisphosphonate Analogue," *Br. Cancer Res.* 71:257-268.

Roberts et al. (May 1998) "Characterization of the Antimonial Antileishmanial Agent Meglumine Antimonate (Glucantime)," *Antimicrobial Agents Chemother.* 42(5):1076-1082.

Rodroguez et al. (2002) "Radical Cure of Experimental cutaneous Leishmaniasis by the Bisphosphonate Pamidronate," *J. Infect. Dis.* 186:138-140.

Roelofs et al. (Oct. 2006) "Molecular Mechanisms of Action of Bisphosphonates: Current Status," *Clin. Cancer Res.* 12:6222s-6230s.

Rogers et al. (1994) "Inhibitory Effects of Bisphosphonaters on Growth of Amoebae of the Cellular Slimie Mold *Dictyostelium discoideum*," *J. Bone Miner. Res.* 9:1029-1039.

Rondeau et al. (Feb. 2006) "Structural Basis for the Exeptional in Vivo Efficacy of Bisphosphonate Drugs," *ChemMedChem.* 1:267-273.

Rosen et al. (2004) "Zolendronic Acid is Superior to Pamidronate for the Treatment of Bone Metastases in Breast Carcinoma Patients with at Least One Osteolytic Lesion," *Cancer* 100:36-43.

Russell et al. (Apr. 2006) "From Bench to Bedside," *Ann. NY Acad. Sci* 1068:367-401.

Saiki et al. (Nov. 2005) "Characterization of Solanesyl and Decaprenyl Diphosphate Synthases in Mice and Humnas," *FEBS J.* 272:5606-5622.

Salomo et al. (2003) "How Myeloma Cells Escape Bisphosphonate-Mediated Killing: Development of Specific Resistance with Preserved Sensitivity to Conventional Chemotherapeutics," *Br. J. Haematol.* 122:202-210.

Sambrook et al. (2004) "Alendronate Produces Greater Effects than Raloxifene on Bone Density and Bone Turnover in Postmenopausal Women with Low Bone Density: Results of EFFECT (Efficacy of FOSAMAX versus EVISTA Comparison Trial)," *Int J. Intern. Med.* 255:503-511.

Sanders et al. (2003) "3-D QSAR Investigators of the Inhibition of Leishmania Major Farnesyl Pyrophosphate Synthase by Bisphosphonates," *J. Med Chem.* 46:5171-5183.

Sanders et al. (2004) "Quantitative Structure-Activity Relationships for Gammadelta T Cell Activation by Bisphosphonates," *J. Med. Chem.* 47:375-384.

Sanders et al. (2005) "Pyridium-1-yl Bisphosphonates are Potent Inhibitors of Farnesyl Diphosphate Synthase and Bone Resorption," *J. Med. Chem.* 48:2957-2963.

Santini et al. (Jun. 2006) "Mechanisms of Disease: Preclinical Reports of Antineoplastic Synergistic Action of Bisphosphonates," *Nat. Clin. Pract. Oncol.* 3:325-338.

Sheldrick et al. (1997) "SHELXL: High Resolution Refinement," *Methods Enzymol.* 277:319-343.

Song et al. (2004) "Synthesis of Chiral Phosphantigens and Their Activity in γδ T Cell Stimulation," *Bioorg. Med. Chem.* 14(17):4471-4477.

Swanson et al. (2006) "Anti-Cancer Therapy: Targeting the Mevalonate Pathway," *Curr. Cancer Drug Targets* 6:15-37.

Szabo et al. (2002) "Inhibition of Geranylgeranyl Diphosphate Synthase by Bisphosphonates and Diphosphates: A Potential Route to New Bone Antiresorption and Antiparasitic Agents," *J. Med. Chem.* 45(11):2185-2196.

Tanaka et al. (May 1995) "Natural and Synthetic Non-Peptide Antigens Recognised by Human γδ T Cells," *Nature* 375:155-158.

Thompson et al. (2004) "Statins Prevent Bisphosphonate-Induced Gammadelta-T-Cell Proliferation and Activation in Vitro," *J. Bone Miner. Res.* 19:278-288.

Tripathy et al. (Dec. 2004) "Review of Ibandronate in the Treatment of Metastatic Bone Disease: Experience from Phase III Trials," *Clin. Ther.* 26(12):1947-1959.

van Beek et al. (2003) "Differentiating the Mechanisms of Antiresorptive Action of Nitrogen Containing Bisphosphonates," *Bone* 33:805-811.

van Beek et al. (1999) "The Role of Geranylgeranylation in Bone desorption and It's Suppression by Biphosphonates in Fetal Bone Explants in Vitro: A Clue to the Mechanism of Action of Nitrogen-Containing Bisphosphonates," *J. Bone Miner. Res.* 14:722-729.

van Beek et al. (1999) "Nitrogen-Containing Biphosphonates Inhibit Isopentenyl Pyrophosphate Isomerase/farnesyl Pyrophosphate Synthase Activity with Relative Potencies Corresponding to their Antiresorptive Potencies in Vitro and in Vivo," *Biochem. Biophys. Res. Commun.* 255:491-494.

van Beek et al. (1999) "Farnesyl Pyrophosphate Synthase is the Molecular Target of Nitrogen-Containing Bisphosphonates," *Biochem. Biophys. Res. Commun.* 264:108-111.

Vasireddy et al. (2003) "Patterns of Pain in Paget's Disease of Bone and their Outcomes on Treatment with Pamidrinate," *Clin. Rheumatol.* 22:376-380.

Vepsalainen, J.J. (1999) "Bisphosphonate Prodrugs: A New Synthetic Strategy to Tetraacyloxymethyl Esters of Methyl-lenebisphosphonates," *Tetrahedron Lett.* 40:8491-8493.

Wakchoure et al. (May 2006) "Bisphosphonates Inhibit the Growth of Mesothelioma Cells In Vitro and In Vivo," *Clin. Cancer Res.* 12:2862-.

Wang et al. (2001) "Antibacterial effect of Human Vgamma2Vdelta2 T Cells in Vivo," *J. Clin. Invest.* 108:1349-1357.

Weizman et al. (1999) "Pharmacological Interaction of the Calcium Channel Blockers Verapamil and Flunarizine with the Opiod System," *Brain Res.* 818:187-195.

Weimer et al. (2007) "Digeranyl Bisphosphonate Inhibits Geranylgeranyl Pyrophooosphate Synthase," *Biochem. Biophys. Res. Commun.* 353:921-925.

Widler et al. (Aug. 2002) "Highly Potent Geminal Bisphosphonates. From Pamidronate Disodium (Aredia) to Zoledronic Acid (Zometa)," *J. Med. Chem.* 45(17):3721-3738.

Wildman et al. (1999) "Prediction of Physicochemical Parameters by Aromic Contributions," *J. Chem. Info. Comp. Sci.* 39:868-873.

Wilhelm et al. (2003) "γδT Cells for Immune Therapy of Patients with Lymphoid Malignancies," *Blood* 102:200-206.

Yamagishi et al. (Dec. 2004) "Minodronate, A Newly Developed Nitrogen-Containing Bisphosphonate, Suppresses Melanoma Growth and Improves Survival in Nude Mice by Blocking Vascular Endothelial Growth Factor Signaling," *Am. J. Pathol.* 165:1865-1874.

Yardley et al. (2002) "In Vivo Activities of Farnesyl Pyrophosphate Synthase Inhibitors Against *Leishmania donovani* and *Toxoplasma gondii*," *Antimicrob. Agents Chemother.* 46:929-931.

Yin et al. (Mar. 2006) "Enthalpy Versus Entropy-Driven Binding of Bisphosphonates to Farnesyl Diphosphate Synthase," *J. Am. Chem. Soc.* 128:3524-3525.

Zhang et al. (2000) A Novel and Practical Synthesis of 3-Unsubstituted Indolizines, *Synthesis* :1733-1737.

Zhang et al. (2006) "[2-(Dimethylsulfonio)-1-hydroxy-1-phosphonoethyl]Phosphonate Monohydrate," *Acta Cryst.* E62:o1006-o1008.

Zhang et al. (Sep. 2006) "Activity of Nitrogen-Containing and Non-Nitrogen-Containing Bisphosphonates on Tumor Cell Lines," *J. Med. Chem.* 49(19):5804-5814.

Zhu (2001) "3D QSAR Analyses of Novel Tyrosine Kinase Inhibitors Based on Pharmacophore Alignment," *J. Chem. Inf. Comput. Sci.* 41(4):1032-1040.

International Search Report and Written Opinion, International Application No. PCT/US07/64239, Aug. 21, 2008, 5pages.

Alfer'ev et al. (1987) "Reactions of Vinylidenediphosphonic Acid with Nucleophiles. 3. Addition of Thiols," *Russian Chem. Bull.* 36(4):786-790.

Alfer'ev et al. (1984) "New Bifunctional Reagents for the Study of Cyctochrome P450 Active Center Localization in Microsomal Membrane," *Doklady Akademii Nauk SSSR* 277(2):371-374 Abstract Only.

Chen et al. (2008) "Inhibition of Geranylgeranyl Diphosphate Synthase by Bisphosphonates: A Crystallographic and Computational Investigation" *J. Med. Chem.* 51:5594-5607.

Cohen et al. (1999) "Synthesis and Preclinical Pharmacology of 2-(20Aminopyrimidinio) Ethylidene-1, 1-Bisphosphonic Acid Betaine (ISA-13-1)—A Novel Bisphosphonate," *Pharmaceutical Res.* 16(9):1399-1406.

Cohen et al. (1998) "Bisphosphonates and Tetracycline: Experimental Models for their Evaluation in Calcium-Related Disorders," *Pharma. Res.* 15(4):606-613.

Desouki et al. (Dec. 2005) "Cross Talk Between Mitochondria and Superoxide Generating NADPH Oxidase in Breast and Ovarian Tumors," *Cancer Biol. Ther.* 4(12):1367-1373.

Gossman et al. (2003) "Three Hydrates of the Bisphosphonate Risedronate, Consisting of One Molecular and Two Ionic Structures," *Acta Crystallographica Section C* (Crystal Structure Comm.) C59:m33-m36.

Gossman et al. (2002) "Monosodium [1-hydroxy-2-(1H-imidazol-3-ium-4-yl)ethane-1,1-diyl]-bis(phosphonate) tetrahydrate (monosodium isozoledronate)," *Acta Crystallographica Section C* (Crystal Structure Comm.) C58:m599-m600.

Halgren et al. (1996) "The Merck Molecular Force Field. Bridging the Gap—From Small Organics to Proteins," *Abst. Papers Am. Chem. Soc.* 211:70.

Hutchinson et al. (1988) "Michael Addition Reactions of ethylidenebisphosphonates," *J. Organometall. Chem.* 346(3):341-348.

Inoue et al. (Sep. 15, 2005) "Effect of Combination Therapy with a Novel Bisphosphonate, Minodronate (YM529), and Docetaxel on a Model of Bone Metastasis by Human Transitional Cell Carcinoma," *Clin. Cancer Res.* 11(18):6669-6677.

Klein et al. (1998) "Structurally Different Bisphosphonates Exert Opposing Effects on Alkaline Phosphate and Mineralization in Marrow Osteoprogenitors," *J. Cell. Biochem.* 68:186-194.

Krainev et al. (1992) "Effect of Mutations at Lys250, Arg251, and Lys253 of Cytochrome P450 1A2 on the Catalytic Activities and the Bindings of Bifunctional Axial Ligands," *Arch. Biochem. Biophy.* 298(1):198-203.

Krainev et al. (1988) "Use of Bifunctional Compounds for Studying the Active Center Location of Cytochrome P450 in a Microsomal Membrane," *Biologicheskie Membrany* 5(8):795-806 Abstract Only.

Krainev et al. (1988) "Localization of the Active Center of Microsomal Cytochrome P-450," *Biochem Biophy. Research Comm.* 150(1):426-35.

Krainev et al. (1985) "Bifunctional Compound Study of the Active Center Location of Cytochrome P-450 in a Microsomal Membrane ('float' molecules method)," *Biochimica Biophysica Acta Biomembranes* 818(1):96-104.

Kubo et al. (2007) "Efficacy of a Nitrogen-Containing Bisphosphonate, Minodronate, in Conjunction with a p38 Mitogen Activated Protein Kinase Inhibitor or Docorubicin Against Malignant Bone Tumor Cells," *Cancer Chemother. Pharmacol.* 62(1):111-116.

Kubo et al. (Jun. 2006) "Inhibitory Effects of a New Bisphosphonate, Minodronate, on Proliferation and Invasion of a Variety of Malignant Bone Tumor Cells," *J. Orthop. Res.* 24:1138-1144.

Leon et al. (Dec. 14, 2006) "Isoprenoid Biosynthesis as a Drug Target: Bisphosphonate Inhibition of *Escherichia coli* K12 Growth and Synergistic Effects of Fosmidomycin," *J. Med. Chem.* 49:7331-7341.

Ling et al. (2005) "Bisphosphonate Inhibitors of *Toxoplasma gondi* Growth: In Vitro, QSARm and in Vivo Investigations," *J. Med. Chem.* 48:3130-3140.

Martin, M.B. et al. (1999) "Nitrogen-Containing Bisphosphonates as carbocation Transition State Analogs for Isoprenoid Biosynthesis," Biochem. Biophys. Research Comm. 263:754-758, see p. 757, second column, first full paragraph.

Medical News Today, Jul. 15, 2006) "Application Filed for the Osteoporosis Treatment ONO-5920/YM529 in Japan," http://www.medicalnewstoday.com/articles/47369.php.

Miyaura et al. (1981) "The Palladium-Catalyzed Cross-Coupling Reaction of Phenylboronic Acid with Haloarenes in the Presence of Bases," *Synth. Commun* 11:513-519.

Press, W.H. (1988) "Variable Metric Methods in Multidimensions," In; *Numerical Recopies in C: The Art of Scientific Computing*, Cambridge University Press: New York, pp. 324-328.

Segawa et al. (Apr. 2005) "The Anti-Leukemic Efficacy of the Third Generation Bisphosphonate ONO5920/YM529," *Leuk. Res.* 29(4):451-457.

Van Brussel et al. (2003) "Hydronium (cycloheptylammonio)-methylene-1,1-bisphosphonate (hydronium incadronate)," *Acta Crystallographica Section C* (Crystal Structure Comm.) C59:o93-o94.

Zhang et al. (Mar. 2009) Lipophilic Bisphosphonates as Dual Farnesyl/Geranylgeranyl Diphosphate Synthase Inhibitors: An X-ray and NMR Investigation, *J. Amer. Chem. Soc.* 131:5153-5162.

Zhang et al. (Oct. 2007)"Activity of Sulfonium Bisphosphonates on Tumor Cell Lines," *J. Med. Chem.* 50:6067-6079.

Miwa et al. (Oct. 1, 2005) "The Bisphosphonate YM529 Inhibits Osteolytic and Osteoblastic Changes and CXCR-4-Induced Invasion in prostate Cancer," *Cancer Res.* 65(19):8818-8825.

\* cited by examiner

BISPHOSPHONATE COMPOUNDS AND METHODS

CROSS-REFERENCES TO RELATED APPLICATIONS

This application is a nonprovisional application claiming the benefit of U.S. Application Ser. No. 60783491 filed Mar. 17, 2006.

STATEMENT REGARDING FEDERALLY SPONSORED RESEARCH OR DEVELOPMENT

This invention was made, at least in part, with government support under Grant Nos. GM50694, GM65307, GM73216, and AI-060452 awarded by the National Institutes of Health. The government has certain rights in the invention.

BACKGROUND OF THE INVENTION

Earlier generation compounds of nitrogen-containing bisphosphonates such as pamidronate (Aredia®), alendronate (Fosamax®), risedronate (Actonel®), zoledronate (Zometa®), and ibandronate (Boniva) represent important drugs currently used to treat conditions such as osteoporosis, Paget's disease and hypercalcemia due to malignancy. These compounds function primarily by inhibiting the enzyme farnesyl diphosphate synthase (FPPS), resulting in decreased levels of protein prenylation in osteoclasts. Certain bisphosphonates have also been found to have anti-parasitic activity and to stimulate human γδ T cells, and there is interest in cancer-related applications. There is continued interest, however, in the further development of alternative bisphosphonate compounds and methods of use such as therapeutic applications.

There have been reports regarding the significance of certain nitrogen-containing groups in the context of active bisphosphonate compounds. See US Publication 20060079487 and PCT Publication WO/2006/039721. The present invention discloses the fact that, remarkably, bisphosphonates lacking certain nitrogen-containing groups but containing instead aryl, substituted aryl, sulfonium and phosphonium groups have activity in killing cancer cells, in inhibiting the enzyme farnesyl diphosphate synthase from humans as well as from *Trypanosoma brucei* (the causative agent of African sleeping sickness), in stimulating gamma delta T cells in the human immune system, as well as acting as inhibitors of the enzyme undecaprenyl diphosphate synthase, essential for cell wall biosynthesis in many pathogenic bacteria such as *Escherichia coli* and *Staphylococcus aureus*. As such, these novel compounds are of interest in the context of the treatment of cancer, bone resorption diseases and infectious diseases caused by bacteria and protozoa.

SUMMARY OF THE INVENTION

The invention provides, inter alia, novel bisphosphonate compounds and methods of making and using. In embodiments, the invention provides compounds and methods in connection with research and therapeutic applications, e.g., for tumor cell growth inhibition, activation of gammadelta T cells, inhibition of farnesyldiphosphate (FPPS) and/or undecaprenyldiphosphate synthase enzymes, bone resorption diseases, cancer, immune disorders, immunotherapy, and infectious diseases. In regards to certain embodiments, a surprising advance has been the recognition that certain structural features can significantly enhance the activity of the compounds. For example, the presence of particular cationic species e.g., phosphonium, sulfonium, and arsonium moieties can contribute to desirable functional activity when positioned near a bisphosphonate moiety. In other embodiments of non-nitrogen containing bisphosphonates, terphenyl and benzyl bisphosphonate compounds and methods are provided. Further variations are also provided.

Without wishing to be bound by any particular theory, there can be discussion herein of beliefs or understandings of underlying principles or mechanisms relating to the invention. It is recognized that regardless of the ultimate correctness of any mechanistic explanation or hypothesis, an embodiment of the invention can nonetheless be operative and useful.

In embodiments, bisphosphonate compounds of the invention can demonstrate activity in one or more contexts, including a farnesyl diphosphate synthase (FPPS) assay, a UPPS assay, a *D. discoideum* growth inhibition assay, a T cell activation assay, a bone resorption assay, the treatment of infectious disease, the treatment of a bone resorption clinical disorder, an immunotherapeutic treatment, the treatment of cancer, and the treatment of bone pain.

The invention broadly provides bisphosphonate compounds and related methods of making and using. In embodiment, the invention specifically provides bisphosphonate compounds with either a sulfonium group, a phosphonium group, an arsonium group, a substituted aromatic group, in addition to a bisphosphonate group (and/or a pharmaceutically acceptable salt or ester group). In further embodiments, the invention specifically provides other variations of bisphosphonate compounds. In embodiments, functionally and/or therapeutically active bisphosphonates of this invention have general and specific structures as described herein.

In an embodiment, the invention provides a compound having the general structural formula BX1:

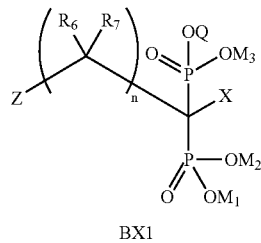

BX1 where:
Q=M or

⊖

(negative charge);
Z=cationic or neutral species
  cationic Z are:

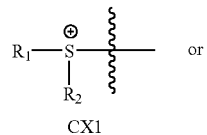  or

CX1

-continued

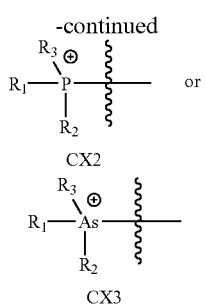

neutral Z are:

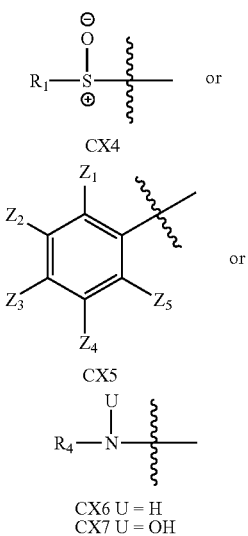

CX6 U = H
CX7 U = OH and salts, esters and hydrates thereof
wherein:
Q is M or a negative charge;
M, $M_1$, $M_2$ or $M_3$, independently of one another are H, alkyl, —$(CH_2)_p$—O—CO—R or —$(CH_2)_p$—O—C—R where p is 1 to 6, R is H, optionally substituted alkyl or optionally substituted aryl; $M_1$, $M_2$ or $M_3$ which are hydrogen may also be in form of a salt (—O—$A^+$, where $A^+$ is a cation);
X is H, halogen, OH or methyl;
n is 1, 2, or 3;
$R_6$ and $R_7$, independently of each other and other $R_6$ and $R_7$ in the compound, are selected from the group consisting of a hydrogen, a halogen, a —$N(R)_2$, or —SR group, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group where $R_6$ and $R_7$ can be linked together to form a 4-7 member ring;
U is H or OH;
$R_1$, $R_2$, $R_3$ and $R_4$, independently of one another, are selected from the group consisting of an optionally substituted alkyl group, an optionally substituted alkenyl group, an optionally substituted alkoxy group, and an optionally substituted aryl group wherein any two $R_1$-$R_3$ groups in the same molecule can be linked together to form a 4-7 member ring; and $Z_1$-$Z_5$, independently of one another, are selected from the group consisting of a hydrogen, a halogen, a —CN, —OR, —COOR, —OCOOR, —COR, —$CON(R)_2$, —$OCON(R)_2$, —$N(R)_2$, —$NO_2$, —SR, —$SO_2R$, —$SO_2N(R)_2$ or —SOR group, an optionally substituted alkyl group, an optionally substituted alkenyl group, an optionally substituted alkynyl group and an optionally substituted aryl group, where each R, independent of any other R in any listed group, is selected from H, an optionally substituted alkyl group, an optionally substituted aryl group, and an optionally substituted acyl group wherein any two Z groups substituted on adjacent carbons of the ring can be linked together to form a 4-7 member ring which may contain one or more double bonds, be aromatic and/or contain one or more heteroatoms (e.g., S, O or N).

In an embodiment, the Z is cationic Z and comprises the sulfonium group CX1. In an embodiment, the Z is cationic Z and comprises the phosphonium group CX2. In an embodiment, the Z is cationic Z and comprises the arsonium group CX3. In an embodiment, X=H. In an embodiment, X=OH. In an embodiment, a compound of the invention excludes a compound described herein for a structure designated CX1A, CX2A, and/or CX3A; regardless of hydration state for such compounds. In an embodiment, the Z is neutral Z and comprises the CX4 group. In an embodiment, the Z is neutral Z and comprises the CX5 group. In an embodiment, the Z is neutral Z and comprises group CX6 or CX7.

In an embodiment, the invention provides a compound selected from the group consisting of: 491, 493, 494, 495, 496, 498, 608, 618, 621, 622, 623, 624, 625, 626, 628, 629, 640, 647,648; 527, 536, 540,541, 546, 547, 550, 564, 569, 572, 573, 574, 575, 576, 580, 581, 584, 585, 587, 589, 594, 560, 571; and for each respective said compound, a pharmaceutically acceptable salt or ester thereof. In an embodiment, said compound is also a compound of formula BX1.

In an embodiment, the invention provides a composition comprising a pharmaceutical formulation of a compound of the invention.

In an embodiment, the invention provides a method of treating a bone resorption disorder comprising administering to a patient in need thereof, a therapeutically effective amount of a compound of the invention or a pharmaceutical formulation thereof.

In an embodiment, the invention provides a method of treating a cancer comprising administering to a patient in need thereof, a therapeutically effective amount of a compound of the invention or a pharmaceutical formulation thereof. In an embodiment, the cancer is breast cancer. In an embodiment, the breast cancer involves an actual or potential bone metastatic condition.

In an embodiment, the invention provides a method of treating a bone pain condition comprising administering to a patient in need thereof, a therapeutically effective amount of a compound of the invention or a pharmaceutical formulation thereof.

In an embodiment, the invention provides a method of treating an infectious disease comprising administering to a patient in need thereof, a therapeutically effective amount of a compound of the invention or a pharmaceutical formulation thereof. In an embodiment, said infectious disease relates to an agent selected from the group consisting of: a virus, a fungus, a bacterium, and a protozoan parasite. In an embodiment, said virus is a retrovirus. In an embodiment, said retrovirus is human immunodeficiency virus (HIV). In an embodiment, said protozoan parasite is selected from the group consisting of: *Leishmania, Toxoplasma, Cryptosporidium, Plasmodium,* and *Trypanosoma*. In an embodiment, said protozoan parasite is *Leishmania major*. In an embodiment, said bacterium is *Escherichia coli* or *Staphylococcus aureus*.

In an embodiment, the invention provides a method of immunotherapeutic treatment comprising administering to a patient in need thereof, a therapeutically effective amount of a compound of the invention or a pharmaceutical formulation thereof. In an embodiment, the invention provides a method of stimulating a T cell, comprising contacting the T cell with a compound of the invention or a pharmaceutical formulation thereof. In an embodiment, said T cell is a gammadelta T cell.

In an embodiment, the invention provides a method of synthesizing a compound of the invention or a pharmaceutical formulation thereof.

In an embodiment, the invention provides a method of inhibiting growth of an infectious disease agent comprising contacting said infectious disease agent with an effective amount of a compound of the invention or a pharmaceutical formulation thereof.

In an embodiment, the invention provides a method of inhibiting growth of a cancer cell comprising contacting said cancer cell with an effective amount of a compound of the invention or a pharmaceutical formulation thereof.

In specific embodiments, alkyl, alkenyl, alkynyl and aryl groups of the variables of the above formula are optionally substituted with one or more non-hydrogen substituent groups selected from halogens, —CN, —OR', —COOR', , —OCOOR', —COR', —CON(R')$_2$, —OCON(R')$_2$, —N(R')$_2$, —NO$_2$, —SR', —SO$_2$R', —SO$_2$N(R')$_2$ or —SOR' groups, or —R', where each R', independent of any other R' in any listed group, is selected from H, an alkyl group, an alkenyl group, an alkynyl group or an aryl group, and an acyl group each of which alkyl, alkenyl, alkynyl, aryl or acyl groups is optionally substituted with a halogen, —OH, —CN, —NO$_2$, or —SH group and wherein any two R' groups substituted on the same or adjacent atoms in a molecule can be linked together to form a 4-7 member ring. In specific embodiments, alkyl groups are substituted with optionally substituted aryl groups, particularly optionally substituted phenyl groups or optionally substituted biphenyl groups. In other specific embodiments, aryl groups, particularly phenyl groups, are optionally substituted with alkyl groups, particularly with alkyl groups having 1-3 carbon atoms or alkyl groups having 1-6 carbon atoms.

In specific embodiments for each definition for each of CX1-CX7 above:

$R_6$ and $R_7$ are both H;
$R_6$ and $R_7$ are, independently, selected from H or alkyl having 1-3 carbon atoms;
n is 1;
n is 2;
X is H;
X is OH or any listed combination of $R_6$, $R_7$, n and X.
In specific embodiments for Z which is neutral:
Q is M and M, $M_1$-$M_3$ are H; or
Q is H.
In specific embodiments for Z which are cationic:
Q is a negative charge;
Q is a negative charge and $M_1$-$M_3$ are all H;
Q is a negative charge and $M_1$-$M_3$ are all H; or
Q is a negative charge and one or more of $M_1$-$M_3$ are —(CH$_2$)$_p$—O—CO—R or —(CH$_2$)$_p$—O—C—R groups.
In specific embodiments of compounds having structure CX5, any of $Z_1$-$Z_5$ is an optionally substituted phenyl group, or an optionally substituted biphenyl group. In specific embodiments, $Z_1$-$Z_5$ are phenyl groups substituted with one or more halogens. In specific embodiments, any two of $Z_1$-$Z_5$ are halogens. In specific embodiments, any of $Z_1$-$Z_5$ is a CN group. In specific embodiments, $Z_1$-$Z_5$ are unsubstituted phenyl groups or unsubstituted biphenyl groups. In specific embodiments, any two Z on adjacent ring carbons can together form one or more rings which may contain one or more double bonds or which may be aromatic. In specific embodiments, $Z_2$ and $Z_3$ can together form one or more rings which may contain one or more double bonds or which may be aromatic. In a specific embodiments, $Z_1$ or $Z_2$ is a biphenyl group. In any of the specific embodiments listed for values of any of $Z_1$-$Z_5$,Q and $M_1$-$M_3$ can be OH, —(CH$_2$)$_p$—O—CO—R, where p is 1 or 2 or —(CH$_2$)$_p$—O—C—R, where p is 1 or 2. In any embodiments having structure CX5, X can be H. In any embodiments having structure CX5, X can be OH. In any embodiments having structure CX5, n can be 1. In any embodiments having structure CX5, X can be OH. In any embodiments having structure CX5, n can be 2. Specific examples of embodiments having structure CX5 include among others compounds 491, 493, 494, 495, 496, 498, 608, 618, 621, 622, 623, 624, 625, 640, 647, and 648.

In specific embodiments, $R_1$-$R_4$ groups which are alkyl, alkenyl, or alkynyl groups have 2, 3, 4, 5, 6 or more carbon atoms. In specific embodiments, at least one $R_1$-$R_4$ group in a molecules which are alkyl, alkenyl, or alkynyl groups has 2, 3, 4, 5, 6 or more carbon atoms. In specific embodiments, $R_1$ is an alkyl group substituted with an optionally substituted aryl group, and more specific is an alkyl group substituted with an optionally substituted phenyl group. In specific embodiments, $R_1$ and $R_2$ are alkyl or alkenyl groups which are linked together to form a 4-7 member and more preferably a 5 or 6 member ring.

Therapeutically and/or functionally compounds of this invention include those of formulas XX11-XX14:

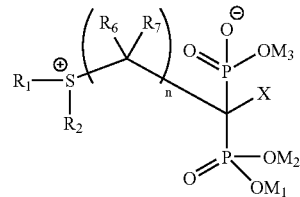

XX11

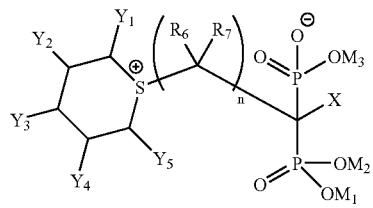

XX12

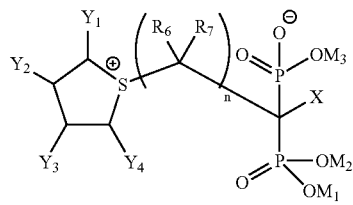

XX13

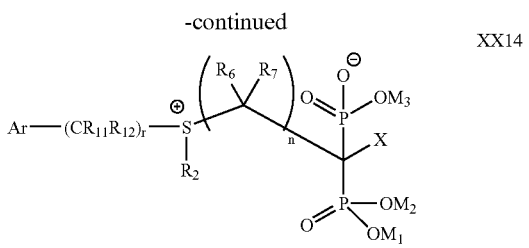

and salts, esters and hydrates thereof.

In each of XX11-XX14, $M_1$-$M_3$, $R_6$, $R_7$, n, X, $R_1$ and $R_2$ are as defined above; $Y_1$ to $Y_5$, independently of one another and other Y in the molecule, are selected from the group consisting of a hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group which can be a heteroaryl group, where each R, independent of any other R in any listed group, is selected from H, an optionally substituted alkyl group, an optionally substituted aryl group, and an optionally substituted acyl group wherein any two Y groups substituted on adjacent carbons of the same ring or any two carbons substituted on adjacent rings can be linked together to form a 4-7 member ring which may contain one or more double bonds, be aromatic and/or contain one or more heteroatoms (e.g., S, O or N); $R_{11}$ and $R_{12}$ are selected from hydrogen, a halogen, a —CN, —OR, —COOR, , —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group, where each R, independent of any other R in any listed group, is selected from H, an optionally substituted alkyl group, an optionally substituted aryl group, and an optionally substituted acyl group; r is zero or an integer ranging from 1-10, or 1-6, and Ar is an optionally substituted aryl group which may be a heteroaromatic group, wherein one or more $CR_{11}R_{12}$ moieties can be replaced with an O atom.

In specific embodiments of XX11, $R_1$ is optionally substituted alkyl having 2-20 carbon atoms. In any specific embodiments of XX11, $R_1$ is an alkyl ether group having 1-20 carbon atoms. In specific embodiments of XX11, $R_1$ is an optionally substituted alkyl group having 1-10 carbon atoms. In specific embodiments of XX11, $R_1$ is an optionally substituted alkenyl group having 1-20 carbon atoms. In specific embodiments of XX11, $R_1$ is an optionally substituted dienyl group (alkenyl group with two double bonds) having 1-20 carbon atoms. In specific embodiments of XX11, $R_1$ is an optionally substituted alkynyl group having 1-20 carbon atoms. In specific embodiments, $R_1$ is an unsubstituted alkyl group having 1-6 carbon atoms. In specific embodiments of XX11, $R_1$ is an alkyl group having 1-10 carbon atoms substituted with an aryl group. In specific embodiments of XX11, $R_1$ is optionally substituted straight-chain alkyl having 2-20 carbon atoms. In specific embodiments of XX11, $R_2$ is a group other than a methyl group. In specific embodiments of XX11, when n is 1, $R_2$ is a group other than a methyl group. In specific embodiments of XX11, when n is 1, $R_1$ and $R_2$ are groups other than methyl groups. In specific embodiments of XX11, $R_1$ and $R_2$ are groups other than methyl groups. In specific embodiments of XX12 or XX13, all of $Y_1$-$Y_5$ are hydrogens. In specific embodiments of XX12 or XX13, all of $Y_1$-$Y_5$ are hydrogens or optionally substituted alkyl groups having 1-3 carbon atoms. In specific embodiments of XX12 or XX13, one or more of $Y_1$-$Y_5$ are acyl groups. In specific embodiments of XX12 or XX13, one or more of $Y_1$-$Y_5$ are alkoxy groups. In specific embodiments of XX12 or XX13, one of $Y_1$-$Y_5$ are aryl groups. In specific embodiments of XX12 or XX13, all of $Y_1$-$Y_5$ are optionally substituted phenyl groups. In specific embodiments of XX12 or XX13, one of $Y_1$-$Y_5$ are optionally substituted biphenyl groups. In specific embodiments of XX12 or XX13, one of $Y_1$-$Y_5$ is a heteroaromatic group. In specific embodiments of XX14 hydrogens, cyano groups, nitro groups, halogens or optionally substituted alkyl groups having 1-6 or 1-3 carbon atoms In specific embodiments of XX14, $R_{11}$ and $R_{12}$ are all hydrogens. In specific embodiments of XX14, Ar is an optionally substituted phenyl. In specific embodiments of XX14, Ar is optionally substituted with an alkyl or alkoxy group. In specific embodiments of XX14, Ar is optionally substituted with an alkyl or alkoxy group having 1-10 carbon atoms. In specific embodiments of XX14, Ar is optionally substituted with an alkyl or alkoxy group having 1-6 carbon atoms. In specific embodiments of XX14, Ar is an optionally substituted biphenyl. In specific embodiments of XX14, Ar is an optionally substituted naphthyl. In specific embodiments of XX14, Ar is an optionally substituted benzofuranyl. In specific embodiments of XX14, Ar is an optionally substituted dibenzofuranyl. In specific embodiments of XX14, Ar is an alkoxy-substituted phenyl group. In specific embodiments of XX14, r is 1-6. In specific embodiments of XX14, r is 2-4. In specific embodiments of XX14, —$(CR_{11}CR_{12})_r$— is —O—$(CR_{11}R_{12})_{r-1}$—. In specific embodiments of XX14,—$(CR_{11}CR_{12})_r$— is —$(R_{11}R_{12})_t$—O—$(CR_{11}R_{12})_s$ where s+t=3-20 and more specifically where s and t, independently, are 2, 3 or 4. In specific embodiments,—$(CR_{11}CR_{12})_r$— is —O—$(CH_2)_{r-1}$—. In specific embodiments of XX14,—$(CR_{11}CR_{12})_r$— is —$(CH_2)_t$—O—$(CH_2)_s$, where s+t=3-20 and more specifically where s and t, independently, are 2, 3 or 4.

In any specific embodiments of XX11, XX12, XX13, or XX14, Q is M. In any specific embodiments of XX11, XX12, XX13, or XX14, any one or more of M, $M_1$, $M_2$ or $M_3$ can be H or a salt or ester thereof. In specific embodiments of XX11, XX12, XX13, or XX14, all $R_6$ and $R_7$ are hydrogens. In any specific embodiments of XX11, XX12, XX13, or XX14, X can be H. In any specific embodiments of XX11, XX12, XX13, or XX14, X can be OH. In any specific embodiments of XX11, XX12, XX13, or XX14, n can be 1. In any specific embodiments of XX11, XX12, XX13, or XX14, n can be 2. In any specific embodiments XX11, XX12, XX13, or XX14 can be pharmaceutically acceptable salts. In any specific embodiments XX11, XX12, XX13, or XX14 can be pharmaceutically acceptable esters. In any specific embodiments XX11, XX12, XX13, or XX14 can be pharmaceutically acceptable hydrates. In any specific embodiments of XX11, XX12, XX13, or XX14, $R_2$ is an alkyl group having 1, 2 or 3 carbon atoms. In any specific embodiments of XX11, XX12, XX13, or XX14, $R_2$ is a methyl group. In any specific embodiments of XX11, XX12, XX13, or XX14, $R_2$ is an ethyl group. In any specific embodiments of XX11, XX12, XX13, or XX14, one or both of $R_6$ and/or $R_7$ are optionally substituted alkyl groups. In any specific embodiments of XX11, XX12, XX13, or XX14, one or both of $R_6$ and/or $R_7$ are halogens.

Therapeutically and/or functionally active compounds of this invention include those of formulas XX21-XX22:

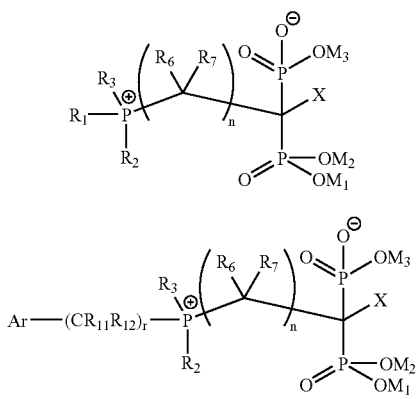

XX21

XX22 and salts, esters and hydrates thereof.

In each of XX21 or XX22, $M_1$-$M_3$, $R_6$, $R_7$, n, X, $R_1$, $R_2$ and $R_3$ are as defined above; $R_{11}$ and $R_{12}$ are selected from hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group, where each R, independent of any other R in any listed group, is selected from H, an optionally substituted alkyl group, an optionally substituted aryl group, and an optionally substituted acyl group; r is zero or an integer ranging from 1-10, or 1-6, and Ar is an optionally substituted aryl group which may be a heteroaromatic group, wherein one or more $CR_{11}R_{12}$ moieties can be replaced with an O atom.

In specific embodiments of XX21, $R_1$ is optionally substituted alkyl having 2-20 carbon atoms. In any specific embodiments of XX21, $R_1$ is an alkyl ether group having 1-20 carbon atoms. In specific embodiments of XX21, $R_1$ is an optionally substituted alkyl group having 1-10 carbon atoms. In specific embodiments of XX21, $R_1$ is an optionally substituted alkenyl group having 1-20 carbon atoms. In specific embodiments of XX21, $R_1$ is an optionally substituted dienyl group (alkenyl group with two double bonds) having 1-20 carbon atoms. In specific embodiments of XX21, $R_1$ is an optionally substituted alkynyl group having 1-20 carbon atoms. In specific embodiments, $R_1$ is an unsubstituted alkyl group having 1-6 carbon atoms. In specific embodiments of XX21, $R_1$ is an alkyl group having 1-10 carbon atoms substituted with an aryl group. In specific embodiments of XX21, $R_1$ is optionally substituted straight-chain alkyl having 2-20 carbon atoms. In specific embodiments of XX21, $R_2$ is a group other than a methyl group. In specific embodiments of XX21, when n is 1, $R_2$ is a group other than a methyl group. In specific embodiments of XX21, when n is 1, $R_1$ and $R_2$ are groups other than methyl groups. In specific embodiments of XX21, $R_1$ and $R_2$ are groups other than methyl groups. In specific embodiments of XX12 or XX13, all of $Y_1$-$Y_5$ are hydrogens. In specific embodiments of XX22, $R_{11}$ and $R_{12}$ are selected from hydrogens, cyano groups, nitro groups, halogens or optionally substituted alkyl groups having 1-6 or 1-3 carbon atoms. In specific embodiments of XX22, $R_{11}$ and $R_{12}$ are all hydrogens. In specific embodiments of XX22, Ar is optionally substituted phenyl. In specific embodiments of XX22, Ar is optionally substituted biphenyl. In specific embodiments of XX22, Ar is optionally substituted naphthyl. In specific embodiments of XX22, Ar is optionally substituted benzofuranyl. In specific embodiments of XX22, Ar is optionally substituted dibenzofuranyl. In specific embodiments of XX22, Ar is substituted with an alkyl or alkoxy group. In specific embodiments of XX22, Ar is substituted with an alkyl or alkoxy group having 1-10 carbon atoms. In specific embodiments of XX22, Ar is substituted with an alkyl or alkoxy group having 1-6 carbon atoms. In specific embodiments of XX22, Ar is an alkoxy substituted phenyl group. In specific embodiments of XX22, r is 1-6. In specific embodiments of XX22, r is 2-4. In specific embodiments of XX22, —$(CR_{11}CR_{12})_r$— is —O—$(CR_{11}R_{12})_{r-1}$—. In specific embodiments of XX22,—$(CR11CR_{12})_r$— is —$(R_{11}R_{12})_t$—O—$(CR_{11}R_{12})_s$ where s+t=3-20 and more specifically where s and t, independently, are 2, 3 or 4. In specific embodiments,—$(CR_{11}CR_{12})_r$— is —O—$(CH_2)_{r-1}$—. In specific embodiments of XX22,—$(CR_{11}CR_{12})_r$— is —$(CH_2)_t$—O—$(CH_2)_s$ where s+t=3-20 and more specifically where s and t, independently, are 2, 3 or 4.

In any specific embodiments of XX21 or XX22, any one or more of M, $M_1$, $M_2$ or $M_3$ can be H or a salt or ester thereof. In specific embodiments of XX21 or XX22, all $R_6$ and $R_7$ are hydrogens. In any specific embodiments of XX21 or XX22, X can be H. In any specific embodiments of XX21 or XX22, X can be OH. In any specific embodiments of XX21 or XX22, n can be 1. In any specific embodiments of XX21 or XX22, n can be 2. In any specific embodiments XX21 or XX22 can be pharmaceutically acceptable salts. In any specific embodiments XX21 or XX22 can be pharmaceutically acceptable esters. In any specific embodiments XX21 or XX22 can be pharmaceutically acceptable hydrates. In any specific embodiments XX21 or XX22, $R_2$ is an alkyl groups having 1, 2 or 3 carbon atoms. In any specific embodiments of XX21 or XX22, $R_2$ is a methyl group. In any specific embodiments of XX21 or XX22, $R_2$ is an ethyl group. In any specific embodiments of XX21 or XX22, one or both of $R_6$ and/or $R_7$ are optionally substituted alkyl groups. In any specific embodiments of XX21 or XX22, one or both of $R_6$ and/or $R_7$ are halogens.

Therapeutically and/or functionally active compounds of this invention include those of formulas XX31 and XX32:

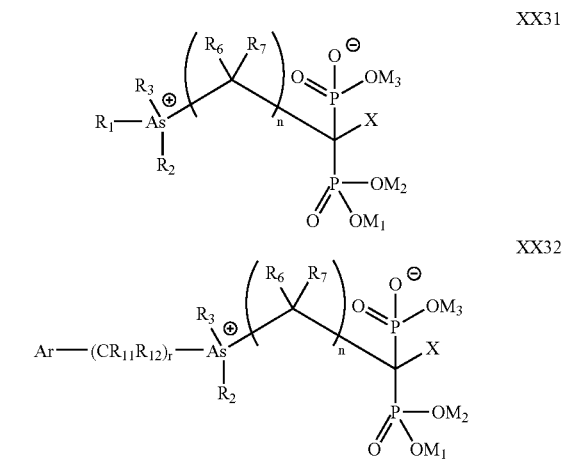

XX31

XX32 and salts, esters and hydrates thereof.

In each of XX31 or XX32, $M_1$-$M_3$, $R_6$, $R_7$, n, X, $R_1$, $R_2$ and $R_3$ are as defined above; $R_{11}$ and $R_{12}$ are selected from hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group, where each R, independent of any other R in any listed group, is selected from H, an optionally substituted alkyl group, an optionally substituted aryl group, and an optionally substituted acyl group; r is zero or an integer ranging from 1-10, or 1-6, and Ar is an optionally substituted aryl group which may be a heteroaromatic group, wherein one or more CR$_{11}$R$_{12}$ moieties can be replaced with an O atom.

In specific embodiments of XX31, R$_1$ is optionally substituted alkyl having 2- 20 carbon atoms. In any specific embodiments of XX31, R$_1$ is an alkyl ether group having 1-20 carbon atoms. In specific embodiments of XX31, R$_1$ is an optionally substituted alkyl group having 1-10 carbon atoms. In specific embodiments of XX31, R$_1$ is an optionally substituted alkenyl group having 1-20 carbon atoms. In specific embodiments of XX31, R$_1$ is an optionally substituted dienyl group (alkenyl group with two double bonds) having 1-20 carbon atoms. In specific embodiments of XX31, R$_1$ is an optionally substituted alkynyl group having 1-20 carbon atoms. In specific embodiments, R$_1$ is an unsubstituted alkyl group having 1-6 carbon atoms. In specific embodiments of XX31, R$_1$ is an alkyl group having 1-10 carbon atoms substituted with an aryl group. In specific embodiments of XX31, R$_1$ is optionally substituted straight-chain alkyl having 2-20 carbon atoms. In specific embodiments of XX31 or XX32, R$_2$ and R$_3$ are optionally substituted alkyl groups having 1-10 carbon atoms. In specific embodiments of XX31 or XX32, R$_2$ and R$_3$ are optionally substituted alkyl groups having 1-6 carbon atoms. In specific embodiments of XX31 or XX32, R$_3$ is an alkyl group substituted with an aryl group. In specific embodiments of XX31 or XX32, R$_2$ is a group other than a methyl group. In specific embodiments of XX31 or XX32, when n is 1, R$_2$ is a group other than a methyl group. In specific embodiments of XX31 or XX32, R$_2$ and R$_3$ the same groups. In specific embodiments of XX31 or XX32, R$_2$ and R$_3$ are different groups. In specific embodiments of XX31 or XX32, when n is 1, R$_1$ and R$_2$ are groups other than methyl groups. In specific embodiments of XX31 or XX32, R$_1$ and R$_2$ are groups other than methyl groups. In specific embodiments of XX31 or XX32, R$_2$ and R$_3$ are groups other than methyl groups. In specific embodiments of XX32, R$_{11}$ and R$_{12}$ are selected from hydrogens, cyano groups, nitro groups, halogens or optionally substituted alkyl groups having 1-6 or 1-3 carbon atoms. In specific embodiments of XX32, R$_{11}$ and R$_{12}$ are all hydrogens. In specific embodiments of XX32, Ar is an optionally substituted phenyl. In specific embodiments of XX32, Ar is optionally substituted with an alkyl or alkoxy group. In specific embodiments of XX32, Ar is optionally substituted with an alkyl or alkoxy group having 1-10 carbon atoms. In specific embodiments of XX32, Ar is optionally substituted with an alkyl or alkoxy group having 1-6 carbon atoms. In specific embodiments of XX32, Ar is optionally substituted biphenyl. In specific embodiments of XX32, Ar is optionally substituted naphthyl. In specific embodiments of XX32, Ar is optionally substituted benzofuranyl. In specific embodiments of XX32, Ar is optionally substituted dibenzofuranyl. In specific embodiments of XX32, Ar is an alkoxy substituted phenyl. In specific embodiments of XX32, r is 1-6. In specific embodiments of XX32, r is 2-4. In specific embodiments of XX32, —(CR$_{11}$CR$_{12}$)$_r$— is —O—(CR$_{11}$R$_{12}$)$_{r-1}$—. In specific embodiments of XX32, —(CR$_{11}$CR$_{12}$)$_r$— is —(R$_{11}$R$_{12}$)$_t$—O—(CR$_{11}$R$_{12}$)$_s$ where s+t=3-20 and more specifically where s and t, independently, are 2, 3 or 4. In specific embodiments, —(CR$_{11}$CR$_{12}$)$_r$— is —O—(CH$_2$)$_{r-1}$—. In specific embodiments of XX32, —(CR$_{11}$CR$_{12}$)$_r$— is —(CH$_2$)$_t$—O—(CH$_2$)$_s$ where s+t=3-20 and more specifically where s and t, independently, are 2, 3 or 4.

In any specific embodiments of XX31 or XX32, any one or more of M, M$_1$, M$_2$ or M$_3$ can be H or a salt or ester thereof. In specific embodiments of XX31 or XX32, all R$_6$ and R$_7$ are hydrogens. In any specific embodiments of XX31 or XX32, X can be H. In any specific embodiments of XX21 or XX22, X can be OH. In any specific embodiments of XX31 or XX32, n can be 1. In any specific embodiments of XX31 or XX32, n can be 2. In any specific embodiments XX31 or XX32 can be pharmaceutically acceptable salts. In any specific embodiments XX31 or XX32 can be pharmaceutically acceptable esters. In any specific embodiments XX31 or XX32 can be pharmaceutically acceptable hydrates. In any specific embodiments XX31 or XX32, R$_2$ is an alkyl groups having 1, 2 or 3 carbon atoms. In any specific embodiments of XX31 or XX32, R$_2$ is a methyl group. In any specific embodiments of XX31 or XX32, R$_2$ is an ethyl group. In any specific embodiments of XX31 or XX32, one or both of R$_6$ and/or R$_7$ are optionally substituted alkyl groups. . In any specific embodiments of XX31 or XX32, one or both of R$_6$ and/or R$_7$ are halogens.

Therapeutically and/or functionally compounds of this invention include those of formulas XX41-XX42:

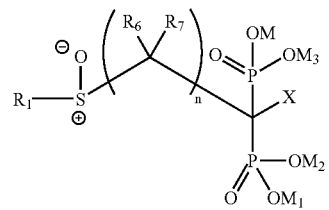

XX41

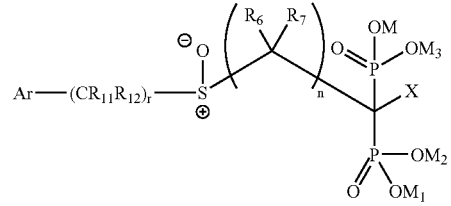

XX42 and salts, esters and hydrates thereof.

In each of XX41 or XX42, M, M$_1$-M$_3$, R$_6$, R$_7$, n, X, and R$_1$ are as defined above; R$_{11}$ and R$_{12}$ are selected from hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group, where each R, independent of any other R in any listed group, is selected from H, an optionally substituted alkyl group, an optionally substituted aryl group, and an optionally substituted acyl group; r is zero or an integer ranging from 1-10, or 1-6, and Ar is an optionally substituted aryl group which may be a heteroaromatic group, wherein one or more CR$_{11}$R$_{12}$ moieties can be replaced with an O atom.

In specific embodiments of XX41, R$_1$ is optionally substituted alkyl having 2-20 carbon atoms. In any specific embodiments of XX41, R$_1$ is an alkyl ether group having 1-20 carbon atoms. In specific embodiments of XX41, $R_1$ is an optionally substituted alkyl group having 1-10 carbon atoms. In specific embodiments of XX31, $R_1$ is an optionally substituted alkenyl group having 1-20 carbon atoms. In specific embodiments of XX41, $R_1$ is an optionally substituted dienyl group (alkenyl group with two double bonds) having 1-20 carbon atoms. In specific embodiments of XX41, $R_1$ is an optionally substituted alkynyl group having 1-20 carbon atoms. In specific embodiments, $R_1$ is an unsubstituted alkyl group having 1-6 carbon atoms. In specific embodiments of XX41, $R_1$ is an alkyl group having 1-10 carbon atoms substituted with an aryl group. In specific embodiments of XX41, $R_1$ is optionally substituted straight-chain alkyl having 2-20 carbon atoms. In specific embodiments of XX42, $R_{11}$ and $R_{12}$ are selected from hydrogens, cyano groups, nitro groups, halogens or optionally substituted alkyl groups having 1-6 or 1-3 carbon atoms. In specific embodiments of XX42, $R_{11}$ and $R_{12}$ are all hydrogens. In specific embodiments of XX42, Ar is an optionally substituted phenyl. In specific embodiments of XX42, Ar is optionally substituted biphenyl. In specific embodiments of XX42, Ar is optionally substituted naphthyl. In specific embodiments of XX42, Ar is optionally substituted benzofuranyl. In specific embodiments of XX42, Ar is optionally substituted dibenzofuranyl. In specific embodiments of XX42, Ar is an alkoxy substituted phenyl group. In specific embodiments of XX42, Ar is substituted with an alkoxy or alkyl group. In specific embodiments of XX42, Ar is substituted with an alkyl or alkoxy group having 1-10 carbon atoms. In specific embodiments of XX42, Ar is substituted with an alkyl or alkoxy group having 1-6 carbon atoms. In specific embodiments of XX42, r is 1-6. In specific embodiments of XX42, r is 2-4. In specific embodiments of XX42, —$(CR_{11}CR_{12})_r$— is —O—$(CR_{11}R_{12})_{r-1}$—. In specific embodiments of XX42, —$(CR_{11}CR_{12})_r$— is —$(R_{11}R_{12})_t$—O—$(CR_{11}R_{12})_s$ where s+t=3-20 and more specifically where s and t, independently, are 2, 3 or 4. In specific embodiments, —$(CR_{11}CR_{12})_r$— is —O—$(CH_2)_{r-1}$—. In specific embodiments of XX42,—$(CR_{11}CR_{12})_r$— is —$(CH_2)_t$—O—$(CH_2)_s$ where s+t=3-20 and more specifically where s and t, independently, are 2, 3 or 4.

In any specific embodiments of XX41 or XX42, any one or more of M, $M_1$, $M_2$ or $M_3$ can be H or a salt or ester thereof. In specific embodiments of XX41 or XX42, all $R_6$ and $R_7$ are hydrogens. In any specific embodiments of XX41 or XX42, X can be H. In any specific embodiments of XX41 or XX42, X can be OH. In any specific embodiments of XX41 or XX42, n can be 1. In any specific embodiments of XX41 or XX42, n can be 2. In any specific embodiments XX41 or XX42 can be pharmaceutically acceptable salts. In any specific embodiments XX41 or XX42 can be pharmaceutically acceptable esters. In any specific embodiments XX41 or XX42 can be pharmaceutically acceptable hydrates. In any specific embodiments XX41 or XX42, $R_2$ is an alkyl groups having 1, 2 or 3 carbon atoms. In any specific embodiments of XX41 or XX42, $R_2$ is a methyl group. In any specific embodiments of XX41 or XX42, $R_2$ is an ethyl group. In any specific embodiments of XX41 or XX42, one or both of $R_6$ and/or $R_7$ are optionally substituted alkyl groups. In specific embodiments of XX41 or XX42, one or both of $R_6$ and/or $R_7$ are halogens.

Therapeutically and/or functionally compounds of this invention include those of formulas XX51-XX53:

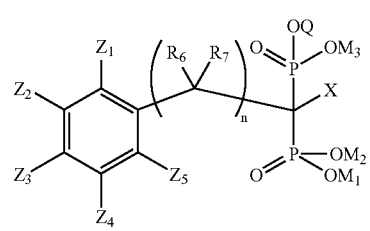

XX51

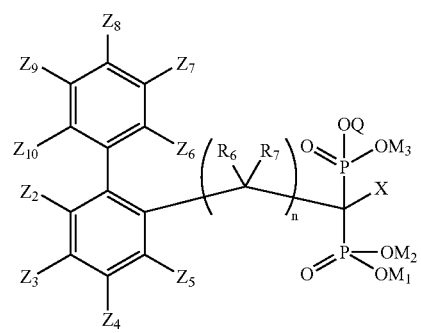

XX52

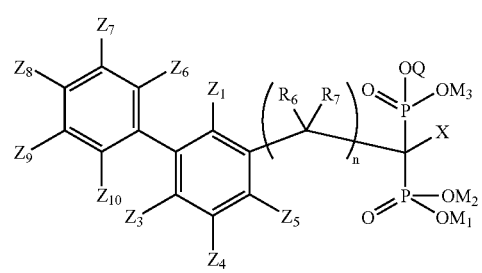

XX53

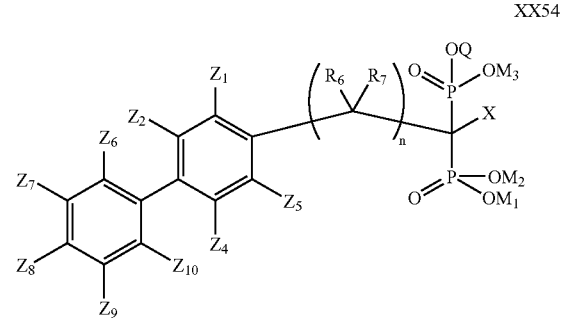

XX54

In each of XX51-XX54, Q, $M_1$-$M_3$, $R_6$, $R_7$, n, $Z_1$-$Z_5$ are as defined above and $Z_6$ to $Z_{10}$, independently of one another and other Z in the molecule, are selected from the group consisting of a hydrogen, a halogen, a —CN, —OR, —COOR,, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group which can be a heteroaryl group, where each R, independent of any other R in any listed group, is selected from H, an optionally substituted alkyl group, an optionally substituted aryl group, and an optionally substituted acyl group wherein any two Z groups substituted on adjacent carbons of the same ring or any two carbons substituted on adjacent rings can be linked together to form a 4-7 member ring which may contain one or more double bonds, be aromatic and/or contain one or more heteroatoms (e.g., S, O or N).

In specific embodiments of XX51, XX52, XX53, or XX54, $Z_1$ and $Z_5$ are hydrogens. In specific embodiments of XX51, XX52, XX53, or XX54, $Z_2$ and $Z_5$ are hydrogen. In specific embodiments of XX51, XX52, XX53, or XX54, $Z_6$ and $Z_{10}$ are hydrogens. In specific embodiments of XX51, XX52, XX53, or XX54, $Z_1$, $Z_5$, $Z_6$ and $Z_{10}$ are all hydrogens. In specific embodiments of XX51, XX52, XX53, or XX54, all Zs are hydrogens or alkyl groups having 1-3 carbon atoms. In specific embodiments of XX52, $Z_2$, $Z_5$, $Z_6$ and $Z_{10}$ are all hydrogens. In specific embodiments of XX53, $Z_1$, $Z_3$, $Z_6$ and $Z_{10}$ are all hydrogens. In specific embodiments of XX54, $Z_2$, $Z_4$, $Z_6$ and $Z_{10}$ are all hydrogens. In specific embodiments of XX51, XX52, XX53, or XX54, one of $Z_1$-$Z_{10}$ is an optionally substituted phenyl ring. In specific embodiments of XX51, XX52, XX53, or XX54, one of $Z_1$-$Z_{10}$ is an unsubstituted phenyl ring. In specific embodiments of XX51, XX52, XX53, or XX54, one of $Z_1$-$Z_{10}$ is a phenyl ring substituted with one cyano group. In specific embodiments of XX51, XX52, XX53, or XX54, one of $Z_1$-$Z_{10}$ is a phenyl ring substituted with one or two halogens. In specific embodiments of XX51, XX52, XX53, or XX54, one of $Z_1$-$Z_{10}$ is a phenyl ring substituted with one or two chlorines. In specific embodiments of XX51, XX52, XX53, or XX54, one of $Z_1$-$Z_{10}$ is a phenyl ring substituted with one or two bromines. In specific embodiments of XX51, XX52, XX53, or XX54, one of $Z_1$-$Z_{10}$ is a phenyl ring substituted with one or two fluorines. In specific embodiments of XX51, XX52, XX53, or XX54, one of $Z_1$-$Z_{10}$ is a phenyl ring substituted with one or two iodines. In specific embodiments of XX51, XX52, XX53, or XX54, one of $Z_1$-$Z_{10}$ is a phenyl ring substituted with one or two optionally substituted alkyl groups having 1-6 or 1-3 carbon atoms. In specific embodiments of XX51, one or both of $Z_2$ or $Z_3$ carry a non-hydrogen substituent. In specific embodiments of XX51, $Z_2$ and $Z_3$ together form an aromatic ring. In specific embodiments of XX51, one of $Z_1$-$Z_5$ is a heterocyclic group which may be aromatic (e.g., a pyridinyl, pyrimidinyl, furanyl, benzofuranyl, dibenzofuranyl.). In specific embodiments of XX51, XX52, XX53, or XX54, one or two of $Z_1$-$Z_{10}$ carry non-hydrogen substituents. In specific embodiments of XX52, XX53, or XX54, $Z_{10}$ together with $Z_2$, $Z_3$ or $Z_4$ form a 5 or 6 member ring which may be aromatic and may contain one or more heteroatoms. In specific embodiments of XX52, XX53, or XX54, $Z_{10}$ together with $Z_2$, $Z_3$ or $Z_4$ form a furan or benzofuranyl group.

In any specific embodiments of XX51, XX52, XX53, or XX54, Q is M. In any specific embodiments of XX51, XX52, XX53, or XX54, any one or more of M, $M_1$, $M_2$ or $M_3$ can be H or a salt or ester thereof. In any specific embodiments of XX51, XX52, XX53, or XX54, all $R_6$ and $R_7$ are hydrogens. In any specific embodiments of XX51, XX52, XX53, or XX54, X can be H. In any specific embodiments of XX51, XX52, XX53, or XX54, X can be OH. In any specific embodiments of XX51, XX52, XX53, or XX54, n can be 1. In any specific embodiments of XX51, XX52, XX53, or XX54, n can be 2. In any specific embodiments XX51, XX52, XX53, or XX54 can be pharmaceutically acceptable salts. In any specific embodiments XX51, XX52, XX53, or XX54 can be pharmaceutically acceptable esters. In any specific embodiments XX51, XX52, XX53, or XX54 can be pharmaceutically acceptable hydrates.

Therapeutically and/or functionally compounds of this invention include those of formulas XX61, XX62, XX71 and XX72:

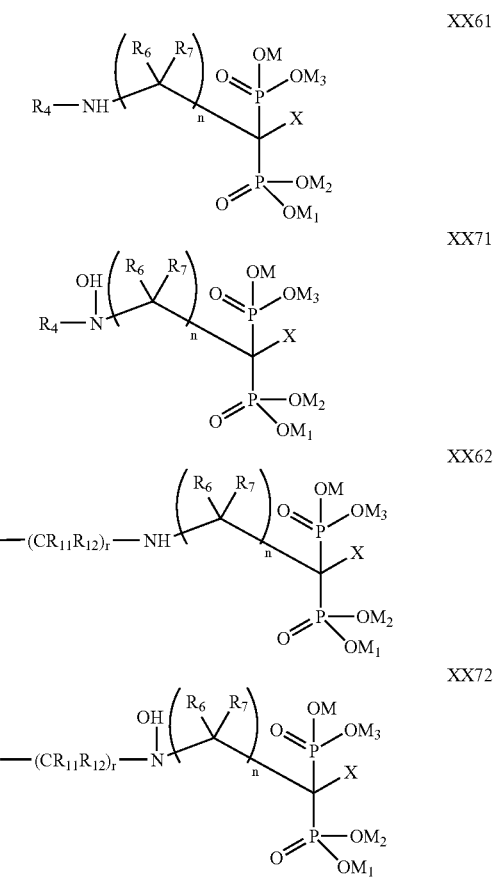

and salts, esters and hydrates thereof.

In each of XX61, XX62, XX71 or XX72, M, $M_1$-$M_3$, $R_6$, $R_7$, n, X, and $R_4$ are as defined above; $R_{11}$ and $R_{12}$ are selected from hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group, where each R, independent of any other R in any listed group, is selected from H, an optionally substituted alkyl group, an optionally substituted aryl group, and an optionally substituted acyl group; r is zero or an integer ranging from 1-10, or 1-6, and Ar is an optionally substituted aryl group which may be a heteroaromatic group, wherein one or more $CR_{11}R_{12}$ moieties can be replaced with an O atom.

In specific embodiments of XX61 or XX71, $R_4$ is optionally substituted alkyl having 2-20 carbon atoms. In any specific embodiments of XX61 or XX71, $R_4$ is an alkyl ether group having 1-20 carbon atoms. In specific embodiments of XX61 or XX71, $R_4$ is an optionally substituted alkyl group having 1-10 carbon atoms. In specific embodiments of XX61 or XX71, $R_4$ is an optionally substituted alkenyl group having 1-20 carbon atoms. In specific embodiments of XX61 or XX71, $R_4$ is an optionally substituted dienyl group (alkenyl group with two double bonds) having 1-20 carbon atoms. In specific embodiments of XX61 or XX71, $R_4$ is an optionally substituted alkynyl group having 1-20 carbon atoms. In specific embodiments of XX61 or XX71, $R_4$ is an unsubstituted alkyl group having 1-6 carbon atoms. In specific embodiments of XX61 or XX71, $R_4$ is an alkyl group having 1-10 carbon atoms substituted with an aryl group. In specific embodiments of XX61 or XX71, $R_4$ is optionally substituted straight-chain alkyl having 2-20 carbon atoms. In specific embodiments of XX61 or XX71, $R_4$ is an optionally substituted aryl group. In specific embodiments of XX61 or XX71, $R_4$ is an optionally substituted phenyl group. In specific embodiments of XX61 or XX71, $R_4$ is an optionally substituted heteroaromatic group. In specific embodiments of XX61 or XX71, $R_4$ is an optionally substituted pyridine or pyrimidine group. In specific embodiments of XX61 or XX71, $R_4$ is an optionally substituted nitrogen containing heteroaromatic group. In specific embodiments of XX61 or XX71, $R_4$ is an optionally substituted carbazolyl group (carbazole ring). In specific embodiments of XX61 or XX71, $R_1$ is an optionally substituted phenyl. In specific embodiments of XX61 or XX71, $R_1$ is a halogen substituted phenyl or biphenyl. In specific embodiments of XX61 or XX71, $R_1$ is optionally substituted biphenyl. In specific embodiments of XX61 or XX71, $R_1$ is optionally substituted naphthyl. In specific embodiments of XX61 or XX71, $R_1$ is optionally substituted benzofuranyl. In specific embodiments of XX61 or XX71, $R_1$ is optionally substituted dibenzofuranyl. In specific embodiments of XX61 or XX71, $R_1$ is an alkoxy substituted phenyl group. In specific embodiments of XX61 or XX71, R 1 is an aryl group substituted with an alkoxy or alkyl group. In specific embodiments of XX61 or XX71, $R_1$ is an aryl group substituted with an alkyl or alkoxy group having 1-10 carbon atoms. In specific embodiments of XX61 or XX71, $R_1$ is an aryl group substituted with an alkyl or alkoxy group having 1-6 carbon atoms. In specific embodiments of XX62 or XX72, $R_{11}$ and $R_{12}$ are selected from hydrogens, cyano groups, nitro groups, halogens or optionally substituted alkyl groups having 1-6 or 1-3 carbon atoms. In specific embodiments of XX62 or XX72, $R_{11}$ and $R_{12}$ are all hydrogens. In specific embodiments of XX62 or XX72, Ar is an optionally substituted phenyl. In specific embodiments of XX62 or XX72, Ar is optionally substituted biphenyl. In specific embodiments of XX62 or XX72, Ar is optionally substituted naphthyl. In specific embodiments of XX62 or XX72, Ar is optionally substituted benzofuranyl. In specific embodiments of XX62 or XX72, Ar is optionally substituted dibenzofuranyl. In specific embodiments of XX62 or XX72, Ar is an alkoxy substituted phenyl group. In specific embodiments of XX62 or XX72, Ar is substituted with an alkoxy or alkyl group. In specific embodiments of XX62 or XX72, Ar is substituted with an alkyl or alkoxy group having 1-10 carbon atoms. In specific embodiments of XX62 or XX72, Ar is substituted with an alkyl or alkoxy group having 1-6 carbon atoms. In specific embodiments of XX62 or XX72, r is 1-6. In specific embodiments of XX62 or XX72, r is 2-4. In specific embodiments of XX42, —$(CR_{11}CR_{12})_r$— is —O—$(CR_{11}R_{12})_{r-1}$—. In specific embodiments of XX62 or XX72, —$(CR_{11}CR_{12})_r$— is —$(R_{11}R_{12})_t$—O—$(CR_{11}R_{12})_s$ where s+t=3-20 and more specifically where s and t, independently, are 2, 3 or 4. In specific embodiments, —$(CR_{11}CR_{12})_r$— is —O—$(CH_2)_{r-1}$—. In specific embodiments of XX62 or XX72,—$(CR_{11}CR_{12})_r$— is —$(CH_2)_t$—O—$(CH_2)_s$ where s+t=3-20 and more specifically where s and t, independently, are 2, 3 or 4.

In any specific embodiments of XX61, XX62, Xx71, or XX72, any one or more of M, $M_1$, $M_2$ or $M_3$ can be H or a salt or ester thereof. In specific embodiments of XX61, XX62, Xx71, or XX72, all $R_6$ and $R_7$ are hydrogens. In any specific embodiments of XX61, XX62, Xx71, or XX72, X can be H. In any specific embodiments of XX61, XX62, Xx71, or XX72, X can be OH. In any specific embodiments of XX61, XX62, Xx71, or XX72, n can be 1. In any specific embodiments of XX61, XX62, Xx71, or XX72, n can be 2. In any specific embodiments XX61, XX62, Xx71, or XX72 can be pharmaceutically acceptable salts. In any specific embodiments XX61, XX62, Xx71, or XX72 can be pharmaceutically acceptable esters. In any specific embodiments XX61, XX62, Xx71, or XX72 can be pharmaceutically acceptable hydrates. In any specific embodiments XX61, XX62, Xx71, or XX72, $R_2$ is an alkyl groups having 1, 2 or 3 carbon atoms. In any specific embodiments of XX61, XX62, Xx71, or XX72, $R_2$ is a methyl group. In any specific embodiments of XX61, XX62, Xx71, or XX72, $R_2$ is an ethyl group. In any specific embodiments of XX61, XX62, Xx71, or XX72, one or both of $R_6$ and/or $R_7$ are optionally substituted alkyl groups. In any specific embodiments of XX61, XX62, Xx71, or XX72, one or both of $R_6$ and/or $R_7$ are halogens.

In certain embodiments, a compound of the invention includes compounds as described above in relation to compound BX1 but excepting the following compound structures (regardless of hydration state):

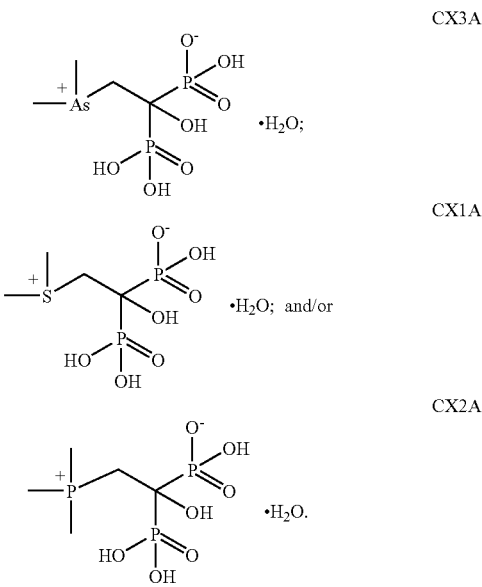

In claimed subject matter, the immediately foregoing arsonium, sulfonium, and phosphonium structures, regardless of hydration state, are optionally subject to disclaimer.

In an embodiment, the invention provides a composition comprising a compound. In embodiment, said composition comprises a therapeutically effective amount of the compound. In an embodiment, the invention provides a composition comprising a pharmaceutical formulation of a compound. In an embodiment, said pharmaceutical formulation comprises one or more excipients, carriers, and/or other components as would be understood in the art. In an embodiment, the invention provides a compound for use in the making of a medicament.

In an embodiment, the invention provides a method for treating a medical condition comprising administering to a subject in need thereof, a therapeutically effective amount of a compound of the invention. In an embodiment, the medical condition is a bone resorption disorder, a cancer, pain, an immune system disorder, and/or an infectious disease.

Pharmaceutically acceptable salts comprise pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

Compounds of the invention can have prodrug forms. Prodrugs of the compounds of the invention are useful in the methods of this invention. Any compound that will be converted in vivo to provide a biologically, pharmaceutically or therapeutically active form of a compound of the invention is a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191,1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

DETAILED DESCRIPTION OF THE INVENTION

Figure 1:
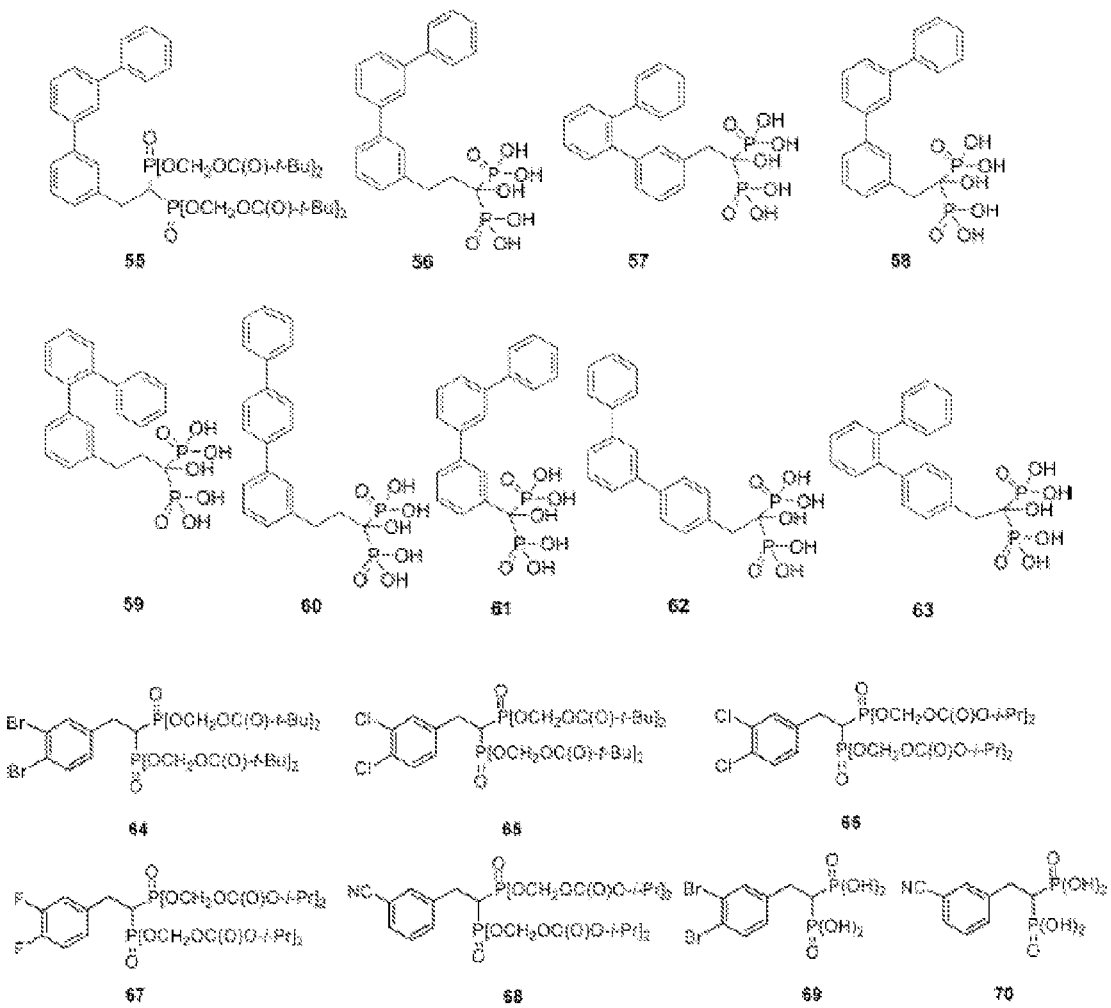
FIG. 1 illustrates various bisphosphonate compounds (generally non-nitrogen containing) with compound designations that are aliases for certain compounds designated elsewhere with alternate compound numbers such as in the 500 and 600 series. Compound 55, for example, is an alias for Compound 647 and relates to synthesis Scheme 1. Compounds 56-63 relate to synthesis Scheme 2, and compounds 64-70 relate to synthetic Scheme 3.

The invention may be further understood by the following non-limiting examples.

The following abbreviations are applicable. FPPS, farnesyl diphosphate synthase; UPPS (undecaprenyl pyrophosphate synthetase; also known as undecaprenyl diphosphate synthase); $PIC_{50}/pEC_{50}$, negative log of $IC_{50}$ and $EC_{50}$, respectively, where $IC_{50}$ and $EC_{50}$ are the concentrations that produce half-maximal inhibition or activation, respectively; T. brucei, Trypanosoma brucei; D. discoideum, Dictyostelium discoideum; γδ T cells, gamma delta T cells. Bisphosphonate compounds are typically designated by a number.

The following definitions are applicable. These definitions are intended to relate in particular to compounds having the general formula BX1 but can also apply to other compounds set forth herein.

Alkyl groups include straight-chain, branched and cyclic alkyl groups. Alkyl groups include those having from 1 to 20 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-20 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups optionally include substituted alkyl groups. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted.

Aryl groups include groups having one or more 5- or 6-member aromatic or heteroaromatic rings. Aryl groups can contain one or more fused aromatic rings. Heteroaromatic rings can include one or more N, O or S atoms in the ring. Heteroaromatic rings can include those with one, two or three N, those with one or two O, and those with one or two S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups.

Alkylaryl groups are aryl groups substituted with one or more alkyl groups wherein the alkyl groups optionally carry additional substituents and the aryl groups are optionally substituted. Specific alkylaryl groups are alkyl-substituted phenyl groups such as methylphenyl.

The rings that may be formed from two or more of $R^1$-$R^5$ together can be optionally substituted cycloalkyl groups, optionally substituted cycloalkenyl groups or aromatic groups. The rings may contain 3, 4, 5, 6, 7 or more carbons. The rings may be heteroaromatic in which one, two or three carbons in the aromatic ring are replaced with N, O or S. The rings may be heteroalkyl or heteroalkenyl, in which one or more $CH_2$ groups in the ring are replaced with O, N, NH, or S.

Optional substitution of any alkyl, alkenyl and aryl groups includes substitution with one or more of the following substituents: halogens, —CN, —COOR, —OR, —COR, —OCOOR, —CON(R)$_2$, —OCON(R)$_2$, —N(R)$_2$, —NO$_2$, —SR, —SO$_2$R, —SO$_2$N(R)$_2$ or —SOR groups. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for alkyl, alkenyl and aryl groups include among others:

—COOR where R is a hydrogen or an alkyl group or an aryl group and more specifically where R is methyl, ethyl, propyl, butyl, or phenyl groups all of which are optionally substituted;

—COR where R is a hydrogen, or an alkyl group or an aryl groups and more specifically where R is methyl, ethyl, propyl, butyl, or phenyl groups all of which groups are optionally substituted;

—CON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—OCON(R)$_2$ where each R, independently of each other R, is a hydrogen or an alkyl group or an aryl group and more specifically where R is methyl, ethyl, propyl, butyl, or phenyl groups all of which groups are optionally substituted; R and R can form a ring which may contain one or more double bonds;

—N(R)$_2$ where each R, independently of each other R, is a hydrogen, or an alkyl group, acyl group or an aryl group and more specifically where R is methyl, ethyl, propyl, butyl, or phenyl or acetyl groups all of which are optionally substituted; or R and R can form a ring which may contain one or more double bonds.

—SR, —SO$_2$R, or —SOR where R is an alkyl group or an aryl groups and more specifically where R is methyl, ethyl, propyl, butyl, phenyl groups all of which are optionally substituted; for —SR, R can be hydrogen;

—OCOOR where R is an alkyl group or an aryl groups;

—SO$_2$N(R)$_2$ where R is a hydrogen, an alkyl group, or an aryl group and R and R can form a ring;

—OR where R=H, alkyl, aryl, or acyl; for example, R can be an acyl yielding —OCOR* where R* is a hydrogen or an alkyl group or an aryl group and more specifically where R* is methyl, ethyl, propyl, butyl, or phenyl groups all of which groups are optionally substituted;

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo -substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups, and methoxyphenyl groups, particularly 4-methoxyphenyl groups.

EXAMPLE 1

Bisphosphonate Compounds

Certain embodiments are exemplified by compounds of formula BX1 as disclosed herein. In embodiments, the invention provides compounds having the following general structural formula CXA (which in many embodiments constitutes a subset of BX1). In embodiments, the invention specifically provides compounds with a charged sulfonium group, a charged phosphonium group, charged arsonium group, charged ammonium group, uncharged aromatic groups, taxane groups, and related bisphosphonate compounds. Other compounds are also provided. See, e.g., formula CXA:

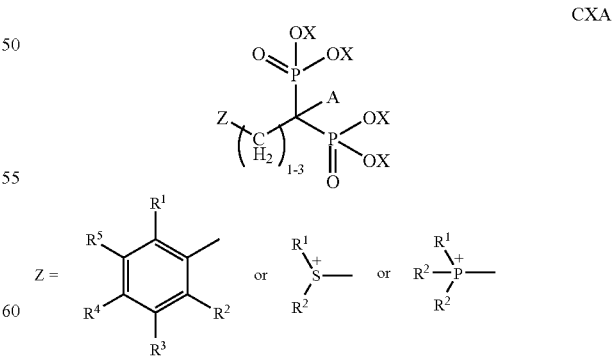

CXA or a pharmaceutically acceptable salt or ester thereof;
wherein: Z comprises one of the structures shown above;
X is H, —OH, or a halogen;
n is 1, 2, or 3;

R[1]-R[3], independently of one another and other R groups, are selected from the group consisting of a hydrogen, a halogen, a —CN, —OR, —COOR, —OCOOR, —COR, —CON (R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, and an optionally substituted aryl group, where each R, independent of any other R in any listed group, is selected from H, an optionally substituted alkyl group and an optionally substituted aryl group, an optionally substituted acyl group;

two or more of R[1]-R[5] can together form one or more rings which may contain one or more double bonds or which may be aromatic; and R[1], R[2], and R[3], independently of each other, are selected from the group consisting of a hydrogen, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group.

In an example of a salt, X can be a cation such as Na+. For an ester, X can be, for example, pivaloyloxymethylene, isopropyloxycarbonyl, and/or other structure as would be understood in the art.

In a specific embodiment, compounds 527, 540, 546, 547, 550, 564, 569, 572, 573, 574, 575, 576, 580, 581, 584, 585, 587, 589, and 594; and pharmaceutically acceptable salts, and esters thereof; are useful for treatment of a bone resorption clinical disorder.

In a specific embodiment, compounds 527, 540, 546, 547, 550, 564, 569, 572, 573, 574, 575, 576, 580, 581, 584, 585, 587, 589, and 594; and pharmaceutically acceptable salts, and esters thereof; are useful in treatment of protozoan diseases, useful for treatment of a bone resorption clinical disorder, and for immunotherapy.

In a specific embodiment, compounds, the des-hydroxy (where X is H) analogs of compounds 527, 540, 546, 547, 550, 564, 569, 572, 573, 574, 575, 576, 580, 581, 584, 585, 587, 589, and 594; and pharmaceutically acceptable salts, and esters thereof; are useful in the treatment of a bone resorption clinical disorder.

EXAMPLE 2

Terphenyl and Benzyl Bisphosphonate Compounds

We report the synthesis and testing of a series of novel bisphosphonates. The most potent molecules have high activity and can represent useful compositions for a variety of applications such as in bone resorption disorders, parasitic diseases, bacterial diseases, immunomodulation, and cancer.

The following general methods were used as shown in Schemes 1-3. This is a non-limiting embodiment and various A groups (X═H, F, Me) may also be produced using methods well known in the art.

Figure 2:
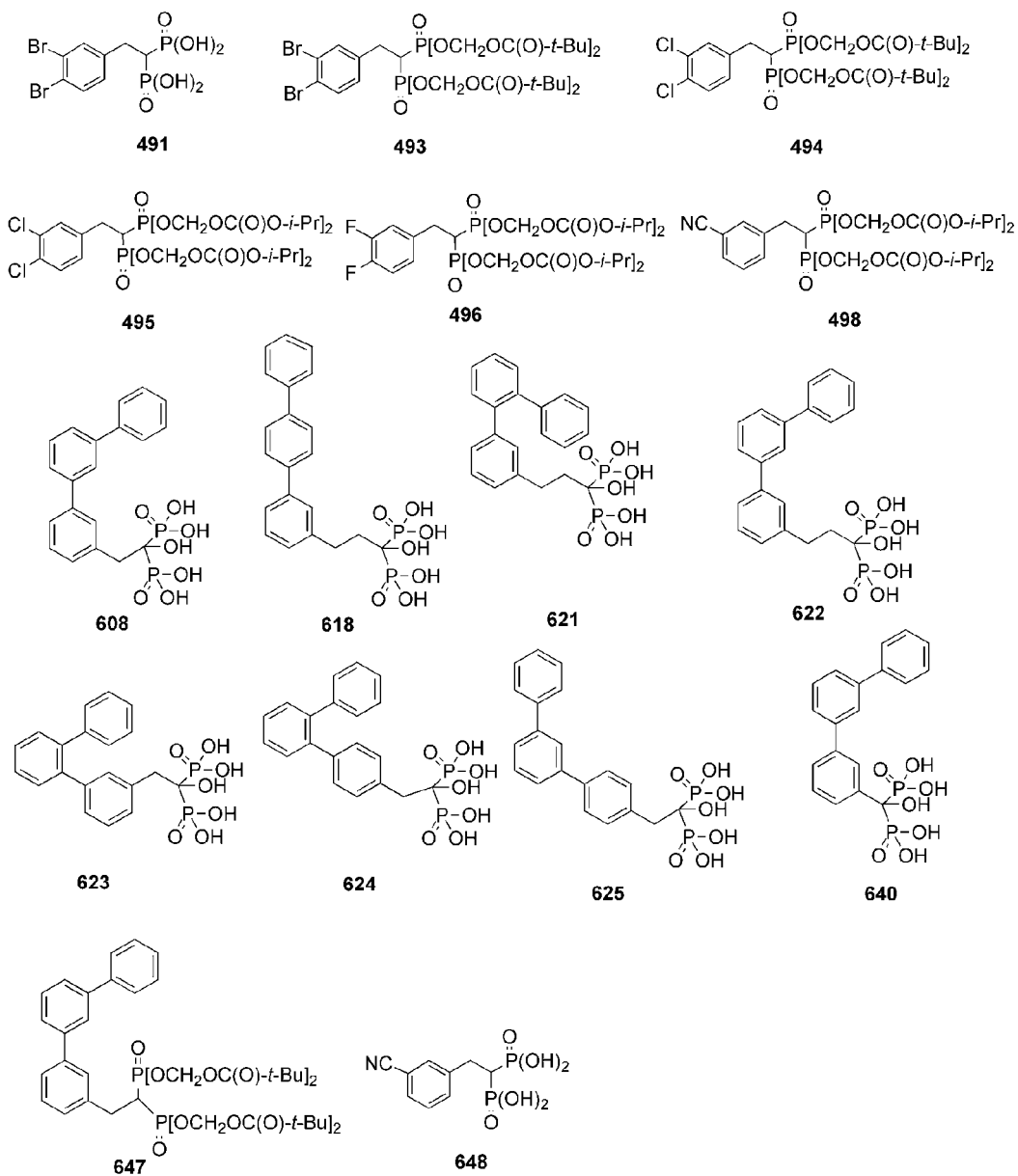
FIG. 2 illustrates structures of certain bisphosphonate compounds, e.g., terphenyl and benzyl bisphosphonates.

Scheme 1 (top), Scheme 2 (middle), and Scheme 3 (bottom). See also FIG. 1 and FIG. 2.

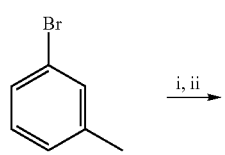

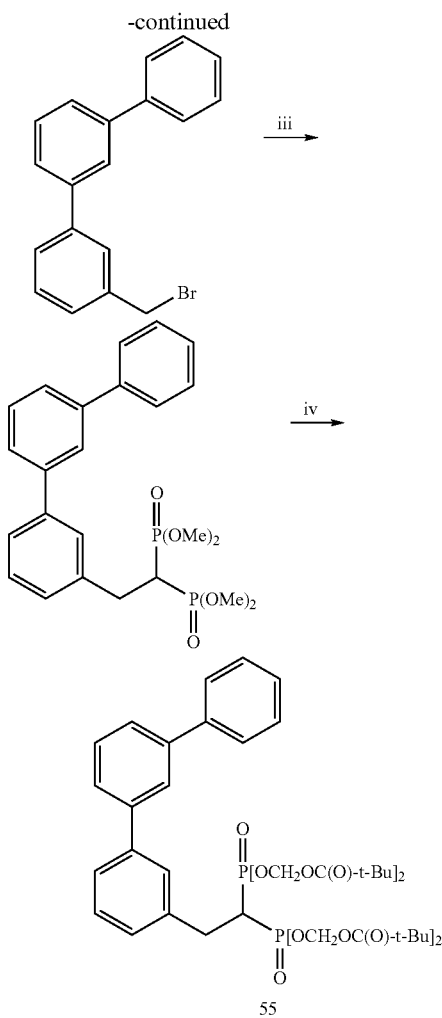

[a]Reagents: (i)3-biphenylboronic acid, Pd(PPh$_3$)$_4$, K$_2$CO$_3$; (ii) NBS, ALBN; (iii)CH$_2$(POOMe)$_2$, NaH, 64% for three steps; (iv) ClCH$_2$OC(O)-t-Bu, NaI, reflux, 42% isolated yield.

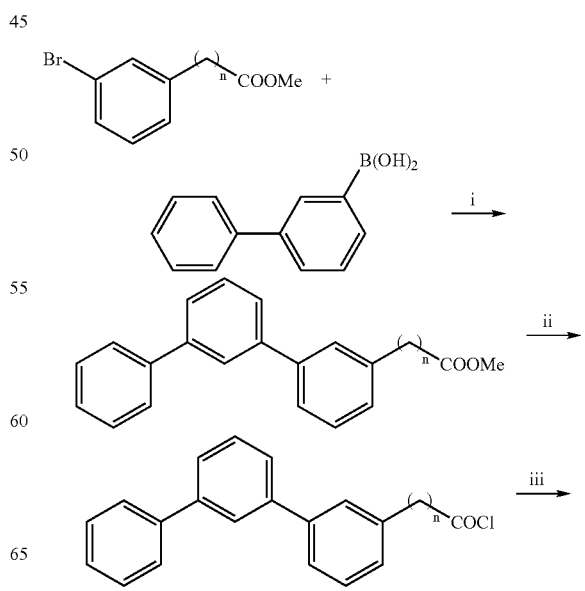

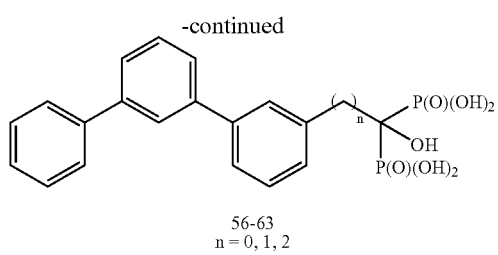

56-63
n = 0, 1, 2 a Reagents: (i)Pd(PPh3)4, K2CO3; (ii) NaOH,
THF-H2O, and then (COCl)2; (iii) P(OTMS)3

Certain compounds were also tested regarding the ability to inhibit undecaprenyl diphosphate synthase (UPPS). See results in Table 2. The data demonstrated that compounds were able to inhibit UPPS with IC50 values at even the sub-micromolar level, which is important in bacterial peptidoglycan biosynthesis such as in *Escherichia coli*. This indicates that the compounds can be useful in antimicrobial applications. For example, an antibacterial treatment can include contacting a bacterial cell with a compound of the invention. In an embodiment, a bacterial cell can be, e.g., a Gram negative organism such as *E. coli* or a Gram positive organism such as *Staphylococcus aureus*.

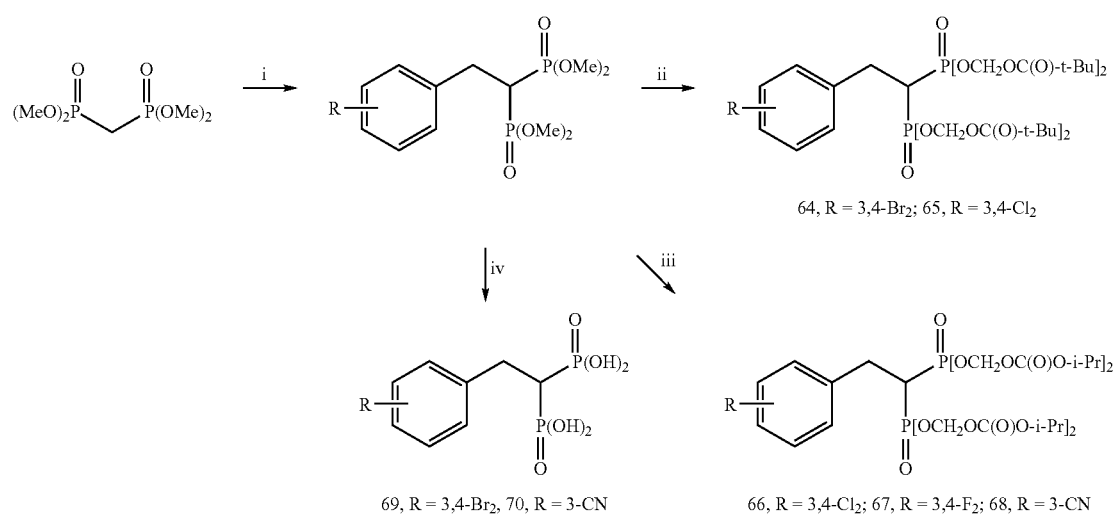

64, R = 3,4-Br2; 65, R = 3,4-Cl2

69, R = 3,4-Br2, 70, R = 3-CN

Figure 3:
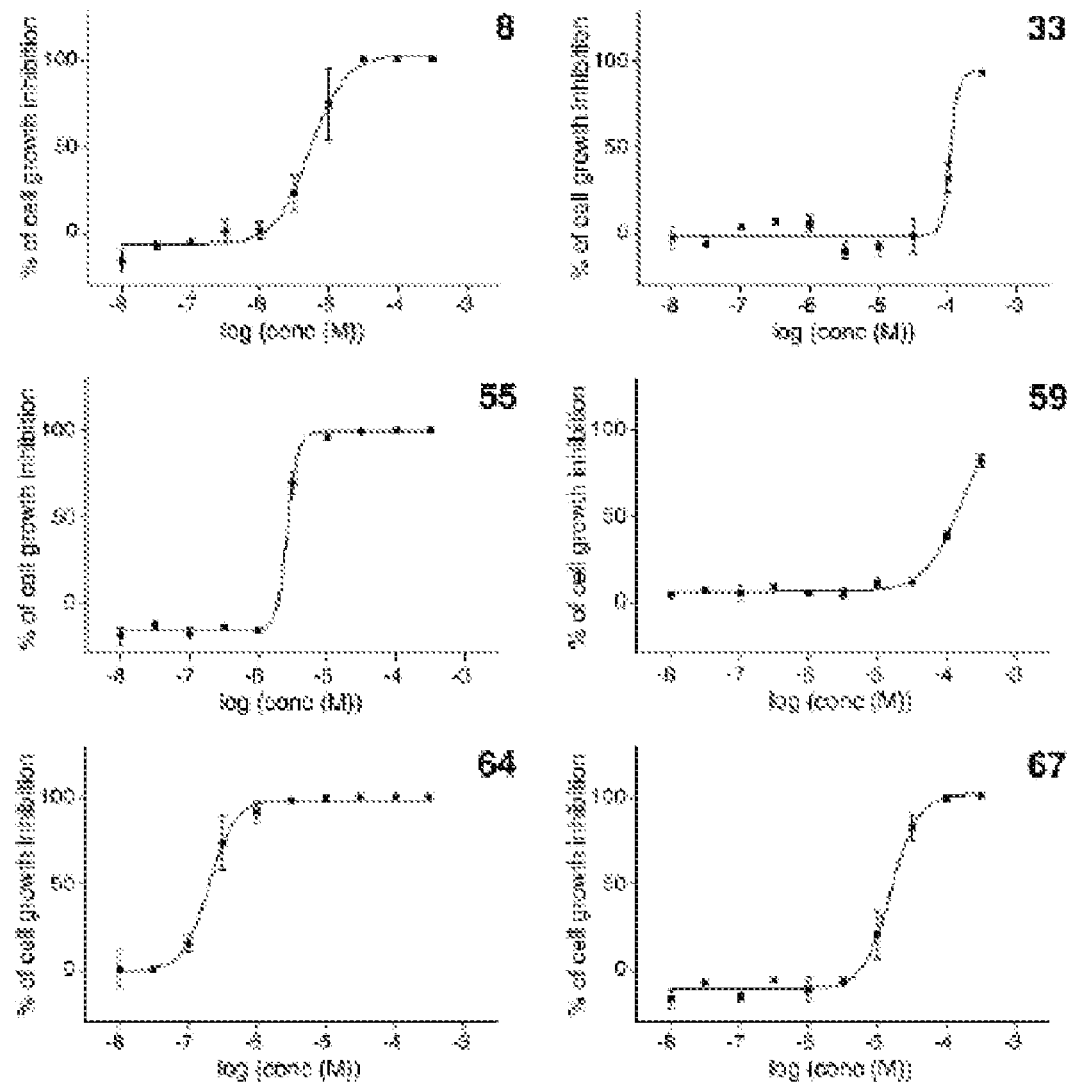
FIG. 3 illustrates representative dose response curves from tumor cell growth inhibition tests (for compounds 8, 33, 55, 59, 64 and 67).

66, R = 3,4-Cl2; 67, R = 3,4-F2; 68, R = 3-CN a Reagents: (i) NaH, RC6H4CH2Br, (ii) ClCH2OC(O)-t-Bu, NaI; (iii) ClCH2OC(O)O-i-Pr, NaI; (iv) TMSBr Bisphosphonate compounds were tested regarding tumor cell growth inhibition. Certain compounds were found to have potent activity in inhibiting tumor cell growth in breast (MCF-7), lung (NIH-H460) and central nervous system (SF-268, glioblastoma) cell lines. See Table 1 and FIG. 3 showing dose-response data.

TABLE 1

Activity in Tumor Cell Growth Inhibition.

| Compound | MCF-7 cell $IC_{50}$ (uM) | NCI-H460 cell $IC_{50}$ (uM) | SF-268 cell $IC_{50}$ (uM) |
|---|---|---|---|
| 647 | 2.62 | 1.64 | 2.38 |
| 622 | 43.87 | 46.87 | 44.66 |
| 623 | 92.74 | 86.06 | 57.98 |
| 608 | 152.30 | 139.70 | 129.50 |
| 621 | 146.00 | 133.40 | 143.20 |
| 618 | 195.70 | 132.20 | 174.70 |
| 640 | 309.80 | 285.30 | 303.10 |
| 625 | 412.10 | 413.10 | 619.90 |
| 624 | 1063.00 | 328.70 | 475.30 |
| 493 | 0.22 | 0.62 | 0.65 |
| 494 | 0.34 | 2.70 | 1.43 |
| 495 | 1.97 | 4.85 | 4.78 |
| 496 | 15.20 | 20.10 | 28.30 |
| 498 | 58.60 | 22.60 | 7.77 |
| 491 | 532.90 | 445.60 | 348.60 |

TABLE 2

UPPS inhibition by bisphosphonate compounds.

| compound | UPPS inhibition $IC_{50}$ (uM) |
|---|---|
| 629 | 0.33 |
| 608 | 0.61 |
| 628 | 0.88 |
| 625 | 0.89 |
| 640 | 1.86 |
| 626 | 1.91 |
| 622 | 2.39 |
| 621 | 7.51 |
| 294 | 9.03 |
| 364 | 10.00 |
| 646 | 12.09 |
| 618 | 12.46 |
| 642 | 12.66 |
| 633 | 19.26 |
| 632 | 32.71 |
| 620 | 36.73 |
| 641 | 47.86 |
| 614 | 85.63 |
| 601 | 112.65 |
| 619 | 153.57 |
| 228 | 411.29 |
| 651 | 279.38 |
| 652 | 500.63 |
| 673 | 399.50 |
| 674 | 522.60 |
| 675 | 629.40 |

Synthetic methods are further described and elemental analysis results for compounds which were synthesized are indicated in Table 3.

General method A) Suzuki coupling): An aryl boronic acid or its ester (6 mmol), a bromo substituted aromatic compound (5 mmol), $K_2CO_3$ (15 mmol) and $Pd(PPh_3)_4$ (50 mg) in toluene (10 mL) and $H_2O$ (3 mL) were refluxed under $N_2$ overnight. Upon extraction with diethyl ether, the product was purified by column chromatgraphy.

General method C (alkylation of tetramethyl methylenebisphosphonate): Tetramethyl methylenebisphosphonate (2 mmol) in dry DMF (2 mL) was treated with NaH (2.2 mmol) in ice bath. A benzyl bromide (2 mmol) was added to the resulting solution. The reaction mixture was stirred at room temperature for 1 h before quenched with saturated $NH_4Cl$. The product was extracted with diethyl ether and purified by column chromatography.

General method D (transesterification): The tetramethyl ester of a bisphosphonic acid (1 mmol), NaI (4 mmol) and chloromethyl pivalate (5 mmol) (or chloromethyl isopropyl carbonate when making IPC esters) were refluxed overnight under $N_2$ in dry acetonitrile (5 mL). Upon removal of solvent, the residue was partitioned between water and diethyl ether and the organic layer was washed with water and concentrated. The product was purified by using a flash column chromatography (silica gel, hexane/ethyl acetate: 10/1, then ethyl acetate).

General method E (synthesis of terphenylbisphosphonate): The methyl ester of a carboxylic acid (1 mmol) was hydrolyzed with 3 N NaOH (1 mL) in methanol (5 mL) at room temperature for 1 h. After acidification with 2 N HCl, methanol was removed and the resulting carboxylic acid filtered, then washed with water. The dried acid was dissolved in benzene (5 mL) and oxalyl chloride (2 mmol) added, followed by one drop of DMF. The reaction mixture was stirred for 1 h. Upon removal of solvent, the crude acid chloride obtained was dissolved in dry THF (5 mL) and $P(OTMS)_3$ (2 mmol) added. After 3 h at room temperature, solvent was removed and methanol-$H_2O$ (2 mL, 1:1) was added and the mixture stirred for 30 minutes. Concentrated aqueous NaOH was then added to precipitate the target compound, which was washed thoroughly with methanol then ether and dried to afford the bisphosphonic acids as their sodium salts.

2-(3,4-Dibromophenyl)ethylidene-1,1-bisphosphonic acid (491). Compound 491 was prepared from 3,4-dibromobenzyl bromide (1 mmol) following general method C, followed by hydrolysis with bromotrimethylsilane as a white powder (275 mg, 65% overall yield). Anal. ($C_8H_{10}Br_2O_6P_2$) C, H; $^1$H NMR (400 MHz, $D_2O$): δ 2.78 (tt, J=20.8 Hz, 6.8 Hz, 1H, $ArCH_2CH$), 3.12 (td, J=17.2 Hz, 6.8 Hz, 2H, $ArCH_2$), 7.10 (d, J=8.4 Hz, 1H, aromatic), 7.43 (d, J=8.4 Hz, 1H, aromatic), 7.56 (s, 1H, aromatic); $^{31}$P NMR (162 MHz, $CDCl_3$): δ 19.87.

Tetrakis-pivaloyloxymethyl 2-(3,4-dibromophenyl)ethylidene-1,1-bisphosphonate (493). Compound 493 was prepared from 3,4-dibromobenzyl bromide (1 mmol) following general method C, followed by general method D, as a pale yellow powder (159 mg, 18% overall yield). Anal. ($C_{32}H_{50}Br_2O_{14}P_2$) C, H; $^1$H NMR (400 MHz, $CDCl_3$): δ 1.21 (m, 36H, $CH_3$), 2.79 (tt, J=24.8 Hz, 6.8 Hz, 1H, $ArCH_2CH$), 3.08 (td, J=17.2 Hz, 6.8 Hz, 2H, $ArCH_2$), 5.62-5.69 (m, 8H, $POCH_2$), 7.10 (d, J=8.4 Hz, 1H, aromatic), 7.43 (d, J=8.4 Hz, 1H, aromatic), 7.56 (s, 1H, aromatic); $^{31}$P NMR (162 MHz, CDCl3): δ 20.35.

Tetrakis-pivaloyloxymethyl 2-(3,4-dichlorophenyl)ethylidene-1,1-bisphosphonate (494). Compound 494 was prepared from 3,4-dichlorobenzyl bromide (1 mmol) following general method C, followed by general method D, as a pale yellow powder (153 mg, 21%). Anal. ($C_{32}H_{50}Cl_2O_{14}P_2$) C, H; $^1$H NMR (400 MHz, $CDCl_3$): δ1.21 (m, 36H, $CH_3$), 2.80 (tt, J=24.8 Hz, 6.8 Hz, 1H, $ArCH_2CH$), 3.15 (td, J=17.2 Hz, 6.8 Hz, 2H, $ArCH_2$), 5.62-5.69 (m, 8H, $POCH_2$), 7.10 (d, J=8.4 Hz, 1H, aromatic), 7.33-7.35 (m, 2H, aromatic); $^{31}$P NMR (162 MHz, CDCl3): δ20.41.

Tetrakis-isopropoxycarboxymethyl 2-(3,4-dichlorophenyl)ethylidene-1,1-bisphosphonate (495). Compound 495 was prepared from 3,4-dichlorobenzyl bromide (1 mmol) following general method C, followed by general method D, as a pale yellow powder (136 mg, 17%). Anal. ($C_{28}H_{42}Cl_2O_{18}P_2$) C, H; $^1$H NMR (500 MHz, $CDCl_3$):δ1.32 (d, J=6.4 Hz, 24H, $CH_3$), 2.75 (tt, J=24.4 Hz, 6.4 Hz, 1 H, $ArCH_2CH$), 3.47 (td, J=17.2 Hz, 6.8 Hz, 2H, $ArCH_2$), 4.89-4.95 (m, 4H, $CHMe_2$), 5.60-5.70 (m, 8H, $OCH_2O$), 7.13 (d, J=6.8 Hz, 1H, aromatic), 7.35 (d, J=6.8 Hz, 1 H, aromatic), 7.38 (s, 1 H, aromatic); $^{31}$P NMR (162 MHz, $CDCl_3$): δ 21.85.

Tetrakis-isopropoxycarboxymethyl 2-(3,4-difluorophenyl)ethylidene-1,1-bisphosphonate (496). Compound 496 was prepared from 3,4-difluorobenzyl bromide (1 mmol) following general method C, followed by general method D, as a pale yellow powder (107 mg, 14%). Anal. ($C_{28}H_{42}F_2O_{18}P_2$) C, H; $^1$H NMR (400 MHz, $CDCl_3$): δ 1.33 (d, J=6.4 Hz, 24H, $CH_3$); 2.88 (tt, J=24.4 Hz, J=6.4 Hz, 1 H, $ArCH_2CH$), 3.40 (td, J=17.2 Hz, 6.8 Hz, 2H, $ArCH_2$), 4.89-4.95 (m, 4H, $CHMe_2$), 5.60-5.72 (m, 8H, $OCH_2O$), 6.99-7.13 (m, 3H, aromatic); $^{31}$P NMR (162 MHz, $CDCl_3$): δ 21.94. $^{19}$F NMR (376 MHz, $CDCl_3$): −−140.79~−140.67 (m, 1F), −138.08~−137.97 (m, 1F).

Tetrakis-isopropoxycarboxymethyl 2-(3-cyanophenyl)ethylidene-1,1-bisphosphonate (498). Compound 498 was prepared from 3-cyanobenzyl bromide (1 mmol) following general method C, followed by general method D, as a pale yellow powder (91 mg, 12%). Anal. ($C_{29}H_{43}NO_{18}P_2$) C, H, N; $^1$H NMR (400 MHz, $CDCl_3$): δ 1.31 (d, J=6.4 Hz, 24H, $CH_3$), 2.79 (tt, J=20.8 Hz, J=6.8 Hz, 1 H, $ArCH_2CH$), 3.40 (td, J=16.8 Hz, 6.8 Hz, 2H, $ArCH_2$), 4.89-4.96 (m, 4H, $CHMe_2$), 5.60-5.70 (m, 8H, $OCH_2O$), 7.36 (t, J=8 Hz, 1H, aromatic), 7.50-7.54 (m, 2H, aromatic), 7.57 (s, 1 H, aromatic); $^{31}$P NMR (162 MHz, $CDCl_3$): δ 21.70.

1-Hydroxy-2-[3-(3-phenylphenyl)phenyl]ethylidene-1,1-bisphsophonic acid (608). Compound 608 was prepared from methyl 3-(3-phenylphenyl)phenylacetate (1 mmol), following general method E as a white powder (265 mg, 56%). Anal. ($C_{20}H_{19}NaO_7P_2 \cdot H_2O$) C, H; $^1$H NMR (400 MHz, $D_2O$): δ3.23 (t, J=12 Hz, 2H, $CH_2$), 7.20-7.80 (m, 13H, aromatic); $^{31}$P NMR (162 Hz, $D_2O$): δ 19.20.

1-Hydroxy-3-[3-(4-phenylphenyl)phenyl]propylidene-1,1-bisphosphonic acid (618). Compound 618 was prepared from methyl 3-(4-phenylphenyl) phenylpropionate (1 mmol), following general method E as a white powder (270 mg, 55%). Anal. ($C_{21}H_{20}O_7P_2Na_2$) C, H; $^1$H NMR (400 MHz, $D_2O$): δ 2.05-2.10 (m, 2H, $CH_2$), 2.80-2.85 (m, 2H, $ArCH_2$), 7.22-7.32 (m, 6H, aromatic), 7.35-7.64 (m, 7H, aromatic); $^{31}$P NMR (162 MHz, $D_2O$): δ 19.08.

1-Hydroxy-3-[3-(2-phenylphenyl)phenyl]propylidene-1,1-bisphosphonic acid (621). Compound 621 was prepared from methyl3-(2-phenylphenyl) phenylpropioate (1 mmol), following general method E as a white powder (271 mg, 51%). Anal. ($C_{21}H_{19}O_7P_2Na_3 \cdot H_2O$) C, H; $^1$H NMR (500 MHz, $D_2O$): δ1.98-2.10 (m, 2H, $CH_2$), 2.69-2.72 (m, 2H, $ArCH_2$), 6.70 (d, J=6.5 Hz, 1H, aromatic), 6.97 (t, J=7.5 Hz, 1H, aromatic), 7.04-7.17 (m, 7H, aromatic), 7.32-7.45 (m, 4H, aromatic). $^{31}$P NMR (202 MHz, $D_2O$): δ 19.38.

1-Hydroxy-3-[3-(3-phenylphenyl)phenyl]propylidene-1,1-bisphsophonic acid (622). Compound 622 was prepared from methyl 3-(3-phenylphenyl) phenylpropioate (1 mmol), following general method E as a white powder (324 mg, 61%). Anal. ($C_{21}H_{19}O_7P_2Na_3 \cdot H_2O$) C, H; $^1$H NMR (400 Hz, $D_2O$): δ 2.01-2.12 (m, 2H, $CH_2$), 2.80-2.85 (m, 2H, Ar$CH_2$), 7.23-7.57 (m, 12H, aromatic), 7.77 (s,1 H, aromatic); $^{31}$P NMR (162 Hz, $D_2O$): δ 19.41.

1-Hydroxy-2-[3-(2-phenylphenyl)phenyl]ethylidene-1,1-bisphsophonic acid (623). Compound 623 was prepared from methyl 3-(2-phenylphenyl)phenylacetate (1 mmol), following general method E as a white powder (213 mg, 43%). Anal. ($C_{20}H_{18}O_7P_2Na_2 \cdot H_2O$) C, H; $^1$H NMR (400 MHz, $D_2O$): δ 3.10 (t, J=12 Hz, 2H, $CH_2$), 6.73-7.40 (m,13H, aromatic). $^{31}$P NMR (162 Hz, $D_2O$): δ 19.23.

1-Hydroxy-2-[4-(2-phenylphenyl)phenyl]ethylidene-1,1-bisphosphonic acid (624). Compound 624 was prepared from methyl 4-(2-phenylphenyl)phenylacetate (1 mmol), following general method E as a white powder (232 mg, 45%). Anal. ($C_{20}H_{18}O_7P_2Na_2 \cdot 2H_2O$) C, H; $^1$H NMR (400 MHz, $D_2O$) δ 3.06 (t, J=12.4 Hz, $CH_2$), 6.94 (d, J=8 Hz, 2H, aromatic), 7.01-7.07 (m, 2H, aromatic), 7.11-7.17 (m, 4H, aromatic), 7.30-7.39 (m, 5H, aromatic); $^{31}$P NMR (162 MHz, $D_2O$): δ 18.97.

1-Hydroxy-2-[4-(3-phenylphenyl)phenyl]ethylidene-1,1-bisphsophonic acid (625). Compound 625 was prepared from methyl 4-(3-phenylphenyl)phenylacetate (1 mmol), following general method E as a white powder (201 mg, 44%). Anal. ($C_{20}H_{19}O_7P_2Na$) C, H; $^1$H NMR (400 MHz, $D_2O$) δ 3.21 (t, J=12.4 Hz, $CH_2$), 7.27 (t, J=7.2 Hz, 1H, aromatic), 7.34-7.60 (m, 11H, aromatic), 7.80 (s, 1H, aromatic); $^{31}$P NMR (162 MHz, $D_2O$): δ 19.11.

1-Hydroxy-[3-(3-phenylphenyl)phenyl]methylene-1,1-bisphsophonic acid (640). Compound 640 was prepared from methyl 3-(3-phenylphenyl)benzoate (1 mmol), following general method E as a white powder (174 mg, 40%). Anal. ($C_{19}H_{17}O_7P_2Na \cdot 0.25H_2O$) C, H; $^1$H NMR (400 MHz, $D_2O$): δ 7.17-7.25 (m, 2H, aromatic), 7.33 (t, $J_{H-H}$=7.2 Hz, 2H, aromatic), 7.40 (t, J=8 Hz, 1H, aromatic), 7.47 (d, J=7.8 Hz, 1H, aromatic), 7.56-7.58 (m, 4H, aromatic), 7.65(d, J=8 Hz, 1 H, aromatic), 7.83 (s, 2H, aromatic); $^{31}$P NMR (162 MHz, $D_2O$): δ 17.59.

Tetrakis-pivaloyloxymethyl 2-[3-(3-phenylphenyl)phenyl]ethylidene-1,1-bisphosphonate (647). 3-biphenyl boronic acid (2.0 g, 10 mmol), 3-bromotoluene (1.7 g, 10 mmol), $K_2CO_3$ (3.0 g, 21.7 mmol) and Pd(PPh$_3$)$_4$ (100 mg) were refluxed in toluene-$H_2O$ (50 mL, 5/1) overnight under $N_2$. Upon extraction with diethyl ether, the crude product was then refluxed overnight with N-bromosuccimide (1.95 g, 11 mmol) and AIBN (100 mg) in anhydrous $CCl_4$ (30 mL). After being washed successively with 5% HCl then 10% NaHCO$_3$, the organic layer was dried and concentrated to give crude 3-(3-phenylphenyl)benzyl bromide as a white powder. This was then reacted following general method C, followed by general method D, affording compound 647 as a pale yellow powder (472 mg, 27% overall yield). Quantative $^1$H NMR indicated 94% purity. $^1$H NMR (400 MHz, CDCl$_3$): δ 1.21 (m, 36H, $CH_3$), 2.80 (tt, J=24.8 Hz, 6.8 Hz, 1 H, Ar$CH_2$CH), 3.15 (td, J=17.2 Hz, 6.8 Hz, 2H, Ar$CH_2$), 5.62-5.69 (m, 8H, POC$H_2$), 7.23-7.85 (m, 13H, aromatic); $^{31}$P NMR (162 MHz, CDCl3): 6 20.52.

2-(3-Cyanophenyl)ethylidene-1,1-bisphosphonic acid (648). Compound 648 was prepared from 3-cyanobenzyl bromide (1 mmol) following general method C, followed by hydrolysis with bromotrimethylsilane as a white powder (29%). Anal. ($C_9H_8NNa_3O_6P_2 \cdot H_2O$) C, H, N; $^1$H NMR (400 MHz, $D_2O$):δ2.79 (tt, J=20.8 Hz, 6.8 Hz, 1H, Ar$CH_2$CH), 3.40 (td, J=16.8 Hz, 6.8 Hz, 2H, Ar$CH_2$), 4.89-4.96 (m,4H, C$H$Me$_2$), 5.60-5.70 (m, 8H, OC$H_2$), 7.39 (t, J=8 Hz, 1H, aromatic); 7.45-7.52 (m, 2H, aromatic), 7.59 (s, 1H, aromatic); $^{31}$P NMR (162 MHz, $D_2O$): δ 19.81.

TABLE 3

Elemental analysis results for bisphosphonate compounds.

| | | Calculated | | | Found | | |
|---|---|---|---|---|---|---|---|
| Compound | Formula | C (%) | H (%) | N (%) | C (%) | H (%) | N (%) |
| 9 | $C_{13}H_{13}FNNaO_7P_3$ | 39.11 | 3.28 | 3.51 | 39.16 | 3.65 | 3.51 |
| 10 | $C_{14}H_{15}F_3NNa_2O_{8.5}P_2$ | 33.75 | 3.03 | 2.81 | 33.99 | 3.38 | 2.76 |
| 11 | $C_{11}H_{19.5}NO_{7.25}P_2$ | 38.44 | 5.72 | 4.08 | 38.29 | 5.49 | 4.11 |
| 14 | $C_{19}H_{39}NO_6P_3$ | 54.42 | 4.57 | 3.34 | 54.27 | 4.37 | 3.30 |
| 15 | $C_{11}H_{30}NO_{6.5}P_2$ | 39.77 | 6.07 | 4.22 | 39.72 | 6.00 | 4.00 |
| 16 | $C_{13}H_{35}NO_6P_2$ | 45.49 | 4.41 | 4.08 | 45.09 | 4.31 | 4.08 |
| 19 | $C_7H_{11}BrNNaO_3P_2$ | 20.91 | 2.76 | 3.48 | 20.75 | 2.61 | 3.17 |
| 20 | $C_8H_{14.5}NO_{6.75}P_2$ | 32.61 | 4.96 | 4.75 | 32.63 | 4.86 | 4.62 |
| 21 | $C_9H_{24}NNaO_6P_2$ | 34.08 | 4.45 | 4.42 | 33.79 | 4.69 | 4.28 |
| 28 | $C_7H_{13}ClNO_{6.5}P_2$ | 27.07 | 3.57 | 4.51 | 26.86 | 3.37 | 4.34 |
| 29 | $C_7H_{21.5}NO_{6.25}P_2$ | 30.95 | 4.27 | 5.16 | 30.92 | 4.11 | 5.11 |
| 30 | $C_7H_{23}ClNO_{6.5}P_2$ | 27.07 | 3.57 | 4.51 | 26.86 | 3.37 | 4.34 |
| 31 | $C_7H_{10}INO_6P_2$ | 21.39 | 2.56 | 3.56 | 21.29 | 2.20 | 3.43 |
| 32 | $C_7H_{10}BrNO_6P_2$ | 24.30 | 2.91 | 4.05 | 24.00 | 2.73 | 3.80 |
| 33 | $C_{14}H_{26.25}NNa_{0.75}O_6P_2$ | 44.99 | 4.38 | 3.75 | 44.93 | 4.42 | 3.79 |
| 34 | $C_9H_{10}F_3NO_6P_2$ | 28.76 | 3.01 | 4.18 | 28.41 | 2.92 | 3.97 |
| 39 | $C_{19}H_{29}NO_6P_2$ | 54.42 | 4.57 | 3.34 | 54.24 | 4.47 | 3.30 |
| 40 | $C_{12}H_{17}NO_9P_2$ | 39.46 | 4.69 | 3.84 | 39.33 | 4.50 | 3.82 |
| 41 | $C_{19}H_{29.6}NO_{6.3}P_3$ | 53.73 | 4.65 | 3.30 | 53.38 | 4.47 | 3.37 |
| 42 | $C_{12}H_{27}NO_3P_2$ | 39.46 | 4.69 | 3.84 | 39.03 | 4.31 | 4.00 |
| 44 | $C_{13}H_{28}NO_{2.5}P_2$ | 40.43 | 4.70 | 3.63 | 40.34 | 4.49 | 3.25 |
| 46 | $C_3H_{13}NO_8P_2$ | 30.68 | 4.18 | 4.47 | 30.32 | 4.05 | 4.38 |
| 49 | $C_{12}H_{18}N_3NaO_{9.5}P_2$ | 33.74 | 4.25 | 6.56 | 33.93 | 4.12 | 6.18 |
| 50 | $C_{11}H_{14}NO_{6.5}P_2$ | 40.50 | 4.33 | 4.29 | 40.64 | 4.11 | 4.30 |
| 51 | $C_3H_{12}P_3NO_{6.5}P_2$ | 27.92 | 3.22 | 4.07 | 27.72 | 3.00 | 4.04 |
| 52 | $C_{11}H_{19}N_3O_{8.5}P_2S$ | 32.28 | 4.68 | 6.84 | 32.13 | 4.38 | 6.62 |
| 53 | $C_{19}H_{29}NO_6P_2$ | 54.42 | 4.57 | 3.34 | 54.19 | 4.00 | 3.28 |

TABLE 3-continued

Elemental analysis results for bisphosphonate compounds.

| Compound | Formula | Calculated | | | Found | | |
|---|---|---|---|---|---|---|---|
| | | C (%) | H (%) | N (%) | C (%) | H (%) | N (%) |
| 54 | $C_{19}H_{29}NNaO_{6.5}P_2$ | 50.68 | 4.25 | 3.11 | 50.43 | 4.13 | 3.17 |
| 56 | $C_{21}H_{23}Na_3O_8P_2$ | 47.38 | 3.98 | | 47.53 | 3.75 | |
| 57 | $C_{26}H_{20}Na_3O_8P_2$ | 48.40 | 4.06 | | 48.61 | 4.21 | |
| 58 | $C_{26}H_{23}NaO_8P_2$ | 50.64 | 4.46 | | 50.70 | 4.35 | |
| 59 | $C_{21}H_{23}Na_2O_{7.5}P_2$ | 50.31 | 4.22 | | 50.02 | 3.93 | |
| 60 | $C_{21}H_{20}Na_2O_7P_2$ | 51.23 | 4.09 | | 51.22 | 4.47 | |
| 61 | $C_{19}H_{17.5}NaO_{7.25}P_2$ | 51.08 | 3.95 | | 50.92 | 3.68 | |
| 62 | $C_{26}H_{29}NaO_7P_2$ | 52.64 | 52.63 | | 4.20 | 4.14 | |
| 63 | $C_{26}H_{22}Na_2O_9P_2$ | 46.71 | 4.31 | | 46.63 | 4.42 | |
| 64 | $C_{32}H_{50}Br_2O_{14}P_2$ | 43.65 | 5.72 | | 43.81 | 5.52 | |
| 65 | $C_{32}H_{50}Cl_2O_{14}P_2$ | 48.55 | 6.37 | | 48.65 | 4.37 | |
| 66 | $C_{28}H_{42}Cl_2O_{18}P_2$ | 42.07 | 5.30 | | 41.71 | 5.41 | |
| 67 | $C_{22}H_{42}F_2O_{12}P_2$ | 43.87 | 5.52 | | 43.80 | 5.43 | |
| 68 | $C_{29}H_{43}NO_{15}P_2$ | 46.10 | 5.74 | | 46.03 | 5.79 | |
| 69 | $C_6H_{19}Br_2O_6P_2$ | 22.67 | 2.38 | | 22.78 | 2.42 | |
| 70 | $C_9H_{10}NNa_3O_7P_2$ | 28.82 | 2.69 | | 28.83 | 2.76 | |

EXAMPLE 3

Sulfonium and Phosphonium Bisphosphonates

Figure 4:
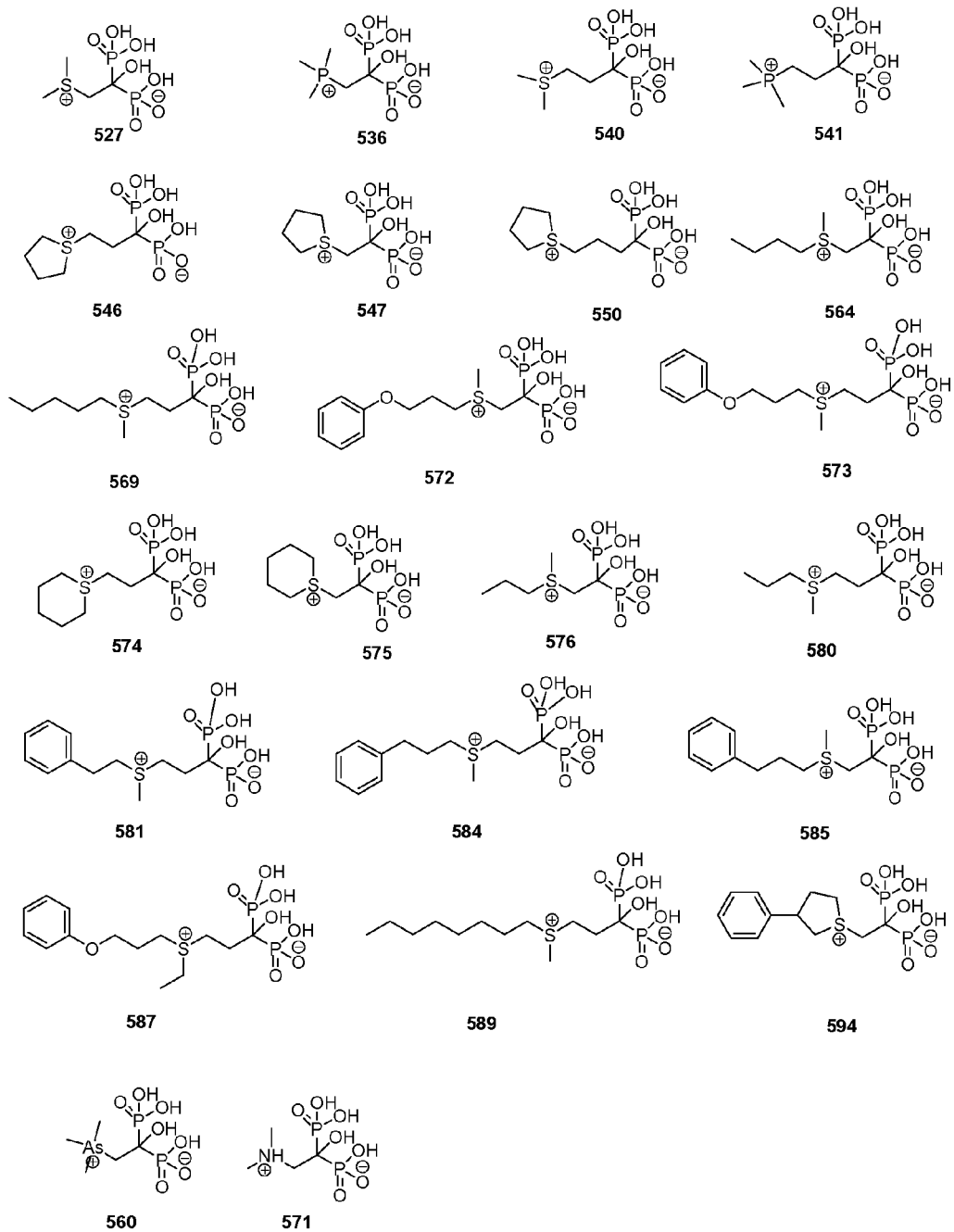
FIG. 4 illustrates structures of certain bisphosphonate compounds including sulfonium, phosphonium, arsonium, and ammonium analogs.
Figure 5:
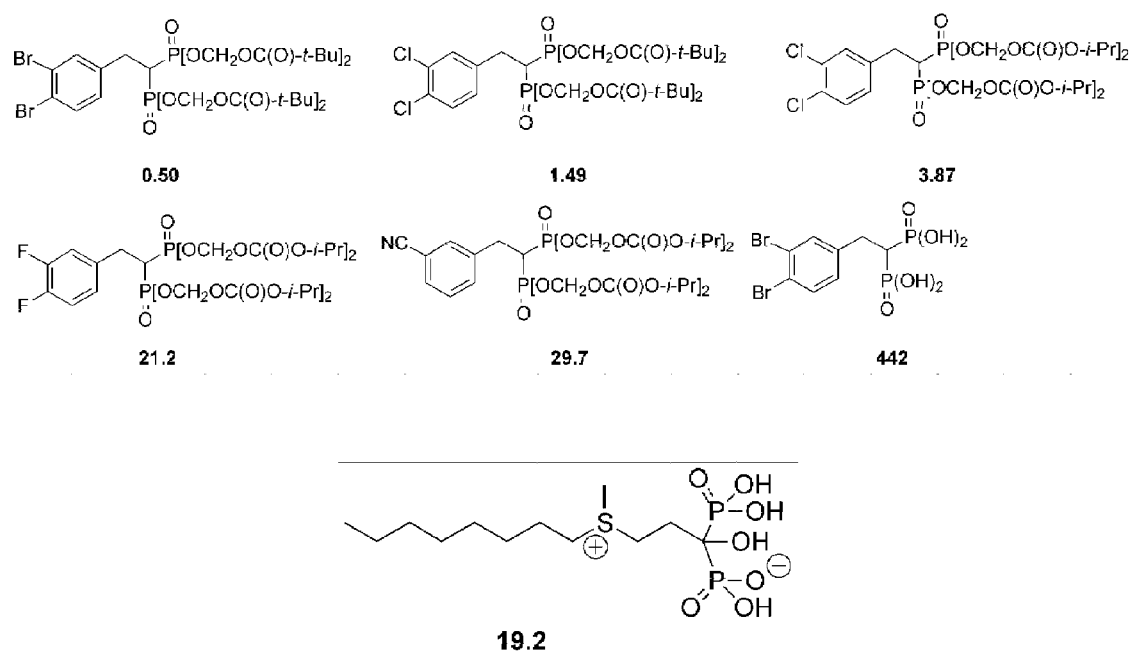
FIG. 5 illustrates structures of bisphosphonate compounds along with activity levels (micromolar IC50 values, μM) of non-nitrogen-containing benzyl bisphosphonates (upper group); and a sulfonium-bisphosphonate. Activity levels represent the capability to inhibit growth of three tumor cell lines: human breast cancer (MCF7), human lung cancer (NCIH460) and human CNS cancer (SF268). Values shown are the mean for the three cell lines.

A series of novel sulfonium and phosphonium bisphosphonates were produced by using the following general schemes presented below. The synthesis of arsonium and ammonium compounds are able to be achieved as taught herein and by analogy as would be understood in the art. See FIG. 4 illustrating structures of compounds including sulfonium, phosphonium, arsonium, and ammonium analogs.

These bisphosphonates were found to have activity against *Trypanosoma brucei* FPPS (anti-parasitic activity), human FPPS (bone resorption assay), *D. dictyostelium* (bone resorption assay) and in gamma delta T cell stimulation (immunotherapy assay), as shown in the following Table 4.

Table 4. Activity of bisphosphonate compounds in multiple functional tests.

TABLE 4

Activity of bisphosphonate compounds in multiple functional tests.

| Compound | Compound Alias | *T. brucei* FPPS IC50 (μm) | *D. discoideum* IC50 (μm) | Human FPPS Ki (nM) | Gammadelta T cell stimulation, $EC_{50}$ |
|---|---|---|---|---|---|
| 1 (Pamidronate) | | | 167 | | 940 |
| 2 (alendronate) | | | 32 | | 52 |
| 3 (risedronate) | | 0.1 | 2.8 | 1.23 | 6.2 |
| 4 (zoledronate) | | 0.32 | 1.9 | 1.25 | 7.3 |
| 5 | | | | | |
| 6 | 527 | 0.4 | 4.78 | | 22.11 |
| 7 | 536 | 2 | 13.8 | 8.18 | 127.2 |
| 8 | 540 | 1.4 | 7.51 | 5.24 | 23.68 |
| 9 | 541 | | 207 | 22.63 | 1799 |
| 10 | 546 | 0.78 | 5.62 | 2.92 | 26.02 |
| 11 | 547 | 0.25 | 5.95 | 3.54 | 17.32 |
| 12 | 550 | | 101 | 9.84 | 375.6 |
| 13 | 564 | 1.1 | 8.30 | 4.34 | 260.9 |
| 14 | 569 | | 7.96 | | 78.72 |
| 15 | 572 | 0.24 | 8.87 | 3.44 | 217 |
| 16 | 573 | | 4.23 | 5.20 | 199 |
| 17 | 574 | | 13.4 | 3.51 | 199.6 |
| 18 | 575 | 0.59 | 6.58 | 3.42 | 75.52 |
| 19 | 576 | | 11.2 | 5.14 | 51.97 |
| 20 | 580 | | 14.6 | 3.36 | 43.52 |
| 21 | 581 | | 5.73 | 4.92 | 308.7 |
| 22 | 584 | | 2.05 | | 119 |
| 23 | 585 | 0.18 | 1.85 | 5.68 | |
| 24 | 587 | | 1.34 | 15.74 | 665 |
| 25 | 589 | | 4.94 | 12.48 | 96.40 |
| 26 | 594 | | 7.15 | 13.94 | 413.8 |

Synthesis of bisphosphonates including sulfonium and phosphonium analogs.

Scheme 4. Preparation of the Sulfonium diphosphonic acids (I)

4a) Preparation of sulfides

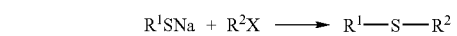

$R^1, R^2$ = alkyl
X = Br, I

4b) Preparation of 1-hydroxy-2-(substituted sulfonium-1-yl)ethyl-1,1-diphosphonic acid.

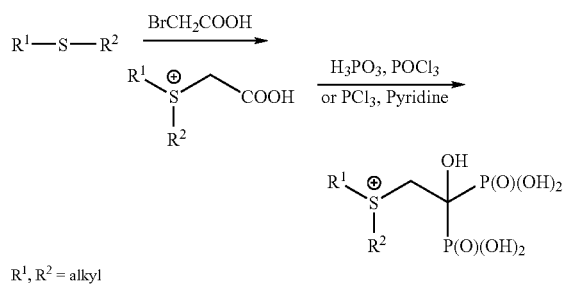

$R^1, R^2$ = alkyl

4c) Preparation of 1-hydroxy-3-(substituted sulfonium-1-yl)propyl-1,1-diphosphonic acid

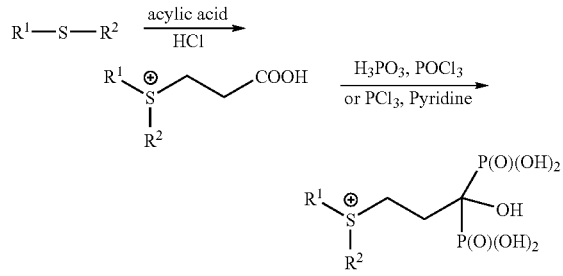

Scheme 5. Preparation of phosphonium diphosphonic acid

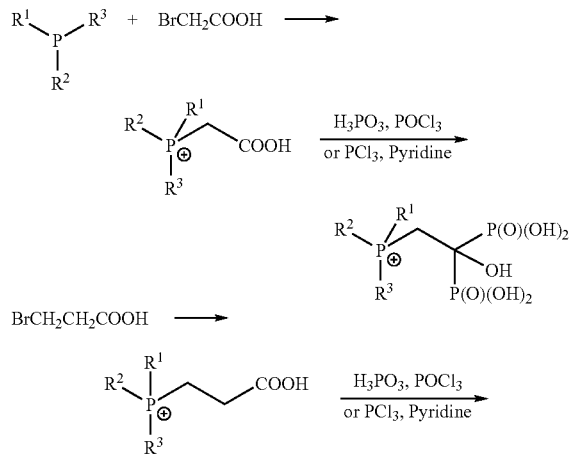

-continued

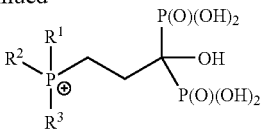

$R^1, R^2, R^3$ = alkyl

General procedure 1: A mixture of a carboxylic acid (3 mmol), $H_3PO_3$ (15 mmol) and toluene (8 mL) were heated to 80° C. with stirring. After all solids were melted, $POCl_3$ (15 mmol) was added slowly and the reaction mixture was vigorously stirred at 80° C. for 5 h . Upon cooling, toluene was decanted and 6 N HCl (3 mL) was added to the residue. The resulting solution was refluxed for 1 h and most of the solvents were removed in vacuo. Isopropanol (25 mL) was added to precipitate the bisphosphonate as a white powder, which was filtered, washed with isopropanol (5×5 mL), dried and could be further purified by recrystallization in $H_2O$/i-PrOH. In some cases, it can be neutralized with NaOH and crystallized as its sodium salt in $H_2O$/EtOH.

EXAMPLE A 1-hydroxy-2-(trimethylphosphoniumyl)ethylidene-1, 1-bisphosphonic acid (536)

Trimethyl phosphine (5 mmol, 0.52 mL) was treated with bromoacetic acid (5 mmol, 0.7 g) in acetonitrile (5 mL) at room temperature under $N_2$ overnight, affording 2-trimethylphosphoniumylacetic acid bromide as a white powder. It was then subjected to the general procedure 1 to give compound 536 as a white powder (0.65 g, 46% overall yield). Anal. ($C_5H_{15}O_7P_3$) C, H.

EXAMPLE B 1-hydroxy-3-(trimethylphosphoniumyl)propylidene-1,1-bisphosphonic acid (541)

Trimethyl phosphine (5 mmol, 0.52 mL) was treated with bromopropionic acid (5 mmol, 0.77 g) in acetonitrile (10 mL) at 80° C. under $N_2$ overnight, affording 3-trimethylphosphoniumylpropionic acid bromide as a white powder. It was then subjected to the general procedure 1 to give compound 541 as a white powder (0.46 g, 40% overall yield). Anal. ($C_6H_{17}O_7P_3.0.5 H_2O$) C, H.

EXAMPLE C 1-hydroxy-2-(pentamethylenesulfoniumyl)ethylidene-1,1-bisphosphonic acid (527)

dimethyl sulfide (5 mmol, 0.51 g) was treated with bromoacetic acid (5 mmol, 0.7 g) in acetone (5 mL) at room temperature under $N_2$ overnight, affording 2- pentamethylenesulfoniumylacetic acid bromide as a white powder. It was then subjected to the general procedure 1 to give compound 3 as a white powder (0.68 g, 38% overall yield). Anal. ($C_7H_{16}O_7P_2S$) C, H.

EXAMPLE D 1-hydroxy-2-(S-methyl-3-phenylpropylsulfoniumyl) ethylidene-1,1-bisphosphonic acid (585)

Sodium methanethiolate (6 mmol, 0.42 g) and 3-phenylpropyl bromide (5 mmol, 1 g) in methanol were refluxed overnight. After removal of solvent, diethyl ether was added, washed with $H_2O$ and evaporated to give 3-phenylpropylmethyl sulfide. It was then reacted with equivalent amount of bromoacetic acid in acetonitrile (5 mL) at room temperature under $N_2$ overnight, affording S-methyl-3-phenylpropylsulfoniumylacetic acid bromide as a white powder. It was then subjected to the general procedure 1 to give compound 585 as a white powder (0.75 g, 36% overall yield). Anal. ($C_{12}H_{19}NaO_7P_2S.0.5\ C_2H_5OH$) C, H.

EXAMPLE E 1-hydroxy-3-(S-ethyl-3-phenoxypropylsulfoniumyl) propylidene-1,1-bisphosphonic acid (573)

Sodium ethanethiolate (6 mmol, 0.5 g) and 3-phenoxypropyl bromide (5 mmol, 1.1 g) in ethanol were refluxed overnight. After removal of solvent, Ether was added, washed with $H_2O$ and evaporated to give 3-phenoxypropylethyl sulfide. It was treated with 1 equivalent of acrylic acid in acetone in the presence of 4 equivalents of 12 N HCl under $N_2$ at room temperature overnight and then at 50° C. for 3 h, affording 3-(S-ethyl-3-phenoxypropylsulfoniumyl)propionic acid chloride as a white powder. It was then subjected to the general procedure 1 to give compound 573 as a white powder (0.58 g, 25% overall yield). Anal. ($C_{14}H_{22}Na_2O_8P_2S.0.5\ H_2O$) C, H.

EXAMPLE 4

Further Bisphosphonate Compounds

In embodiments, the invention provides compounds having the formula CA11:

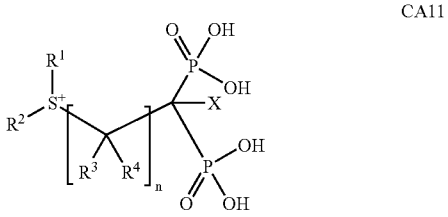

CA11 which can be in zwitterionic form (e.g., wherein one, and under certain circumstances more than one, of the OH groups of a phosphonate moiety can be depicted as an oxygen group with a negative charge) and/or as a pharmaceutically acceptable salt, ester, or hydrate thereof, with variations as would be understood from the teaching herein for other general formulas presented;

wherein:

X is H or —OH;

n is 1, 2, or 3;

$R^1$ and $R^2$, independently of one another and other R groups, are selected from the group consisting of a hydrogen, a halogen, a —CN, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, and an optionally substituted aryl group, where each R, independent of any other R in any listed group, is selected from H, an optionally substituted alkyl group, an optionally substituted aryl group, and an optionally substituted acyl group;

$R^1$ and $R^2$ can together form one or more rings which may contain one or more double bonds or which may be aromatic;

$R^3$ and $R^4$, independently of each other and other $R^3$ and $R^4$ in the compound, are selected from the group consisting of a hydrogen, a halogen, a —N(R)$_2$, or —SR group, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group; and wherein $R^3$ and $R^4$ can together form a ring which may contain one or more double bonds.

In specific embodiments, the invention relates to compounds having the above formula where X is OH.

In other specific embodiments, the invention relates to compounds having the above formula where X is H.

In other specific embodiments, compounds of the invention are those of formula CA11.

In other specific embodiments, the invention relates to compounds having the above formula wherein n is 1.

In other specific embodiments, the invention relates to compounds having the above formula where X is OH and n is 1.

In other specific embodiments, the invention relates to compounds having the above formula wherein n is 2.

In other specific embodiments, the invention relates to compounds having the above formula where X is OH and n is 2.

In other specific embodiments, the invention relates to compounds having the above formula wherein n is 3.

In other specific embodiments, the invention relates to compounds having the above formula where X is OH and n is 3.

In other specific embodiments, the invention relates to compounds having the above formula wherein one or both of $R^3$ and $R^4$ are hydrogens.

In other specific embodiments, the invention relates to compounds having the above formula wherein both of $R^3$ and $R^4$ are hydrogens.

In other specific embodiments, the invention relates to compounds having the above formula wherein both of $R^3$ and $R^4$ are hydrogens and n is 1.

In other specific embodiments, the invention relates to compounds having the above formula wherein both of $R^3$ and $R^4$ are hydrogens, n is 1 and X is OH.

In other specific embodiments, the invention relates to compounds having the above formula wherein both of $R^3$ and $R^4$ are hydrogens and n is 2.

In other specific embodiments, the invention relates to compounds having the above formula wherein both of $R^3$ and $R^4$ are hydrogens, n is 2 and X is OH.

In other specific embodiments, the invention relates to compounds having the above formula wherein both of $R^3$ and $R^4$ are hydrogens and n is 3.

In other specific embodiments, the invention relates to compounds having the above formula wherein both of $R^3$ and $R^4$ are hydrogens, n is 3 and X is OH.

In other specific embodiments, the invention relates to compounds having the above formula wherein both of $R^3$ and $R^4$ are hydrogens, n is 1 and X is H.

In other specific embodiments, the invention relates to compounds having the above formula wherein $R^1$ and $R^2$, independently of one another, are optionally substituted alkyl groups.

In other specific embodiments, the invention relates to compounds having the above formula wherein $R^1$ and $R^2$, independently of one another, are optionally substituted alkyl groups, X is OH and n is 1.

In other specific embodiments, the invention relates to compounds having the above formula wherein $R^1$ and $R^2$, independently of one another, are optionally substituted alkyl groups, X is OH and n is 2.

In other specific embodiments, the invention relates to compounds having the above formula wherein $R^1$ and $R^2$, independently of one another, are optionally substituted alkyl groups, X is OH and n is 3.

In other specific embodiments, the invention relates to compounds having the above formula wherein $R^1$ and $R^2$ are optionally substituted alkyl groups, X is H and n is 1.

In other specific embodiments, the invention relates to compounds having the above formula wherein $R^1$ and $R^2$, independently of one another, are both optionally substituted alkyl groups.

In other specific embodiments, the invention relates to compounds having the above formula wherein $R^1$ and $R^2$, independently of one another, are both optionally substituted alkyl groups, X is OH and n is 1.

In other specific embodiments, the invention relates to compounds having the above formula wherein $R^1$ and $R^2$, independently of one another, are both optionally substituted alkyl groups, X is OH and n is 2.

In other specific embodiments, the invention relates to compounds having the above formula wherein $R^1$ and $R^2$, independently of one another, are both optionally substituted alkyl groups, X is OH and n is 3.

In other specific embodiments, the invention relates to compounds having the above formula wherein $R^1$ and $R^2$ are both optionally substituted alkyl groups, X is H and n is 1.

In other specific embodiments, the invention relates to compounds having the above formula wherein $R^1$ and $R^2$ are both optionally substituted alkyl groups and one or more of $R^3$ or $R^4$ is a halogen.

In other specific embodiments, the invention relates to compounds having the above formula wherein $R^1$ and $R^2$ are both optionally substituted alkyl groups, particularly wherein $R^1$ is a small alkyl group and more particularly a methyl group, and $R^3$ and $R^4$ are both hydrogens.

In other specific embodiments, the invention relates to compounds having the above formula wherein $R^1$ and $R^2$ are both optionally substituted alkyl groups, particularly wherein $R^1$ is a small alkyl group and more particularly a methyl group, $R^3$ and $R^4$ are both hydrogens, X is OH and n is 1. Specific compounds of this invention are those as above in which $R^1$ is a methyl group, $R^2$ is an optionally substituted alkyl group, $R^3$ and $R^4$ are both hydrogens, X is OH and n is 1. A specific compound of this invention is that as above in which $R^1$ and $R^2$ are both methyl groups, $R^3$ and $R^4$ are both hydrogens, X is OH and n is 1. A specific compound of this invention is that as above in which $R^1$ is a methyl group, $R^2$ is a propyl group, $R^3$ and $R^4$ are both hydrogens, X is OH and n is 1. A specific compound of this invention is that as above in which $R^1$ is a methyl group, $R^2$ is a butyl group, $R^3$ and $R^4$ are both hydrogens, X is OH and n is 1. A specific compound of this invention is that as above in which $R^1$ is a methyl group, $R^2$ is a pentyl group, $R^3$ and $R^4$ are both hydrogens, X is OH and n is 1. A specific compound of this invention is that as above in which $R^1$ is a methyl group, $R^2$ is an octyl group, $R^3$ and $R^4$ are both hydrogens, X is OH and n is 1.

In other specific embodiments, the invention relates to compounds having the above formula wherein $R^1$ and $R^2$ are both optionally substituted alkyl groups, particularly wherein $R^1$ is a small alkyl group and more particularly a methyl group, $R^3$ and $R^4$ are both hydrogens, X is OH and n is 2. Specific compounds of this invention are those as above in which $R^1$ is a methyl group, $R^2$ is an optionally substituted alkyl group, $R^3$ and $R^4$ are both hydrogens, X is OH and n is 2. A specific compound of this invention is that as above in which $R^1$ and $R^2$ are both methyl groups, $R^3$ and $R^4$ are both hydrogens, X is OH and n is 2. A specific compound of this invention is that as above in which $R^1$ is a methyl group, $R^2$ is a propyl group, $R^3$ and $R^4$ are both hydrogens, X is OH and n is 2. A specific compound of this invention is that as above in which $R^1$ is a methyl group, $R^2$ is a pentyl group, $R^3$ and $R^4$ are both hydrogens, X is OH and n is 2. A specific compound of this invention is that as above in which $R^1$ is a methyl group, $R^2$ is an octyl group, $R^3$ and $R^4$ are both hydrogens, X is OH and n is 2.

In other specific embodiments, the invention relates to compounds having the above formula wherein $R^1$ is a small alkyl group and more particularly a methyl group, $R^2$ is an optionally substituted arylalkyl group, $R^3$ and $R^4$ are both hydrogens, X is OH and n is 1. Specific compounds of the invention are those as above in which $R^1$ is a methyl group, $R^2$ is an optionally substituted arylalkyl group, $R^3$ and $R^4$ are both hydrogens, X is OH and n is 1. A specific compound of the invention is that as above in which $R^1$ is a methyl group, $R^2$ is a propylphenyl group, $R^3$ and $R^4$ are both hydrogens, X is OH and n is 1.

In other specific embodiments, the invention relates to compounds having the above formula wherein $R^1$ is a small alkyl group and more particularly a methyl group, $R^2$ is an optionally substituted arylalkyl group, $R^3$ and $R^4$ are both hydrogens, X is OH and n is 2. A specific compound of this invention is that as above in which $R^1$ is a methyl group, $R^2$ is an ethylphenyl group, $R^3$ and $R^4$ are both hydrogens, X is OH and n is 2. A specific compound of this invention is that as above in which $R^1$ is a methyl group, $R^2$ is a propylphenyl group, $R^3$ and $R^4$ are both hydrogens, X is OH and n is 2.

In other specific embodiments, the invention relates to compounds having the above formula wherein $R^1$ is a small alkyl group and more particularly a methyl group, $R^2$ is an optionally substituted arylalkoxy group, $R^3$ and $R^4$ are both hydrogens, X is OH and n is 1. Specific compounds of the invention are those as above in which $R^1$ is a methyl group, $R^2$ is an optionally substituted arylalkoxy group, $R^3$ and $R^4$ are both hydrogens, X is OH and n is 1. A specific compound of the invention is that as above in which $R^1$ is a methyl group, $R^2$ is a propoxybenzyl group, $R^3$ and $R^4$ are both hydrogens, X is OH and n is 1.

In other specific embodiments, the invention relates to compounds having the above formula wherein $R^1$ is a small alkyl group and more particularly a methyl group, $R^2$ is an optionally substituted arylalkoxy group, $R^3$ and $R^4$ are both hydrogens, X is OH and n is 2. Specific compounds of the invention are those as above in which $R^1$ is a methyl group, $R^2$ is an optionally substituted arylalkoxy group, $R^3$ and $R^4$ are both hydrogens, X is OH and n is 2. A specific compound of the invention is that as above in which $R^1$ is a methyl group, $R^2$ is a propoxybenzyl group, $R^3$ and $R^4$ are both hydrogens, X is OH and n is 2.

In other specific embodiments, the invention relates to compounds having the above formula wherein $R^1$ is a small alkyl group and more particularly an ethyl group, $R^2$ is an optionally substituted arylalkoxy group, $R^3$ and $R^4$ are both hydrogens, X is OH and n is 2. Specific compounds of the invention are those as above in which $R^1$ is an ethyl group, R2 is an optionally substituted arylalkoxy group, $R^3$ and $R^4$ are both hydrogens, X is OH and n is 2. A specific compound of the invention is that as above in which $R^1$ is an ethyl group, $R^2$ is a propoxybenzyl group, $R^3$ and $R^4$ are both hydrogens, X is OH and n is 2.

In other specific embodiments, the invention relates to compounds having the above formula wherein $R^1$ and $R^2$ form an optionally substituted ring, $R^3$ and $R^4$ are both hydrogens, X is OH and n is 1. Specific compounds of the invention are those as above in which $R^1$ and $R^2$ form an optionally substituted thiophenium group, $R^3$ and $R^4$ are both hydrogens, X is OH and n is 1. A specific compound of the invention is that as above in which $R^1$ and $R^2$ form a thiophenium group, $R^3$ and $R^4$ are both hydrogens, X is OH and n is 1. A specific compound of the invention is that as above in which $R^1$ and $R^2$ form a 3-phenylthiophenium group, $R^3$ and $R^4$ are both hydrogens, X is OH and n is 1.

In other specific embodiments, the invention relates to compounds having the above formula wherein $R^1$ and $R^2$ form an optionally substituted ring, $R^3$ and $R^4$ are both hydrogens, X is OH and n is 2. Specific compounds of the invention are those as above in which $R^1$ and $R^2$ form an optionally substituted thiophenium group, $R^3$ and $R^4$ are both hydrogens, X is OH and n is 2. A specific compound of the invention is that as above in which $R^1$ and $R^2$ form a thiophenium group, $R^3$ and $R^4$ are both hydrogens, X is OH and n is 2.

In other specific embodiments, the invention relates to compounds having the above formula wherein $R^1$ and $R^2$ form an optionally substituted ring, $R^3$ and $R^4$ are both hydrogens, X is OH and n is 3. Specific compounds of the invention are those as above in which $R^1$ and $R^2$ form an optionally substituted thiophenium group, $R^3$ and $R^4$ are both hydrogens, X is OH and n is 3. A specific compound of the invention is that as above in which $R^1$ and $R^2$ form a thiophenium group, $R^3$ and $R^4$ are both hydrogens, X is OH and n is 3.

In other specific embodiments, the invention relates to compounds having the above formula wherein $R^1$ and $R^2$ form an optionally substituted ring, $R^3$ and $R^4$ are both hydrogens, X is OH and n is 1. Specific compounds of the invention are those as above in which $R^1$ and $R^2$ form an optionally substituted thiopyranium group, $R^3$ and $R^4$ are both hydrogens, X is OH and n is 1. A specific compound of the invention is that as above in which $R^1$ and $R^2$ form a thiopyranium group, $R^3$ and $R^4$ are both hydrogens, X is OH and n is 1.

In other specific embodiments, the invention relates to compounds having the above formula wherein $R^1$ and $R^2$ form an optionally substituted ring, $R^3$ and $R^4$ are both hydrogens, X is OH and n is 2. Specific compounds of the invention are those as above in which $R^1$ and $R^2$ form an optionally substituted thiopyranium group, $R^3$ and $R^4$ are both hydrogens, X is OH and n is 2. A specific compound of the invention is that as above in which $R^1$ and $R^2$ form a thiopyranium group, $R^3$ and $R^4$ are both hydrogens, X is OH and n is 2.

In a particular embodiment of CA11, X is OH, n=1, $R^3$ and $R^4$ are hydrogens, and $R^1$ and $R^2$ are selected from the group consisting of optionally substituted alkyl groups, optionally substituted arylalkyl groups and optionally substituted arylalkoxy groups. Of particular interest are those compounds in which $R^1$ is a methyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein n is 1, $R^3$ and $R^4$ are hydrogens, X is OH or H, and $R^1$ and $R^2$ are selected from the group consisting of optionally substituted alkyl groups, optionally substituted arylalkyl groups and optionally substituted arylalkoxy groups. Of particular interest are those compounds in which $R^1$ is a methyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein X is OH, n=2, $R^3$ and $R^4$ are hydrogens, and $R^1$ and $R^2$ are selected from the group consisting of optionally substituted alkyl groups, optionally substituted arylalkyl groups and optionally substituted arylalkoxy groups. Of particular interest are those compounds in which $R^1$ is a methyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein n is 2, $R^3$ and $R^4$ are hydrogens, X is OH or H, and $R^1$ and $R^2$ are selected from the group consisting of optionally substituted alkyl groups, optionally substituted arylalkyl groups and optionally substituted arylalkoxy groups. Of particular interest are those compounds in which $R^1$ is a methyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein X is OH, n=3, $R^3$ and $R^4$ are hydrogens, and $R^1$ and $R^2$ are selected from the group consisting of optionally substituted alkyl groups, optionally substituted arylalkyl groups and optionally substituted arylalkoxy groups. Of particular interest are those compounds in which $R^1$ is a methyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein n is 3, $R^3$ and $R^4$ are hydrogens, X is OH or H, and $R^1$ and $R^2$ are selected from the group consisting of optionally substituted alkyl groups, optionally substituted arylalkyl groups and optionally substituted arylalkoxy groups. Of particular interest are those compounds in which $R^1$ is a methyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein X is OH, n=2, $R^3$ and $R^4$ are hydrogens, and $R^1$ and $R^2$ are selected from the group consisting of optionally substituted alkyl groups, optionally substituted arylalkyl groups and optionally substituted arylalkoxy groups. Of particular interest are those compounds in which $R^1$ is an ethyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein n is 2, $R^3$ and $R^4$ are hydrogens, X is OH or H, and $R^1$ and $R^2$ are selected from the group consisting of optionally substituted alkyl groups, optionally substituted arylalkyl groups and optionally substituted arylalkoxy groups. Of particular interest are those compounds in which $R^1$ is an ethyl group and $R^2$ is selected from the group consisting of optionally substituted alkyl groups, optionally substituted arylalkyl groups and optionally substituted arylalkoxy groups.

In other specific embodiments, the invention includes compounds of formula CA11, wherein n is 1, $R^3$ and $R^4$ are hydrogens, X is OH or H, and $R^1$ and $R^2$ form an optionally substituted thiophenium group. Of particular interest is that compound where $R^1$ and $R^2$ form an unsubstituted thiophenium group or a 3-phenyl thiophenium group.

In other specific embodiments, the invention includes compounds of formula CA11, wherein n is 2, $R^3$ and $R^4$ are hydrogens, X is OH or H, and $R^1$ and $R^2$ form an optionally substituted thiophenium group. Of particular interest is that compound where $R^1$ and $R^2$ form an unsubstituted thiophenium group.

In other specific embodiments, the invention includes compounds of formula CA11, wherein n is 3, $R^3$ and $R^4$ are hydrogens, X is OH or H, and $R^1$ and $R^2$ form an optionally substituted thiophenium group. Of particular interest is that compound where $R^1$ and $R^2$ form an unsubstituted thiophenium group.

In other specific embodiments, the invention includes compounds of formula CA11, wherein n is 1, $R^3$ and $R^4$ are hydrogens, X is OH or H, and $R^1$ and $R^2$ form an optionally substituted thiopyranium group. Of particular interest is that compound where $R^1$ and $R^2$ form an unsubstituted thiopyranium group.

In other specific embodiments, the invention includes compounds of formula CA11, wherein n is 2, $R^3$ and $R^4$ are hydrogens, X is OH or H, and $R^1$ and $R^2$ form an optionally substituted thiopyranium group. Of particular interest is that compound where $R^1$ and $R^2$ form an unsubstituted thiopyranium group.

In embodiments, the invention provides compounds having the formula CA12:

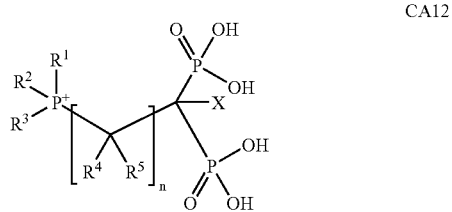

CA12 which can be in zwitterionic form (e.g., wherein one, and under certain circumstances more than one, of the OH groups of a phosphonate moiety can be depicted as an oxygen group with a negative charge) and/or as a pharmaceutically acceptable salt, ester, or hydrate thereof, with variations as would be understood from the teaching herein for other general formulas presented;

wherein:

X is H, —OH;

n is 1 or 2;

$R^1$-$R^3$, independently of one another and other R groups, are selected from the group consisting of a hydrogen, a halogen, a —CN, —OR, —COOR, , —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, and an optionally substituted aryl group, where each R, independent of any other R in any listed group, is selected from H, an optionally substituted alkyl group, an optionally substituted aryl group, and an optionally substituted acyl group;

two or more of $R^4$-$R^5$ can together form one or more rings which may contain one or more double bonds or which may be aromatic;

$R^4$ and $R^5$, independently of each other and other $R^4$ and $R^5$ in the compound, are selected from the group consisting of a hydrogen, a halogen, a —N(R)$_2$, or —SR group, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group; and wherein $R^4$ and $R^5$ can together form a ring which may contain one or more double bonds.

In specific embodiments, the invention relates to compounds having the above formula where X is OH.

In other specific embodiments, the invention relates to compounds having the above formula where X is H.

In other specific embodiments, compounds of the invention are those of formula CA12.

In other specific embodiments, the invention relates to compounds having the above formula wherein n is 1.

In other specific embodiments, the invention relates to compounds having the above formula where X is OH and n is 1.

In other specific embodiments, the invention relates to compounds having the above formula wherein one or both of $R^4$ and $R^5$ are hydrogens.

In other specific embodiments, the invention relates to compounds having the above formula wherein both of $R^4$ and $R^5$ are hydrogens.

In other specific embodiments, the invention relates to compounds having the above formula wherein both of $R^4$ and $R^5$ are hydrogens and n is 1.

In other specific embodiments, the invention relates to compounds having the above formula wherein both of $R^4$ and $R^5$ are hydrogens, n is 1 and X is OH.

In other specific embodiments, the invention relates to compounds having the above formula wherein both of $R^4$ and $R^5$ are hydrogens, n is 1 and X is H.

In other specific embodiments, the invention relates to compounds having the above formula wherein $R^1$-$R^3$ are optionally substituted alkyl groups chosen independently of one another and $R^4$-$R^5$ are both hydrogens.

In other specific embodiments, the invention relates to compounds having the above formula wherein $R^1$-$R^3$ are optionally substituted alkyl groups chosen independently of one another, $R^4$-$R^5$ are both hydrogens, X is OH and n is 1.

In other specific embodiments, the invention relates to compounds having the above formula wherein $R^1$-$R^3$ are optionally substituted alkyl groups chosen independently of one another, $R^4$-$R^5$ are both hydrogens, X is H and n is 1.

In other specific embodiments, the invention relates to compounds having the above formula wherein $R^4$ and $R^5$ are both hydrogens, and $R^1$, $R^2$ and $R^3$ are optionally substituted alkyl groups chosen independently of one another, particularly small alkyl groups and more particularly methyl groups.

In other specific embodiments, the invention relates to compounds having the above formula wherein $R^4$ and $R^5$ are both hydrogens, $R^1$, $R^2$ and $R^3$ optionally substituted alkyl groups chosen independently of one another, particularly small alkyl groups and more particularly methyl groups, X is OH and n is 1. Specific compounds of this invention are those as above in which $R^4$ and $R^5$ are both hydrogens, $R^2$, $R^3$ and $R^4$ are methyl groups, X is OH and n is 1.

In other specific embodiments, the invention relates to compounds having the above formula wherein $R^4$ and $R^5$ are both hydrogens, $R^1$, $R^2$ and $R^3$ are optionally substituted alkyl groups chosen independently of one another, particularly small alkyl groups and more particularly methyl groups, X is OH and n is 2. Specific compounds of this invention are those as above in which $R^4$ and $R^5$ are both hydrogens, $R^2$, $R^3$ and $R^4$ are methyl groups, X is OH and n is 1.

In a particular embodiment of CA12, X is OH, n=1, $R^1$-$R^3$ are methyl groups and $R^4$-$R^5$ are hydrogens.

In other specific embodiments, the invention includes compounds of formula CA12, wherein n is 1, $R^1$-$R^3$ are methyl groups and $R^4$-$R^5$ are hydrogens, X is OH or H.

In other specific embodiments, the invention includes compounds of formula CA12, wherein n is 2, $R^1$-$R^3$ are methyl groups and $R^4$-$R^5$ are hydrogens, X is OH or H.

In other specific embodiments, the invention includes compounds of formula CA12, wherein n is 1, $R^4$-$R^5$ are hydrogens, X is OH and $R^1$-$R^3$ are selected from the group consisting of optionally substituted alkyl groups, optionally substituted alkoxy groups and optionally substituted phenyl groups.

In a specific embodiment, compounds 536 and 541; and pharmaceutically acceptable salts, and esters thereof; are useful for treatment of a bone resorption clinical disorder.

In a specific embodiment, compounds 536 and 541; and pharmaceutically acceptable salts, and esters thereof; are useful in treatment of protozoan diseases, useful for treatment of a bone resorption clinical disorder, and for immunotherapy.

In a specific embodiment, compounds, the des-hydroxy (where X is H) analogs of compounds 536 and 541; and pharmaceutically acceptable salts, and esters thereof; are useful in the treatment of a bone resorption clinical disorder.

In embodiments, the invention provides compounds having the formula CA13:

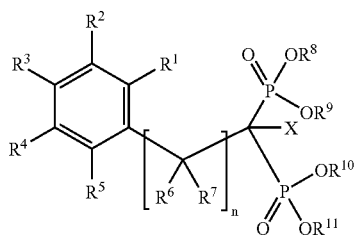

CA13 which can be in zwitterionic form (e.g., wherein one, and under certain circumstances more than one, of the OH groups of a phosphonate moiety can be depicted as an oxygen group with a negative charge) and/or as a pharmaceutically acceptable salt, ester, or hydrate thereof, with variations as would be understood from the teaching herein for other general formulas presented;

wherein:

X is H, —OH, a halogen, or a methyl group;

n is 1, 2, or 3;

$R^1$-$R^5$, independently of one another and other R groups, are selected from the group consisting of a hydrogen, a halogen, a —CN, —OR, —COOR, , —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, and an optionally substituted aryl group, where each R, independent of any other R in any listed group, is selected from H, an optionally substituted alkyl group, an optionally substituted aryl group, and an optionally substituted acyl group;

two or more of $R^1$-$R^5$ can together form one or more rings which may contain one or more double bonds or which may be aromatic;

$R^6$ and $R^7$, independently of each other and other $R^6$ and $R^7$ in the compound, are selected from the group consisting of a hydrogen, a halogen, a —N(R)$_2$, or —SR group, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group; and wherein $R^6$ and $R^7$ can together form a ring which may contain one or more double bonds; and wherein $R^8$-$R^{11}$ can be chosen from the group consisting of a hydrogen, a pivalolyl ester group, and an isopropyl carbonate group.

In specific embodiments, the invention relates to compounds having the above formula where X is H.

In other specific embodiments, the invention relates to compounds having the above formula where X is OH.

In other specific embodiments, the invention relates to compounds having the above formula where X is a halogen.

In other specific embodiments, the invention relates to compounds having the above formula where X is a methyl group.

In other specific embodiments, the invention relates to compounds having the above formula wherein n is 1.

In other specific embodiments, the invention relates to compounds having the above formula where X is H and n is 1.

In other specific embodiments, the invention relates to compounds having the above formula where X is OH and n is 1.

In other specific embodiments, the invention relates to compounds having the above formula where X is a halogen and n is 1.

In other specific embodiments, the invention relates to compounds having the above formula where X is a methyl group and n is 1.

In other specific embodiments, the invention relates to compounds having the above formula wherein n is 2.

In other specific embodiments, the invention relates to compounds having the above formula where X is H and n is 2.

In other specific embodiments, the invention relates to compounds having the above formula where X is OH and n is 2.

In other specific embodiments, the invention relates to compounds having the above formula where X is a halogen and n is 2.

In other specific embodiments, the invention relates to compounds having the above formula where X is a methyl group and n is 2.

In other specific embodiments, the invention relates to compounds having the above formula wherein n is 3.

In other specific embodiments, the invention relates to compounds having the above formula where X is H and n is 3.

In other specific embodiments, the invention relates to compounds having the above formula where X is OH and n is 3.

In other specific embodiments, the invention relates to compounds having the above formula where X is a halogen and n is 3.

In other specific embodiments, the invention relates to compounds having the above formula where X is a methyl group and n is 3.

In other specific embodiments, the invention relates to compounds having the above formula wherein one or both of $R^6$ and $R^7$ are hydrogens.

In other specific embodiments, the invention relates to compounds having the above formula wherein both of $R^6$ and $R^7$ are hydrogens.

In other specific embodiments, the invention relates to compounds having the above formula wherein both of $R^6$ and $R^7$ are hydrogens and n is 1.

In other specific embodiments, the invention relates to compounds having the above formula wherein both of $R^6$ and $R^7$ are hydrogens, n is 1 and X is H.

In other specific embodiments, the invention relates to compounds having the above formula wherein both of $R^6$ and $R^7$ are hydrogens, n is 1 and X is OH.

In other specific embodiments, the invention relates to compounds having the above formula wherein $R^1$ and $R^5$ are both hydrogens.

In other specific embodiments, the invention relates to compounds having the above formula wherein $R^1$ and $R^5$ are both hydrogen, X is H and n is 1.

In other specific embodiments, the invention relates to compounds having the above formula wherein $R^1$ and $R^5$ are both hydrogen, X is OH and n is 1.

In other specific embodiments, the invention relates to compounds having the above formula wherein $R^1$ and $R^5$ are both hydrogen, X is H and n is 2.

In other specific embodiments, the invention relates to compounds having the above formula wherein $R^1$ and $R^5$ are both hydrogen, X is OH and n is 2.

In other specific embodiments, the invention relates to compounds having the above formula wherein $R^1$ and $R^5$ are both hydrogen, X is H and n is 3.

In other specific embodiments, the invention relates to compounds having the above formula wherein $R^1$ and $R^5$ are both hydrogen, X is OH and n is 3.

In other specific embodiments, the invention relates to compounds having the above formula wherein $R^8$-$R^{11}$ are hydrogens.

In other specific embodiments, the invention relates to compounds having the above formula wherein $R^8$-$R^{11}$ are hydrogens, X is H and n is 1.

In other specific embodiments, the invention relates to compounds having the above formula wherein $R^8$-$R^{11}$ are hydrogens, X is OH and n is 1.

In other specific embodiments, the invention relates to compounds having the above formula wherein $R^8$-$R^{11}$ are hydrogens, X is H and n is 2.

In other specific embodiments, the invention relates to compounds having the above formula wherein $R^8$-$R^{11}$ are hydrogens, X is OH and n is 2.

In other specific embodiments, the invention relates to compounds having the above formula wherein $R^8$-$R^{11}$ are hydrogens, X is H and n is 3.

In other specific embodiments, the invention relates to compounds having the above formula wherein $R^8$-$R^{11}$ are hydrogens, X is OH and n is 3.

In other specific embodiments, the invention relates to compounds having the above formula wherein $R^8$-$R^{11}$ are pivalolyl ester groups.

In other specific embodiments, the invention relates to compounds having the above formula wherein $R^8$-$R^{11}$ are pivalolyl ester groups, X is H and n is 1.

In other specific embodiments, the invention relates to compounds having the above formula wherein $R^8$-$R^{11}$ are pivalolyl ester groups, X is H and n is 2.

In other specific embodiments, the invention relates to compounds having the above formula wherein $R^8$-$R^{11}$ are pivalolyl ester groups, X is H and n is 3.

In other specific embodiments, the invention relates to compounds having the above formula wherein $R^8$-$R^{11}$ are isopropyl carbonate groups.

In other specific embodiments, the invention relates to compounds having the above formula wherein $R^8$-$R^{11}$ are isopropyl carbonate groups, X is H and n is 1.

In other specific embodiments, the invention relates to compounds having the above formula wherein $R^8$-$R^{11}$ are isopropyl carbonate groups, X is H and n is 2.

In other specific embodiments, the invention relates to compounds having the above formula wherein $R^8$-$R^{11}$ are isopropyl carbonate groups, X is H and n is 3.

In other specific embodiments, the invention relates to compounds having the above formula wherein $R^1$ and $R^5$ are both hydrogen and one or more of $R^2$, $R^3$ or $R^4$ is a halogen.

In other specific embodiments, the invention relates to compounds having the above formula wherein $R^1$ and $R^5$ are both hydrogens, one or more of $R^2$, $R^3$ or $R^4$ is a halogen, X is H and n is 1.

In other specific embodiments, the invention relates to compounds having the above formula wherein $R^1$ and $R^5$ are both hydrogens, one or more of $R^2$, $R^3$ or $R^4$ is a cyano group.

In other specific embodiments, the invention relates to compounds having the above formula wherein $R^1$ and $R^5$ are both hydrogens, one or more of $R^2$, $R^3$ or $R^4$ is a cyano group, X is H and n is 1.

In other specific embodiments, the invention relates to compounds having the above formula wherein $R^1$ and $R^5$ are both hydrogens, one or more of $R^2$, $R^3$ or $R^4$ is an optionally substituted aryl group.

In other specific embodiments, the invention relates to compounds having the above formula wherein $R^1$ and $R^5$ are both hydrogens, one or more of $R^2$, $R^3$ or $R^4$ is an optionally substituted aryl group, X is H and n is 1. Specific aryl groups include but are not limited to the groups consisting of phenyl group, 2-phenylbenzene, 3-phenylbenzene, 4-phenylbenzene, 2-dibenzofuran, 3-dibenzofuran, and 4-dibenzofuran, all of which are optionally substituted.

In other specific embodiments, the invention relates to compounds having the above formula wherein $R^1$ and $R^5$ are both hydrogens, one or more of $R^2$, $R^3$ or $R^4$ is an optionally substituted aryl group, X is OH and n is 1. Specific aryl groups include but are not limited to the groups consisting of phenyl group, 2-phenylbenzene, 3-phenylbenzene, 4-phenylbenzene, 2-dibenzofuran, 3-dibenzofuran, and 4-dibenzofuran, all of which are optionally substituted.

In other specific embodiments, the invention relates to compounds having the above formula wherein $R^1$ and $R^5$ are both hydrogens, one or more of $R^2$, $R^3$ or $R^4$ is an optionally substituted aryl group, X is H and n is 2. Specific aryl groups include but are not limited to the groups consisting of phenyl group, 2-phenylbenzene, 3-phenylbenzene, 4-phenylbenzene, 2-dibenzofuran, 3-dibenzofuran, and 4-dibenzofuran, all of which are optionally substituted.

In other specific embodiments, the invention relates to compounds having the above formula wherein $R^1$ and $R^5$ are both hydrogens, one or more of $R^2$, $R^3$ or $R^4$ is an optionally substituted aryl group, X is OH and n is 2. Specific aryl groups include but are not limited to the groups consisting of phenyl group, 2-phenylbenzene, 3-phenylbenzene, 4-phenylbenzene, 2-dibenzofuran, 3-dibenzofuran, and 4-dibenzofuran, all of which are optionally substituted.

In other specific embodiments, the invention relates to compounds having the above formula wherein $R^1$ and $R^5$ are both hydrogens, one or more of $R^2$, $R^3$ or $R^4$ is an optionally substituted aryl group, X is H and n is 3. Specific aryl groups include but are not limited to the groups consisting of phenyl group, 2-phenylbenzene, 3-phenylbenzene, 4-phenylbenzene, 2-dibenzofuran, 3-dibenzofuran, and 4-dibenzofuran, all of which are optionally substituted.

In other specific embodiments, the invention relates to compounds having the above formula wherein $R^1$ and $R^5$ are both hydrogens, one or more of $R^2$, $R^3$ or $R^4$ is an optionally substituted aryl group, X is OH and n is 3. Specific aryl groups include but are not limited to the groups consisting of phenyl group, 2-phenylbenzene, 3-phenylbenzene, 4-phenylbenzene, 2-dibenzofuran, 3-dibenzofuran, and 4-dibenzofuran, all of which are optionally substituted.

In other specific embodiments, the invention includes compounds of formula CA13, wherein n is 1, $R^1$ and $R^5$ are both hydrogens, $R^6$ and $R^7$ are both hydrogens, $R^8$-$R^{11}$ are all hydrogens, X is H or OH, and one or more of $R^2$, $R^3$ or $R^4$ is selected from the group consisting of H, a halogen, and aryl groups.

In other specific embodiments, the invention includes compounds of formula CA13, wherein n is 1, $R^1$ and $R^5$ are both hydrogens, $R^6$ and $R^7$ are both hydrogens, $R^8$-$R^{11}$ are selected from the group consisting of hydrogen, pivalolyl ester groups, and isopropyl carbonate groups, X is H, and one or more of $R^2$, $R^3$ or $R^4$ is selected from the group consisting of H, a halogen, and aryl groups.

In a specific embodiment, compounds 491, 493-496, 498, 608, 618, 621-625, 640, 647, 648; and pharmaceutically acceptable salts, and esters thereof; are useful for treatment of cancer.

In a specific embodiment, compounds 491, 493-496, 498, 608, 618, 621-625, 640, 647, 648; and pharmaceutically acceptable salts, and esters thereof; are useful in treatment of protozoan diseases and useful for treatment of cancer.

Compounds of this invention and compounds useful in the methods of this invention include those of the above formulas and pharmaceutically-acceptable salts and esters of those compounds. Salts include any salts derived from the acids of the formulas herein which acceptable for use in human or veterinary applications. The term esters refers to hydrolyzable esters of diphosphonate compounds of the formulas herein. Salts and esters of the compounds of the formulas herein are those which have the same therapeutic or pharmaceutical (human or veterinary) properties as the diphosphonate compounds of the formulas herein. Various combinations of salts are possible, with each phosphonate carrying a 2-, 1- or neutral charge. In principle there are multiple charge states possible, for example 9 charge states, for certain bisphosphonates of this invention.

In a specific embodiment, the invention includes compounds of the above formula CA13 where n=1, $R^1$ and $R^3$-$R^7$ are hydrogens, X=OH, and $R^2$=H, optionally substituted alkyl, optionally substituted alkoxy, and optionally substituted phenyl. In a more specific embodiment, the invention includes compounds where n=1, $R^1$ and $R^3$-$R^7$ =H, X=OH, and $R^2$=H, alkyl, alkoxy, and phenyl. In a further specific embodiment, the invention includes compounds where n=1, $R^1$ and $R^3$-$R^7$ =H, X=OH, and $R^2$=H, methyl, ethyl, propyl, butyl, methoxy, ethoxy, propoxy, butoxy, or phenyl.

Therapeutic applications.

In an embodiment, the invention provides various methods relating to the treatment of clinical disease. In an embodiment, the invention provides a method of treating a bone resorption disorder comprising administering to a patient in need a composition comprising a compound of the invention.

In an embodiment, the invention provides a method of treating a cancer disorder comprising administering to a patient in need a composition comprising a compound of the invention. In a specific embodiment, the cancer is breast cancer. In a specific embodiment, the breast cancer involves an actual or potential bone metastatic condition. In a specific embodiment, the invention provides a method of treating myeloma, lymphoma, prostate cancer, an epidermoid cancer, or orthotopic tumors.

In an embodiment, the invention provides compounds and methods for use in a combination therapy in the treatment of cancer. In a specific embodiment, a combination therapy utilizes a bisphosphonate compound of the invention and a different chemotherapeutic agent which can optionally be a distinct other bisphosphonate compound. In a particular embodiment the different chemotherapeutic agent is alendronate, zoledronate, risedronate, pamidronate, fas ligand (FasL), mevastatin, dexamethasone, paclitaxel, epirubicin, docetaxel, imatinib mesylate, tumor necrosis factor (TNF)-related apoptosis inducing ligand (TRAIL), uracil-tegafur, gemcitabine, melphalan, doxorubicin, vincristine, or R115777 farnesyl transferase inhibitor (FTI) (Zarnestra®). In a particular embodiment, the combination of the bisphosphonate compound of the invention and the different chemotherapeutic agent has a synergistic effect. In another particular embodiment the combination has an additive effect.

In an embodiment, the invention provides a method of treating an infectious disease comprising administering to a patient in need a composition comprising a compound of the invention. In a specific embodiment, the infectious disease relates to an agent selected from the group consisting of: a virus, a bacterium, a fungus, and a protozoan parasite. In A specific embodiment, the virus is a retrovirus. In a more specific embodiment, the retrovirus is human immunodeficiency virus (HIV). In an embodiment, the protozoan parasite is *Leishmania major*. In an embodiment, the protozoan parasite is selected from the group consisting of: *Leishmania, Toxoplasma, Cryptosporidium, Plasmodium*, and *Trypanosoma*. In an embodiment, the infectious disease is selected from the group consisting of leishmaniasis, toxoplasmosis, cryptosporidiosis, sleeping sickness, and malaria.

In an embodiment, the invention provides a method of immunotherapy comprising administering to a patient in need a composition comprising a compound of the invention. In a specific embodiment, the method stimulates T cells in the patient. In a more specific embodiment, the method stimulates gamma delta T cells.

In an embodiment, the invention provides a method of screening a bisphosphonate test compound for a potential therapeutic activity, comprising: providing said bisphosphonate test compound, measuring a performance attribute of said test compound in at least three assays selected from the group consisting of: a *T. brucei* farnesyl diphosphate synthase (FPPS) assay, a *Dictyostelium discoideum* assay, a T cell activation assay, and a bone resorption assay, analyzing said performance attribute; and selecting said bisphosphonate test compound based on said attribute; thereby screening said bisphosphonate test compound. In a specific embodiment, the method further comprises providing a reference compound and comparing a performance attribute of said reference compound with said performance attribute of said test compound.

In an embodiment, the invention provides a method of treating bone pain comprising administering to a patient in need a compound of the invention. In a particular embodiment, the treatment of bone pain is in the context of a bone disease. In a particular embodiment, the treatment of bone pain is in the context of a patient with a metastatic cancer. In a particular embodiment, the metastatic cancer has spread to a bone location or originated in a bone location. For example, the treatment of bone pain can be achieved in a breast cancer patient wherein a metastatic breast cancer can or has spread to a bone location.

In an embodiment, the invention provides a method of synthesizing a bisphosphonate compound of the invention, for example of formulae BX1, CA11, CA12, CA13, and/or other general formulae, comprising: syntheses as shown and described herein, e.g. in schemes and as further would be understood in the art. For example, the synthesis of any of the functionally and/or therapeutically active compounds can be prepared according to techniques as disclosed herein and as would be routinely understood in the art. A general overview of methods for making bisphosphonates includes the following.

Scheme 6

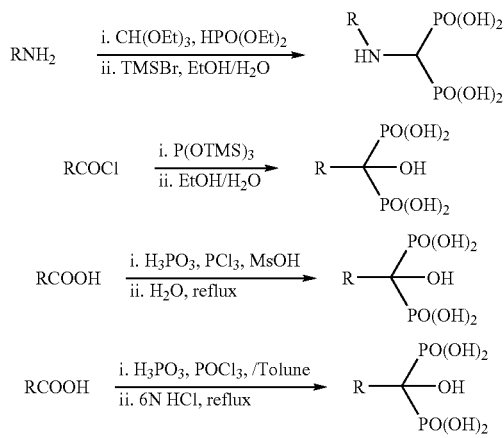

The syntheses depicted in Scheme 6 can be advantageous in that they are relatively short and in general give good yields (30-50%) of pure products. Purifications typically involve crystallization. Purities are in accord with standards of <0.4% error in C/H/N microanalysis; structures can be confirmed by $^1$H and $^{31}$P NMR spectroscopy.

Scheme 7 (sulfonium bisphosphonates)

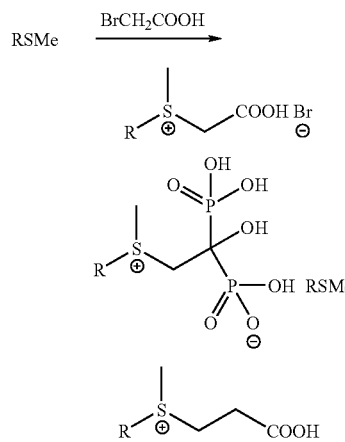

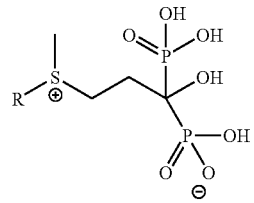

Scheme 8

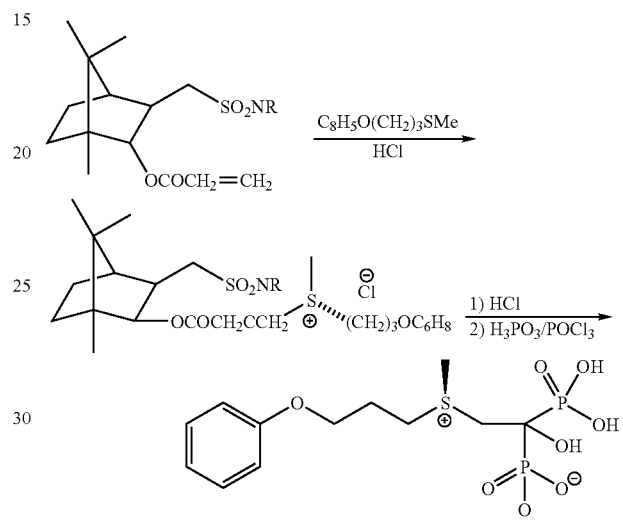

Scheme 3

Scheme 9 (including phosphonium, sulfoxide, and hydroxylamine analogs)

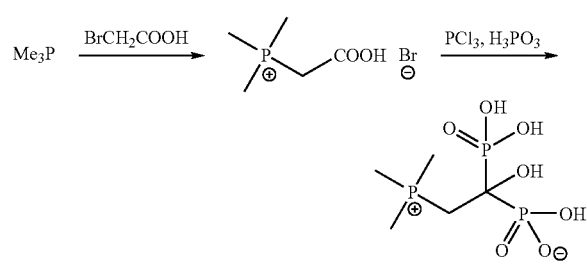

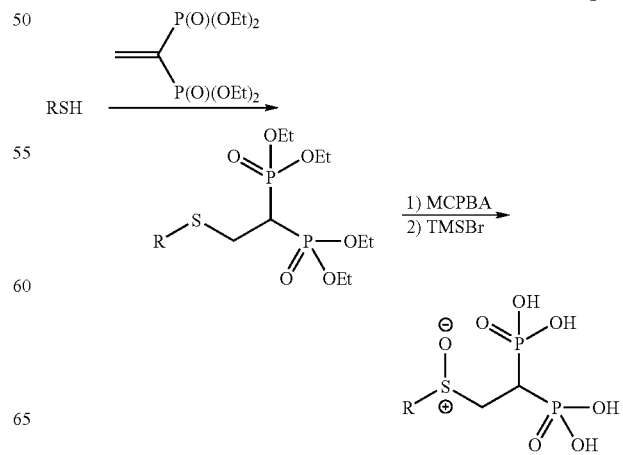

-continued

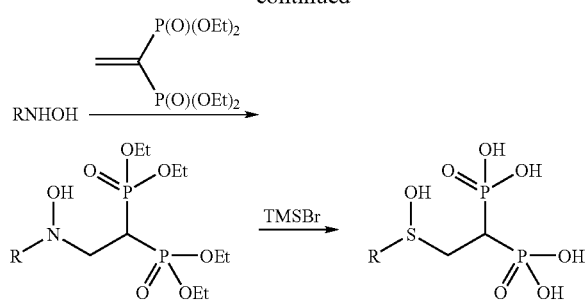

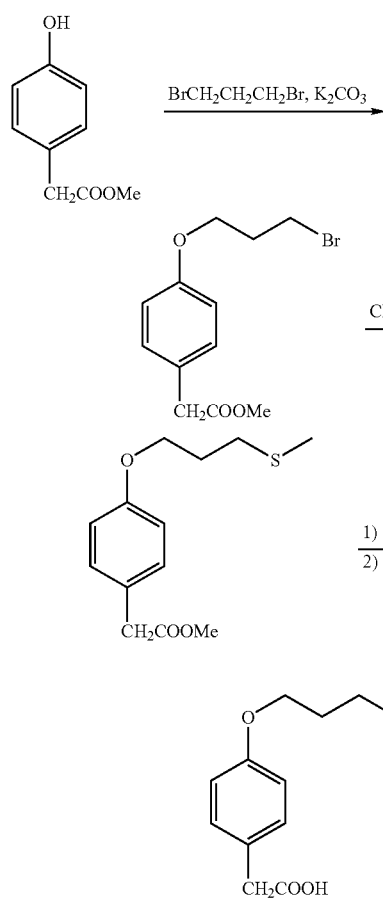

Scheme 10

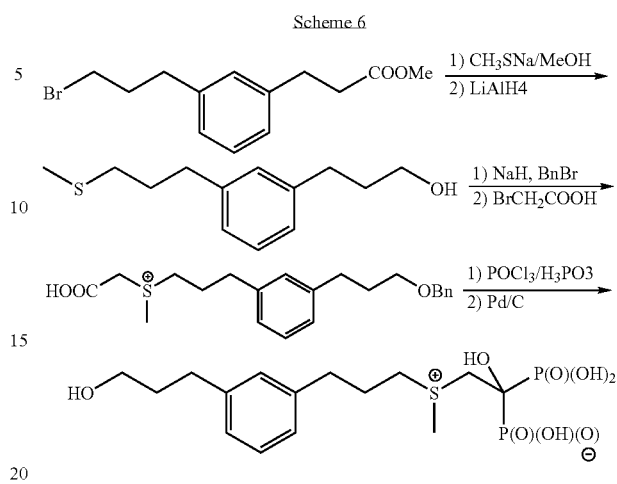

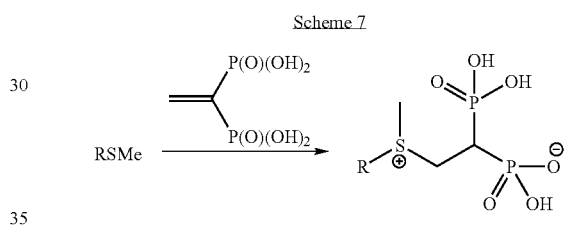

Scheme 12. In an approach to generate FPPS inhibitors, des-oxy analogs are generated, for example of risedronate. 1-des-oxy sulfonium bisphosphonates are generated and FPPS activity is measured; compounds with enhanced activity are selected and used to inhibit FPPS activity.

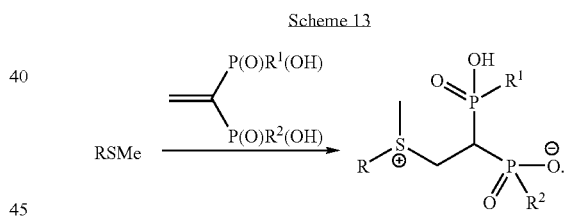

In connection with Scheme 10, the design of compounds can generate inhibitors that are specific for trypanosomes such as *T. brucei* and *T. cruzi*. In particular, inhibitors and selective inhibitors are generated, where a selective inhibitor can more specifically target a parasite enzyme such as FPPS relative to a host cell enzyme such as human FPPS.

Scheme 11. In another approach, enzyme inhibition such as FPPS inhibition is achieved by use of an alcohol functionality in a compound to form a hydrogen bond network with Tyr94 and Gln 167 in the *T. cruzi* enzyme (where enhanced H-bonding may relate to activity). In the scheme, the number of $CH_2$ spaces can be modified.

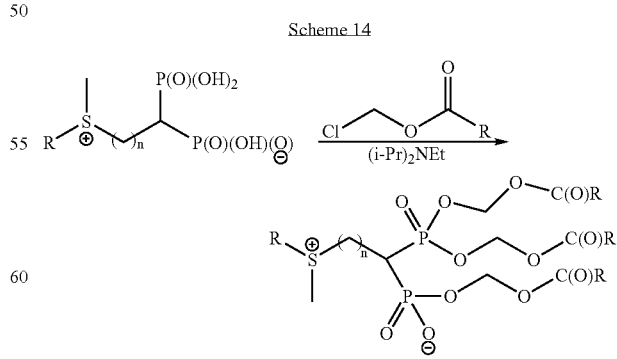

n = 1, 2

Figure 6:
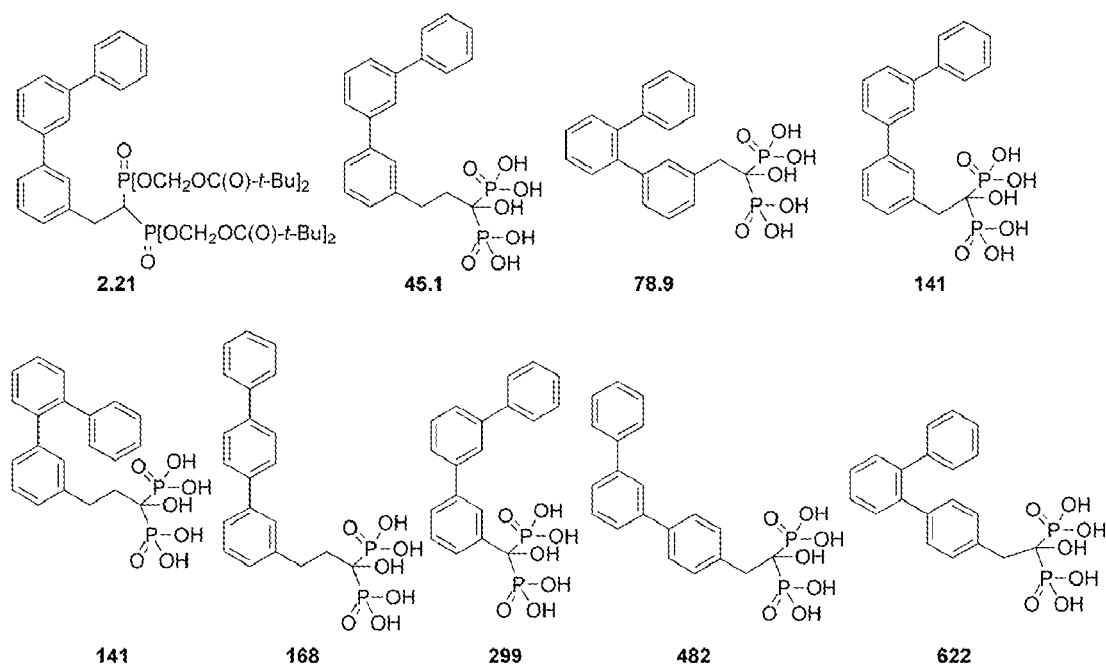
FIG. 6 illustrates terphenyl containing bisphosphonates and anti-tumor cell activity levels (μM) as described above.

Scheme 15—General Scheme for Terphenyl PIV Synthesis. Compounds were generated and tested. Activity levels (μM) for certain compounds are shown in FIG. 6. The non-nitrogen containing benzyl bisphosphonates show most potency with activity in the high nanomolar range. In order to improve cellular uptake, several of these new compounds include lipophilic pivaloyloxymethylene (PIV) esters on the phosphonate groups.

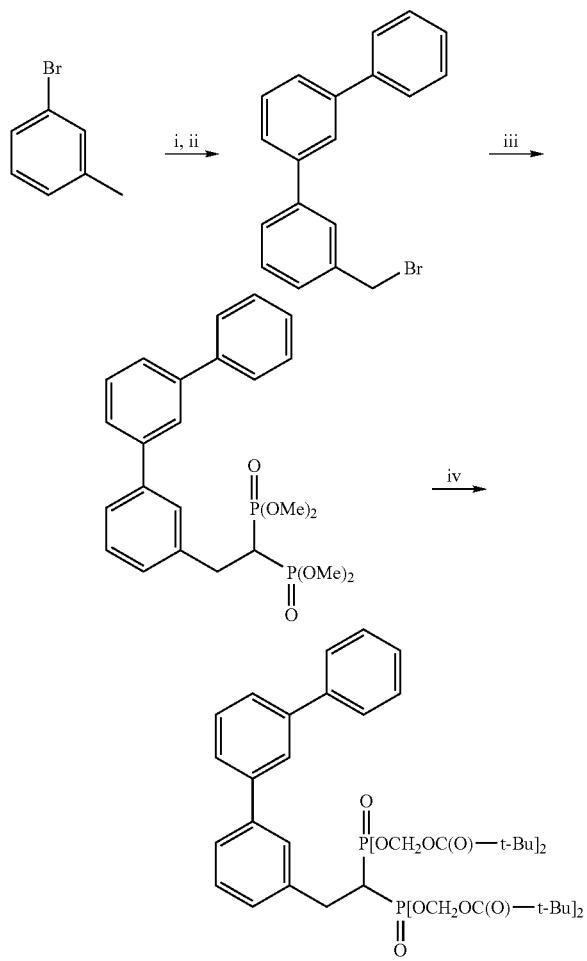

<sup>a</sup>Reagents: (i) 3-biphenylboronic acid, Pd(PPh₃)₄, K₂CO₃; (ii) NBS, AIBN; (iii) CH₂(POOMe)₂, NaH, 64% for three steps; (iv) ClCH₂OC(O)—t-Bu, NaI, reflux, 42% isolated yield.

EXAMPLE 5

Bisphosphonate Activity and *Trypanosoma cruzi*

Figure 7:
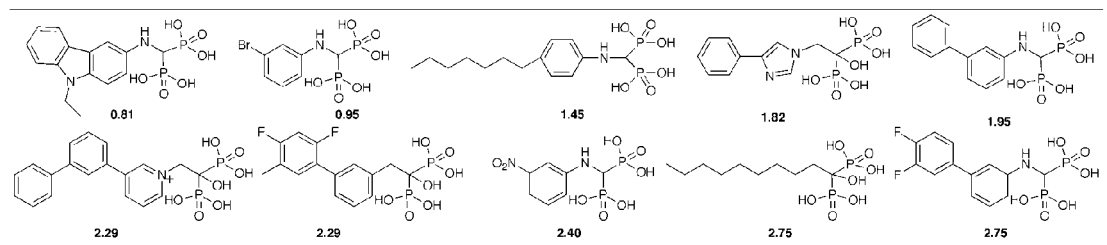
FIG. 7 illustrates bisphosphonate compounds with uncharged side-chains and activity levels for inhibiting a trypanosomal parasite enzyme, T. cruzi hexokinase.

Bisphosphonates are active against *Trypanosoma cruzi* and can be directed to *T. cruzi* hexokinase. Hexokinase is the first enzyme involved in glycolysis in most organisms, including the etiological agent of Chagas disease (*Trypanosoma cruzi*). Unlike the human enzyme, the TcHk enzyme can be regulated allosterically by inorganic diphosphate, and bisphosphonate analogues. Certain bisphosphonates with high activity in TcHk lack a positive charge in the side-chain, which can be a characteristic feature for FPPS inhibition. We attempted to reduce activity of these compounds in FPPS and have generated a new class of bisphosphonates which inhibit parasites. Certain compounds are believed to be able to provide para- site-specific enzyme inhibition. A new class of bisphosphonates with uncharged side-chains has activity against *T. cruzi* hexokinase. These compounds are believed to act as allosteric regulators of the enzyme. See FIG. 7 with activity levels for results of compounds which were tested (shown as μM values).

Figure 8:
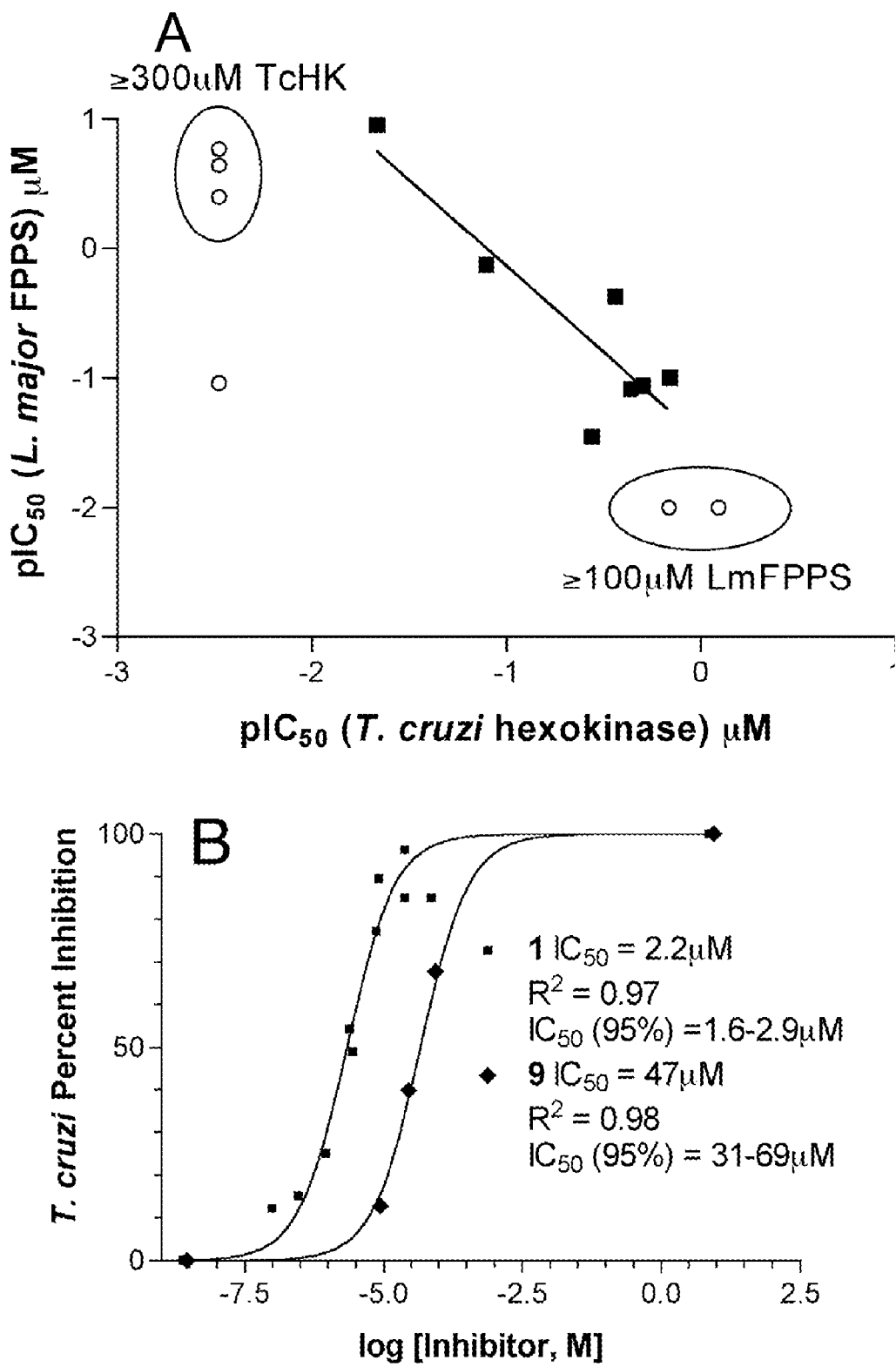
FIG. 8 illustrates data relating to anti-parasite activity. An inverse correlation has been observed between compounds active in T. cruzi hexokinase and L. major FPPS (FIG. 8A). Two active hexokinase inhibitors also show activity in the clinically relevant amastigote form of the trypanosome (FIG. 8B).

An inverse correlation has been observed between those compounds active in *T. cruzi* hexokinase and *L. major* FPPS. Modeling suggests that positive charge in side-chain is unfavorable in hexokinase, but this charge is required for FPPS activity. See FIG. 8A. Two active hexokinase inhibitors also show in vitro activity in the clinically relevant amastigote form of the trypanosome. See FIG. 8B.

EXAMPLE 6

Bisphosphonate Compounds and Anti-Bacterial Activity

We considered aspects of mevalonate and non-mevalonate pathway gene regulation. We determined that a bisphosphonate compound and fosmidomycin have anti-bacterial properties and are highly synergistic in *E. coli*.

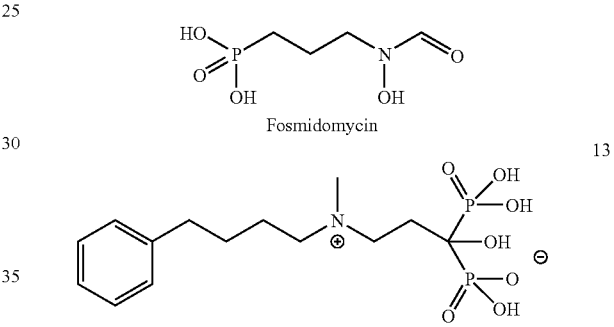

Figure 9:
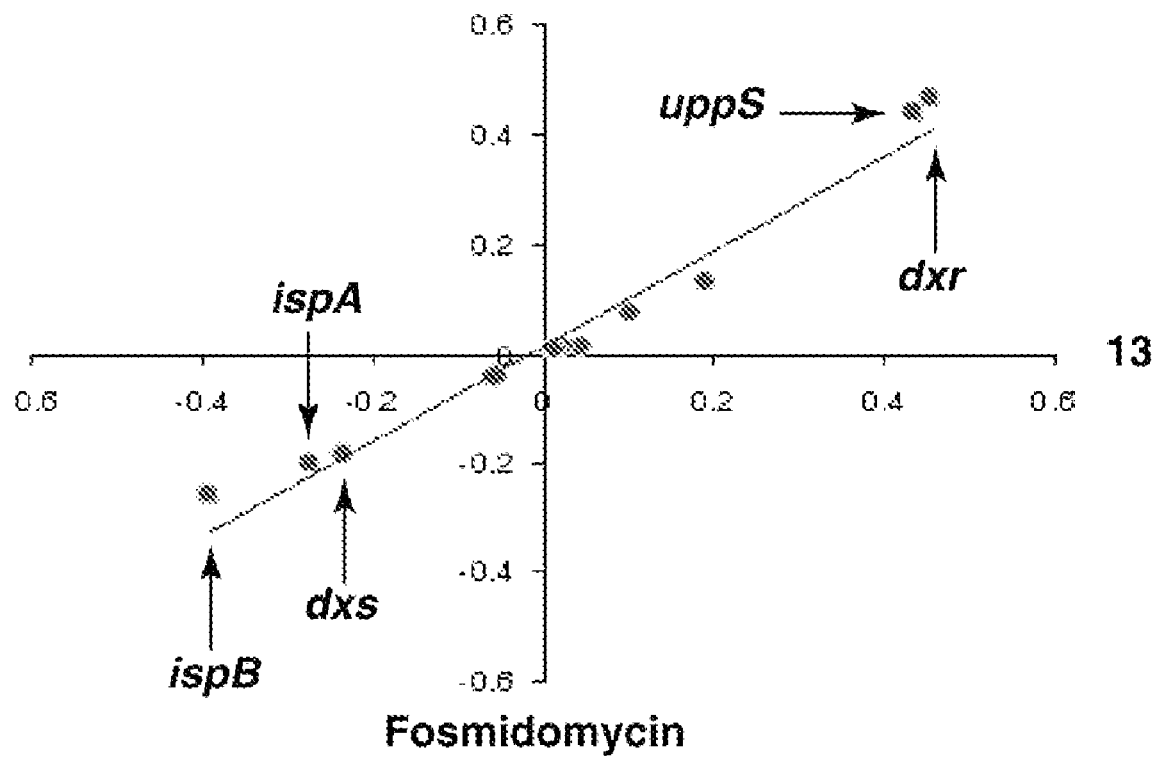
FIG. 9 illustrates results of analyzing relative changes in E. coli gene expression levels upon treatment with fosmidomycin and a bisphosphonate compound.

We generated a dendrogram showing the hierarchical cluster analysis of *E. coli* responses to compound 13, fosmidomycin, carbenicillin, ciprofloxacin, and the combination 13-fosmidomycin. We observed results for genes that significantly changed their expression relative to control. In particular, we tracked eleven genes from the isoprenoid biosynthesis pathway: dxs, ispG, ispH, idi, ispB, ispA, dxr, uppS, ispD, ispE, ispF. FIG. 9 shows results of analysis for Affymetrix GeneChip® antisense *E. coli* genome results. We observed relative increases and decreases in *E. coli* gene expression levels upon treatment with fosmidomycin and compound 13. In FIG. 9, each point represents the log2 expression ratio (to control) of one gene. The expression ratio is calculated for each gene from its estimated mean signal intensity determined for one treatment divided by the estimated mean signal intensity of that gene in untreated cells (eleven isoprenoid biosynthesis pathway genes); $R2=0.972$, $p<2.54$ E-8.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and subcombinations possible of the group are intended to be individually included in the disclosure. When a compound is described herein such that a particular isomer or enantiomer of the compound is not specified, for example, in a formula or in a chemical name, that description is intended to include each isomer and enantiomer of the compound described individually or in any combination. When an atom is described herein, including in a composition, any isotope of such atom is intended to be included. Specific names of compounds are intended to be exemplary, as it is known that one of ordinary skill in the art can name the same compounds differently. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation.

REFERENCES

U.S. Application Ser. No. 60783491 filed Mar. 17, 2006; U.S. application Ser. No. 11/245,612 filed Oct. 7, 2005 (see also US Patent Application Publication No. 20060079487 published Apr. 13, 2006); U.S. Application Ser. No. 60/617,108 filed Oct. 8, 2004; PCT International Application No. PCT/US05/036425 filed Oct. 7, 2005 (see also International Publication No. WO/2006/039721 published Apr. 13, 2006); US Patent Application Publication No. 20050113331 published May 26, 2005; the foregoing in particular are incorporated by reference in entirety to the extent not inconsistent herewith.

Hudock M P et al., Acta Cryst. (2006). E62, o843-o845.
Cao R et al., Acta Cryst. (2006). E62, o1003-o1005
Zhang Y et al., Acta Cryst. (2006). E62, o1006-o1008
Cao R et al., Acta Cryst. (2006). E62, o1055-o1057
Zhang Y et al., J Med Chem. 2006 Sep 21;49(19):5804-14.

(1) Sambrook, P. N.; Geusens, P.; Ribot, C.; Solimano, J. A.; Ferrer-Barriendos, J.; Gaines, K.; Verbruggen, N.; Melton, M. E. Alendronate produces greater effects than raloxifene on bone density and bone turnover in postmenopausal women with low bone density: results of EFFECT (EFficacy of FOSAMAX versus EVISTA Comparison Trial) International. J. Intern. Med. 2004, 255, 503-511.

(2) Vasireddy, S.; Talwakar, A.; Miller, H.; Mehan, R.; Swinson, D. R. Patterns of pain in Paget's disease of bone and their outcomes on treatment with pamidronate. Clin. Rheumatol. 2003, 22, 376-380.

(3) Dawson, N. A. Therapeutic benefit of bisphosphonates in the management of prostate cancer-related bone disease. Expert. Opin. Pharmacother. 2003, 4, 705-716.

(4) Rosen, L. S.; Gordon, D. H.; Dugan, W. Jr.; Major, P.; Eisenberg, P. D.; Provencher, L.; Kaminski, M.; Simeone, J.; Seaman, J.; Chen, B. L.; Coleman, R. E. Zoledronic acid is superior to pamidronate for the treatment of bone metastases in breast carcinoma patients with at least one osteolytic lesion. Cancer 2004,100, 36-43.

(5) Cromartie, T. H.; Fisher, K. J.; Grossman, J. N. The discovery of a novel site of action for herbicidal bisphosphonates. Pesticide Biochem. Phys. 1999, 63,114-126.

(6) Cromartie, T. H.; Fisher, K. J. Method of controlling plants by inhibition of farnesyl pyrophosphate synthase. U.S. Pat. No. 5,756,423, May 26, 1998.

(7) van Beek, E.; Pieterman, E.; Cohen, L.; Löwik, C.; Papapoulos, S. Nitrogen-containing bisphosphonates inhibit isopentenyl pyrophosphate isomerase/farnesyl pyrophosphate synthase activity with relative potencies corresponding to their antiresorptive potencies in vitro and in vivo. Biochem. Biophys. Res. Commun. 1999, 255, 491-494.

(8) van Beek, E.; Pieterman, E.; Cohen, L.; Löwik, C.; Papapoulos, S. Farnesyl pyrophosphate synthase is the molecular target of nitrogen-containing bisphosphonates. Biochem. Biophys. Res. Commun. 1999, 264,108-111.

(9) Keller, R. K.; Fliesler, S. J. Mechanism of aminobisphosphonate action: characterization of alendronate inhibition of the isoprenoid pathway. Biochem. Biophys. Res. Commun. 1999, 266, 560-563.

(10) Bergstrom, J. D.; Bostedor, R. G.; Masarachia, P. J.; Reszka, A. A.; Rodan, G. Mechanism of aminobisphosphonate action: characterization of alendronate inhibition of the isoprenoid pathway. Arch. Biochem. Biophys. 2000, 373, 231-241.

(11) Grove, J. E.; Brown, R. J.; Watts, D. J. The intracellular target for the antiresorptive aminobisphosphonate drugs in Dictyostelium discoideum is the enzyme farnesyl diphosphate synthase. J. Bone Miner. Res. 2000,15, 971-981.

(12) Dunford, J. E.; Thompson, K.; Coxon, F. P.; Luckman, S. P.; Hahan, F. M.; Poulter, C. D.; Ebetino, F. H.; Rogers, M. J. Structure-activity relationships for inhibition of farnesyl diphosphate synthase in vitro and inhibition of bone resorption in vivo by nitrogen-containing bisphosphonates. J. Pharmacol. Exp. Ther. 2001, 296, 235-242.

(13) Luckman, S. P.; Hughes, D. E.; Coxon, F. P.; Graham, R.; Russell, G.; Rogers, M. J. Nitrogen-containing bisphosphonates inhibit the mevalonate pathway and prevent post-translational prenylation of GTP-binding proteins, including Ras. J. Bone Miner. Res. 1998,13, 581-589.

(14) Fisher, J. E.; Rogers, M. J.; Halasy, J. M.; Luckman, S. P.; Hughes, D. E.; Masarachia, P. J.; Wesolowski, G.; Russell, R. G.; Rodan, G. A.; Reszka, A. A. Alendronate mechanism of action: geranylgeraniol, an intermediate in the mevalonate pathway, prevents inhibition of osteoclast formation, bone resorption, and kinase activation in vitro. Proc. Natl. Acad. Sci. USA 1999, 96,133-138.

(15) van Beek, E.; Löwik, C.; van der Pluijm, G.; Papapoulos, S. The role of geranylgeranylation in bone resorption and its suppression by bisphosphonates in fetal bone explants in vitro: A clue to the mechanism of action of nitrogen-containing bisphosphonates. J. Bone Miner. Res. 1999,14, 722-729.

(16) Montalvetti, A.; Bailey, B. N.; Martin, M. B.; Severin, G. W.; Oldfield, E.; Docampo, R. Bisphosphonates are potent inhibitors of Trypanosoma cruzi farnesyl pyrophosphate synthase. J. Biol. Chem. 2001, 276, 33930-33937.

(17) Sanders, J. M.; Gómez, A. O.; Mao, J.; Meints, G. A.; van Brussel, E. M.; Burzynska, A.; Kafarski, P.; González-Pacanowska, D.; Oldfield, E. 3-D QSAR investigations of the inhibition of Leishmania major farnesyl pyrophosphate synthase by bisphosphonates. J. Med. Chem. 2003, 46, 5171-5183.

(18) Martin, M. B.; Grimley, J. S.; Lewis, J. C.; Heath, H. T. III; Bailey, B. N.; Kendrick, H.; Yardley, V.; Caldera, A.; Lira, R.; Urbina, J. A.; Moreno, S. N.; Docampo, R.; Croft, S. L.; Oldfield, E. Bisphosphonates inhibit the growth of *Trypanosoma brucei, Trypanosoma cruzi, Leishmania donovani, Toxoplasma gondii*, and *Plasmodium falciparum*: A potential route to chemotherapy. J. Med. Chem. 2001, 44, 909-916.

(19) Martin, M. B.; Sanders, J. M.; Kendrick, H.; de Luca-Fradley, K.; Lewis, J. C.; Grimley, J. S.; van Brussel, E. M.; Olsen, J. R.; Meints, G. A.; Burzynska, A.; Kafarski, P.; Croft, S. L.; Oldfield, E. Activity of bisphosphonates against *Trypanosoma brucei rhodesiense*. J. Med. Chem. 2002, 45, 2904-2914.

(20) Moreno, B.; Bailey, B. N.; Luo, S.; Martin, M. B.; Kuhlenschmidt, M.; Moreno, S. N.; Docampo, R.; Oldfield, E. 31 P NMR of apicomplexans and the effects of risedronate on Cryptosporidium parvum growth. Biochem. Biophys. Res. Commun. 2001, 284, 632-637.

(21) Ghosh, S.; Chan, J. M.; Lea, C. R.; Meints, G. A.; Lewis, J. C.; Tovian, Z. S.; Flessner, R. M.; Loftus, T. C.; Bruchhaus, I.; Kendrick, H.; Croft, S. L.; Kemp, R. G.; Kobayashi, E. Effects of bisphosphonates on the growth of *Entamoeba Histolytica* and *Plasmodium* species in vitro and in vivo. J. Med. Chem. 2004, 47,175-187.

(22) Yardley, V.; Khan, A. A.; Martin, M. B.; Slifer, T. R.; Araujo, F. G.; Moreno, S. N.; Docampo, R.; Croft, S. L.; Oldfield, E. In vivo activities of farnesyl pyrophosphate synthase inhibitors against *Leishmania donovani* and *Toxoplasma gondii*. Antimicrob. Agents Chemother. 2002, 46, 929-931.

(23) Rodriguez, N.; Bailey, B. N.; Martin, M. B.; Oldfield, E.; Urbina, J. A.; Docampo, R. Radical cure of experimental cutaneous leishmaniasis by the bisphosphonate pamidronate. J. Infect. Dis. 2002,186,138-140.

(24) Garzoni, L. R.; Caldera, A.; Meirelles, M. N. L.; de Castro, S. L.; Meints, G.; Docampo, R.; Oldfield, E.; Urbina, J. A. Selective in vitro effects of the farnesyl pyrophosphate synthase inhibitor risedronate on *Trypanosoma cruzi*. Intl. J. Antimicrobial Agents 2004, 23, 273-285.

(25) Garzoni, L. R.; Waghabi, M. C.; Baptista, M. M.; de Castro, S. L.; Meirelles, M. N. L.; Britto, C.; Docampo, R.; Oldfield, E.; Urbina, J. A. Antiparasitic activity of risedronate in a murine model of acute Chagas' disease. Intl. J. Antimicrobial Agents 2004, 23, 286-290.

(26) Wang, L.; Kamath, A.; Das, H.; Li, L.; Bukowski, J. F. Antibacterial effect of human Vgamma2Vdelta2 T cells in vivo. J. Clin. Invest. 2001,108,1349-1357.

(27) Kunzmann, V.; Bauer, E.; Feurle, J.; Weissinger, F.; Tony, H. P.; Wilhelm, M. Stimulation of γδ T cells by aminobisphosphonates and induction of antiplasma cell activity in multiple myeloma. Blood 2000, 96, 384-392.

(28) Kato, Y.; Tanaka, Y.; Miyagawa, F.; Yamashita, S.; Minato, N. Targeting of tumor cells for human gammadelta T cells by nonpeptide antigens. J. Immunol. 2001,167, 5092-5098.

(29) Thompson, K.; Rogers, M. J. Statins prevent bisphosphonate-induced gammadelta-T-cell proliferation and activation in vitro. J. Bone Miner. Res. 2004,19, 278-288.

(30) Sanders, J. M.; Ghosh, S.; Chan, J. M. W.; Meints, G.; Wang, H.; Raker, A. M.; Song, Y.; Colantino, A.; Burzynska, A.; Kafarski, P.; Morita, C. T.; Oldfield, E. Quantitative structure-activity relationships for gammadelta T cell activation by bisphosphonates. J. Med. Chem. 2004, 47, 375-384.

(31) Wilhelm, M.; Kunzmann, V.; Eckstein, S.; Reimer, P.; Weissinger, F.; Ruediger, T.; Tony, H. P. gammadelta T cells for immune therapy of patients with lymphoid malignancies. Blood 2003,102, 200-206.

(32) Miyaura, N; Yanagi, T; Suzuki, A. The palladium-catalyzed cross-coupling reaction of phenylboronic acid with haloarenes in the presence of bases. Synth. Commun. 1981, 11, 513-519.

(33) Krapcho, A. P.; Ellis, M. Synthesis of regioisomeric difluoro- and 8-chloro-9-fluorobenz[g]isoquinoline-5,10-diones and SNAr displacements studies by diamines: bis(aminoalkyl)aminobenz[g]isoquinoline-5,10-diones. J. Fluorine Chem. 1998, 90,139-147.

(34) Zhang, L.; Liang, F.; Sun, L.; Hu, Y.; Hu, H. A novel and practical synthesis of 3-unsubstituted indolizines. Synthesis 2000,1733-1737.

(35) Harel, Z.; Kovalevski-Liron, E.; Lidor-Hadas, R.; Lifshitz-Liron, R. Use of certain diluents for making bisphosphonic acids. World Patent W003097655, Nov. 27, 2003.

(36) Rogers, M. J.; Watts, D. J.; Russell, R. G.; Ji, X.; Xiong, X.; Blackburn, G. M.; Bayless, A. V.; Ebetino, F. H. Inhibitory effects of bisphosphonates on growth of amoebae of the cellular slime mold Dictyostelium discoideum. J. Bone Miner. Res. 1994, 9,1029-1039.

(37) van Beek, E. R.; Cohen, L. H.; Leroy, I. M.; Ebetino, F. H.; Lowik, C. W.; Papapoulos, S. E. Differentiating the mechanisms of antiresorptive action of nitrogen containing bisphosphonates. Bone 2003, 33, 805-11.

U.S. Pat. Nos.: 5,583,122 by Benedict et al., issued Dec. 10,1996; 6,562,974 by Cazer et al., issued May 13, 2003; 6,544,967 by Daifotis et al., issued Apr. 8, 2003; 6,410,520 by Cazer et al., issued Jun. 25, 2002; 6,372,728 by Ungell, issued Apr. 16, 2002; 6,638,920 by Thompson, issued Oct. 28, 2003; 4,777,163 by Bosies et al., issued Oct. 11, 1988; 4,939,130 by Jaeggi et al., issued Jul. 3, 1990; 4,859,472 by Demmer et al., issued Aug. 22, 1989; U.S. Pat. No. 5,227,506 by Saari et al., issued Jul. 13, 1993; U.S. Pat. No. 6,753,324 by Jomaa, issued Jun. 22, 2004. U.S. Pat. No. 5,294,608

Alfer'ev, I. S.; Mikhalin, N. V., Reactions of vinylidenediphosphonic acid with nucleophiles. 5. Addition of heterocyclic amines and trimethylamine to vinylidenediphosphonic acid; August 1994, Russian Chemical Bulletin 44(8):1528-1530 (translated from Izvestiya Akademii Nauk, Seriya Khimicheskaya 1995, 8,1590-1592).

Alfer'ev IS et al., Izvestiay Akademii Nauk SSSR, Seriya Khimicheskaya, No. 12, pp. 2802-2806, December 1983 [Bull. Acad. Sci. USSR, Div. Chem. Sci., 1983, 32:2515 (Engl. Transl.)].

Alfer'ev IS et al., Izv. Akad. Nauk SSSR, Ser. Khim., 1984:1122 [Bull. Acad. Sci. USSR, Div. Chem. Sci., 1984, 33:1031 (Engl. Transl.)].

International Publication No. WO03075741 by Wilder et al., published 18 September 2003; International Publication No. WO2004024165 by Baulch-Brown et al., published 25 Mar. 2004; German Patent Publication DE19859668 by Hassan, published 30 Dec. 1999; International Publication No. WO2004050096 by Romagne et al., published 17 Jun. 2004.

Widler L, et al., Highly potent geminal bisphosphonates. From pamidronate disodium (Aredia) to zoledronic acid (Zometa), J Med Chem. 2002 Aug 15;45(17):3721-38.

Green J R, Chemical and biological prerequisites for novel bisphosphonate molecules: results of comparative preclinical studies, Semin Oncol. 2001 Apr; 28(2 Suppl 6):4-10.

U.S. Pat. No. 4,711,880 by Stahl et al., issued Dec. 8, 1987 (Aredia/pamidronate); U.S. Pat. No. 4,621,077, U.S. Pat. No. 5,462,932, U.S. Pat. No. 5,994,329, U.S. Pat. No. 6,015,801, U.S. Pat. No. 6,225,294 (Fosamax/alendronate); U.S. Pat. No. 5,583,122, U.S. Pat. No. 6,096,342; U.S. Pat. No. 6,165,513 (Actonel/risedronate).

Wilhelm M et al., 2003, Gammadelta T cells for immune therapy of patients with lymphoid malignancies, Blood 102: 200-206.

Jagdev S P, Coleman R E, Shipman C M, Rostami H A, Croucher P I (2001); The bisphosphonate, zoledronic acid, induces apoptosis of breast cancer cells: evidence for synergy with paclitaxel. Br J Cancer 84:1126-1134.

U.S. Pat. No. 4,927,814 by Gall et al., issued May 22, 1990; U.S. Pat. Nos. 6,294,196 by Gabel et al., issued Sep. 25, 2001; 6,143,326 by Mockel, et al. issued Nov. 7, 2000 (ibandronate / Boniva®); 6,544,967 by Daifotis, et al. Apr. 8, 2003.

Heidenreich et al., 2004. Ibandronate in metastatic bone pain, Semin. Oncol. 31(5 Suppl 10):67-72.

Gordon D H, 2005. Efficacy and safety of intravenous bisphosphonates for patients with breast cancer metastatic to bone: a review of randomized, double-blind, phase III trials, Clin Breast Cancer. 6(2):125-31.

De Cock et al., 2005. Cost-effectiveness of oral ibandronate versus IV zoledronic acid or IV pamidronate for bone metastases in patients receiving oral hormonal therapy for breast cancer in the United Kingdom. Clin. Ther. 27(8):1295-310.

Sanders et al., Pyridinium-1-yl Bisphosphonates Are Potent Inhibitors of Farnesyl Diphosphate Synthase and Bone Resorption, J. Med. Chem. 2005, 48, 2957-296.

Kotsikorou Evangelia et al., Bisphosphonate Inhibition of the Exopolyphosphatase Activity of the Trypanosoma brucei Soluble Vacuolar Pyrophosphatase, J. Med. Chem. 2005, 48, 6128-6139.

Inoue S et al., 2003 Synthesis, 13:1971-1976. New synthesis of gem-Bis(phsophono)ethylenes and their Applications. J. Soloducho R. Gancarz P. Wieczorek J. Korf, J. Hafner, et al. Patent PL93-298436 (1997), Preparation of novel derivatives of (aminomethylene)bis(phosphonc acid) as herbicides.

M. Lecouvey, I. Mallard, T. Bailly, R. Burgada and Y. Leroux, Tet. Lett., 42, 8475-8478 (2001). A mild and efficient one-pot synthesis of 1-hydroxymethylene-1,1-bisphosphonic acids. Preparation of new tripod ligands.

G.R. Kieczykowski, R. B. Jobson, D. G. Melillo, D. F. Reinhold, V. J. Grenda, et al., J. Org. Chem., 60, 8310-8312 (1995) Preparaton of (4-amino-1-hydroxybutylidene) bisphosphonic and sodium salt, MK-217 (alendronate sodium). An improved procedure for the preparation of 1-hydroxy-1,1-bisphosphonic acids.

Harel, Z,; Kovalevski-Liron, E.; Lidor-Hadas, R.; R. Lifshitz-Liron, World Patent WO03097655, Nov. 27, 2003. Use of certain diluents for making bisphasphonic acids.

Soloducho J et al., 1997, Patent PL93-298436. Lecouvey M et al., 2001, Tet Lett 42:8475-8478. Kieczykowski GR et al, 1995, J Org Chem 60:8310-8312.

The invention claimed is:

1. A compound of formula BX1:

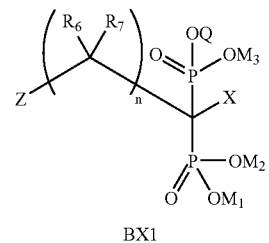

BX1 and salts, esters and hydrates thereof
where:
Q is M or a negative charge;
Z is selected from:

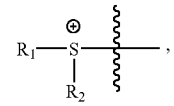
CX1

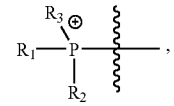
CX2

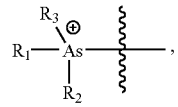
CX3

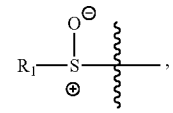
CX4

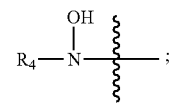
CX7

$M$, $M_1$, $M_2$ or $M_3$, independently of one another are H, alkyl, $—(CH_2)_p—O—CO—R$ or $—(CH_2)_p—O—C—R$ where p is 1 to 6, R is H, optionally substituted alkyl or optionally substituted aryl; $M_1$, $M_2$ or $M_3$ which are hydrogen may also be in form of a salt (—O⁻A⁺, where A⁺ is a cation);

X is H, halogen, OH or methyl;

n is 1, 2, or 3;

$R_6$ and $R_7$, independently of each other and other $R_6$ and $R_7$ in the compound, are selected from the group consisting of a hydrogen, a halogen, a —N(R)₂, or —SR group, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group where $R_6$ and $R_7$ can be linked together to form a 4-7 member ring;

$R_1$, $R_2$, $R_3$ and $R_4$, independently of one another, are selected from the group consisting of an optionally substituted alkyl group, an optionally substituted alkenyl group, an optionally substituted alkoxy group, and an optionally substituted aryl group wherein any two $R_1$-$R_3$ groups in the same molecule can be linked together to form a 4-7 member ring with the exception that $R_1$, $R_2$ and $R_3$ are not all methyl groups.

2. The compound of claim 1 wherein Z is CX4.
3. The compound of claim 1 wherein Z is CX2.
4. The compound of claim 1 wherein Z is CX3.
5. The compound of claim 1 wherein X=H.
6. The compound of claim 1 wherein X=OH.
7. A pharmaceutical formulation which comprised a compound of claim 1 and a pharmaceutically acceptable carrier.
8. The compound of formula BX1:

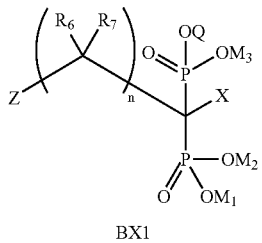

BX1 and salts, esters and hydrates thereof;

wherein:

Q is M or a negative charge;

Z is CX1:

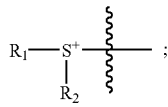

M, $M_1$, $M_2$ or $M_3$, independently of one another are H, alkyl, —(CH₂)ₚ—O—CO—R or —(CH₂)ₚ—O—C—R where p is 1 to 6, R is H, optionally substituted alkyl or optionally substituted aryl; $M_1$, $M_2$ or $M_3$ which are hydrogen may also be in form of a salt (—O⁻A⁺, where A⁺ is a cation);

X is H, halogen, OH or methyl;

n is 1, 2, or 3;

$R_6$ and $R_7$, independently of each other and other $R_6$ $R_7$ in the compound, are selected from the group consisting of a hydrogen, a halogen, a —N(R)₂, or —SR group, an optionally substituted alkyl group, an optionally substituted alkenyl group, an optionally substituted alkoxy group, and an optionally substituted aryl group, where each R, independent of any other R in any listed group, is selected from H, an optionally substituted alkyl group and an optionally substituted aryl group where $R_6$ and $R_7$ can be linked together to form a 4-7 member ring; and $R_1$, and $R_2$, independently of one another, are selected from the group consisting of an optionally substituted alkyl group, an optionally substituted alkenyl group, an optionally substituted alkoxy group, and an optionally substituted aryl group wherein any two $R_1$-$R_2$ groups in the same molecule can be linked together to form a 4-7 member ring, with the exception that $R_1$ and $R_2$ are not both methyl groups.

9. The compound of claim 8 wherein X=H.
10. The compound of claim 8 wherein X=OH.
11. The compound of claim 8 wherein the compound is selected from the group of compounds having formulas XX11, XX12, XX13 and XX14:

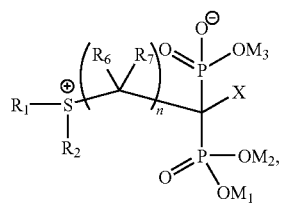

XX11

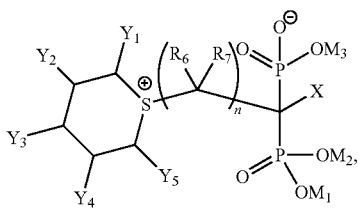

XX12

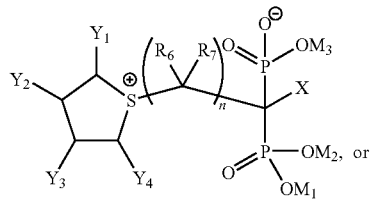

XX13

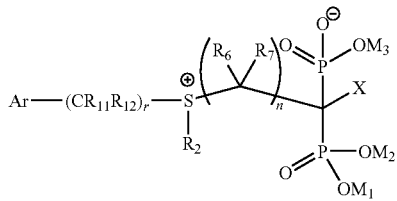

XX14 and salts, esters and hydrates thereof;

wherein $R_1$, and $R_2$, independently of one another, are selected from the group consisting of an optionally substituted alkyl group, an optionally substituted alkenyl group, an optionally substituted alkoxy group, and an optionally substituted aryl group with the exception that $R_1$ and $R_2$ are not both methyl groups;

$R_{11}$ and $R_{12}$ are selected from hydrogen, a halogen, a —CN, —OR, —COOR, —OCOOR, —COR, —CON(R)₂, —OCON(R)₂, —N(R)₂, —NO₂, —SR, —SO₂R, —SO₂N(R)₂ or —SOR group, an optionally substituted alkyl group, an optionally substituted alkenyl group, an optionally substituted alkynyl group and an optionally substituted aryl group; r is zero or an integer ranging from 1-10, or 1-6, wherein one or more $CR_{11}R_{12}$ moieties can be replaced with an O atom;

Ar is an optionally substituted aryl group;

$Y_1$-$Y_5$, independently of one another, are selected from the group consisting of a hydrogen, a halogen, a —ON, —OR, —COOR, —OCOOR, —COR, —CON(R)$_2$, —OCON(R)$_2$, —N(R)$_2$, —NO$_2$, —SR, —SO$_2$R, —SO$_2$N(R)$_2$ or —SOR group, an optionally substituted alkyl group, an optionally substituted alkenyl group, an optionally substituted alkynyl group and an optionally substituted aryl group which can be a heteroaryl group, wherein any two Y groups substituted on adjacent carbons of the same ring or any two carbons substituted on adjacent rings can be linked together to form a 4-7 member ring which may contain one or more double bonds, be aromatic and/or contain one or more heteroatoms (e.g., S, O or N); and each R, independent of any other R in any listed group, is selected from H, an optionally substituted alkyl group, an optionally substituted aryl group, and an optionally substituted acyl group.

12. The compound of claim 8 selected from the group consisting of compounds having the formulas: 546, 547, 550, 564, 569, 572, 573, 574, 575, 576, 580, 581, 584, 585, 587, 589, and 594; and for each respective said compound, a pharmaceutically acceptable salt, ester, or hydrate thereof; wherein such compound numbers have structures:

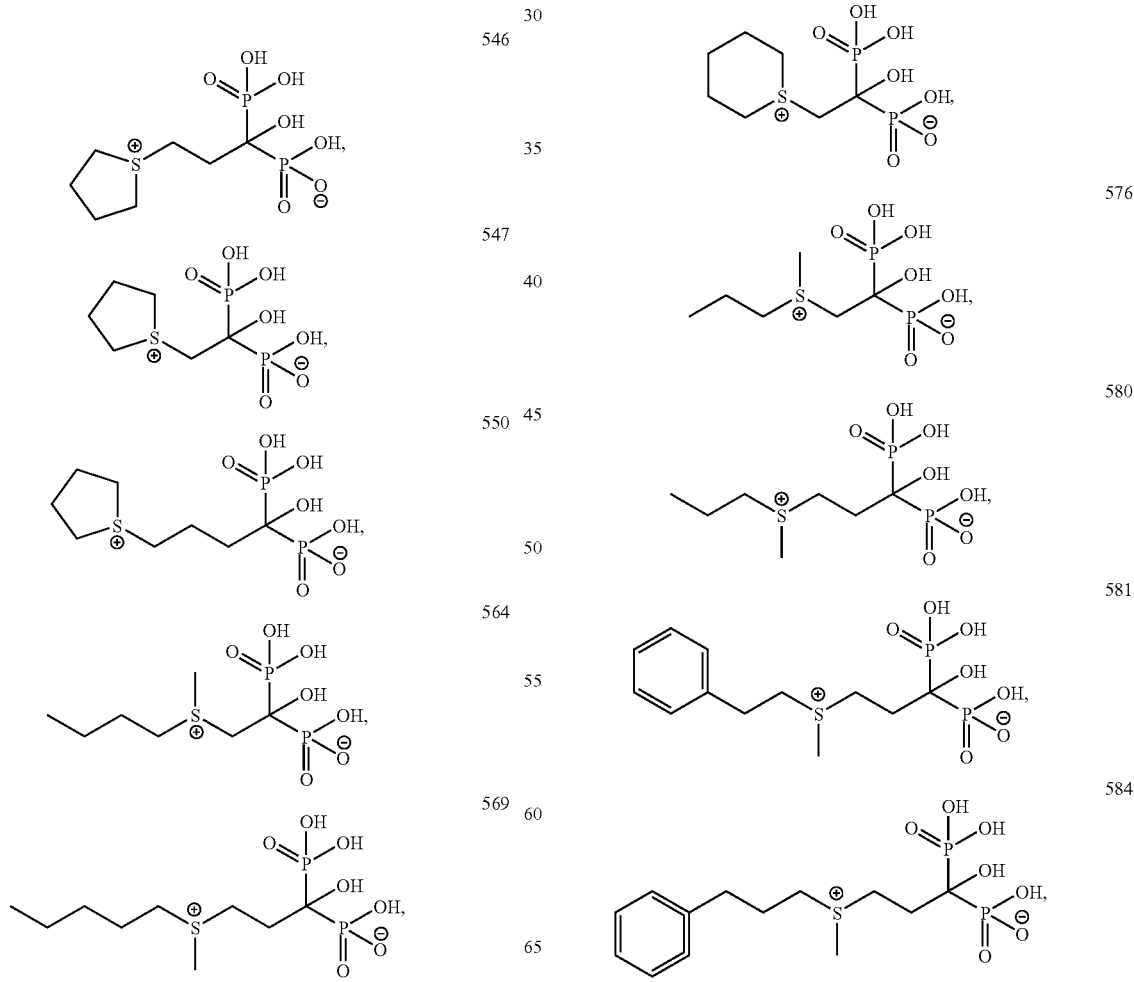

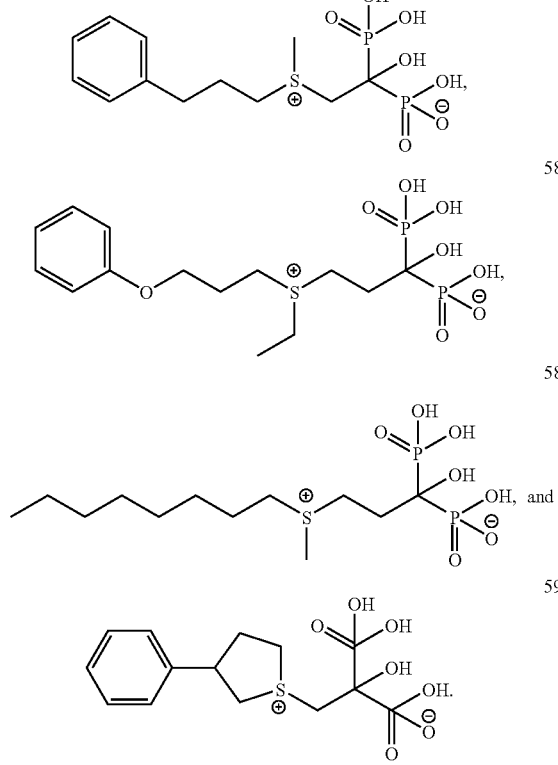

13. The compound of claim 8 wherein $R_1$, and $R_2$, independently of one another, are selected from the group consisting of optionally substituted alkyl groups, with the exception that $R_1$ and $R_2$ cannot both be methyl.

14. The compound of claim 8 wherein $R_1$ is an unsubstituted alkyl group having 2-20 carbon atoms and R2 is an unsubstituted alkyl group having 1, 2 or 3 carbon atoms.

15. The compound of claim 8 wherein n is 1, $R_6$ and $R_7$ are both H, $R_1$ is an unsubstituted alkyl group having 7-20 carbon atoms and $R_2$ is an unsubstituted alkyl group having 1, 2 or 3 carbon atoms.

16. The compound of claim 8 wherein n is 1, $R_6$ and $R_7$ are both H, $R_1$ is an unsubstituted alkyl group having 7-20 carbon atoms and $R_2$ is a methyl group.

17. The compound of claim 8 wherein n is 1, $R_6$ and $R_7$ are both H, $R_2$ is methyl and $R_1$ is an unsubstituted alkyl group having 7-10 carbon atoms, an alkyl group having 1-10 carbon atoms substituted with an aryl group.

18. The compound of claim 8 wherein n is 1, $R_6$ and $R_7$ are both H, $R_2$ is methyl and $R_1$ is an unsubstituted alkyl group having 7-10 carbon atoms, an alkyl group having 1-10 carbon atoms substituted with an optionally substituted phenyl group.

19. The compound of claim 11 wherein n is 1, $R_6$ and $R_7$ are both H, $R_2$ is methyl, $R_1$ is an unsubstituted alkyl group having 7-10 carbon atoms, Ar is an unsubstituted phenyl group, $R_{11}$ and $R_{12}$ are both H, r is 2-4 and —$(CR_{11}CR_{12})_r$— in formula XX14 can be replaced with —O—$(CR_{11}CR_{12})_{r-1}$—.

* * * * *